(12) United States Patent
Kaplan et al.

(10) Patent No.: US 8,609,835 B2
(45) Date of Patent: Dec. 17, 2013

(54) POLYSACCHARIDE COMPOSITION AND METHODS OF ISOLATION OF THE EMULSION STABILIZING CATIONIC POLYELECTROLYTIC POLYSACCHARIDE

(75) Inventors: David L. Kaplan, Concord, MA (US);
Bruce Panilaitis, Tewksbury, MA (US);
Michael Mercaldi, Bethesda, MD (US);
Hanna Dams-Kozlowska, Poznan (PL)

(73) Assignee: Trustees Of Tufts College, Boston, MA (US)

( * ) Notice: Subject to any disclaimer, the term of this patent is extended or adjusted under 35 U.S.C. 154(b) by 288 days.

(21) Appl. No.: 12/993,711

(22) PCT Filed: May 28, 2009

(86) PCT No.: PCT/US2009/045494
§ 371 (c)(1),
(2), (4) Date: Apr. 20, 2011

(87) PCT Pub. No.: WO2009/155059
PCT Pub. Date: Dec. 23, 2009

(65) Prior Publication Data
US 2011/0206772 A1    Aug. 25, 2011

Related U.S. Application Data

(60) Provisional application No. 61/056,571, filed on May 28, 2008.

(51) Int. Cl.
| | | |
|---|---|---|
| C08B 37/00 | (2006.01) | |
| A61K 9/14 | (2006.01) | |
| A61K 31/715 | (2006.01) | |
| C07H 5/04 | (2006.01) | |

(52) U.S. Cl.
USPC ........ 536/123.1; 536/55.1; 536/55.2; 514/54; 424/493

(58) Field of Classification Search
USPC ......... 536/123.1, 55.1, 55.2; 514/54; 424/493
See application file for complete search history.

(56) References Cited

U.S. PATENT DOCUMENTS

| | | | |
|---|---|---|---|
| 4,311,831 | A | 1/1982 | Gutnick et al. |
| 7,157,443 | B2 | 1/2007 | Joyce et al. |
| 2003/0170313 | A1 | 9/2003 | Prokop |
| 2004/0058006 | A1 | 3/2004 | Barry et al. |
| 2005/0008572 | A1 | 1/2005 | Prokop et al. |
| 2005/0271730 | A1 | 12/2005 | Dellacherie |
| 2007/0154492 | A1 | 7/2007 | Michon et al. |
| 2008/0038333 | A1 | 2/2008 | Magdassi |

OTHER PUBLICATIONS

Castro et al. (Appl. Microbiol. Biotechnol. (2005) vol. 67, pp. 767-770.*
Appl. Microbiol. Biotechnol. (2006) vol. 71, pp. 34-38.
Appl. Microbiol. Biotechnol. (2005) vol. 67, pp. 767-770.

* cited by examiner

*Primary Examiner* — Shaojia Anna Jiang
*Assistant Examiner* — Michael C Henry
(74) *Attorney, Agent, or Firm* — Thomas J. Engellenner; Reza Mollaaghababa; Pepper Hamilton LLP

(57) ABSTRACT

The present invention relates to purification and use of a novel emulsion stabilizing polysaccharide. In particular, a polyelectrolyte exopolysaccharide with high molecular weight comprising a high molecular weight polymer with a tri-saccharide repeating unit is disclosed. In one aspect of the invention, methods are directed to isolating and purifying a high molecular weight exopolysaccharide (EPS) from a cell supernatant. In another aspect, methods are disclosed for isolating a lipopolysaccharide (LPS) and a high molecular weight *Acinetobacter* polyelectrolyte exopolysaccharide (APE) from *Acinetobacter* bacteria. Compositions are also directed to lipid nanoparticles comprising a therapeutic agent encapsulated by a high molecular weight polysaccharide and nanoparticles comprising a therapeutic agent bound to a cationic polysaccharide cross-linked with a polyanion.

16 Claims, 25 Drawing Sheets

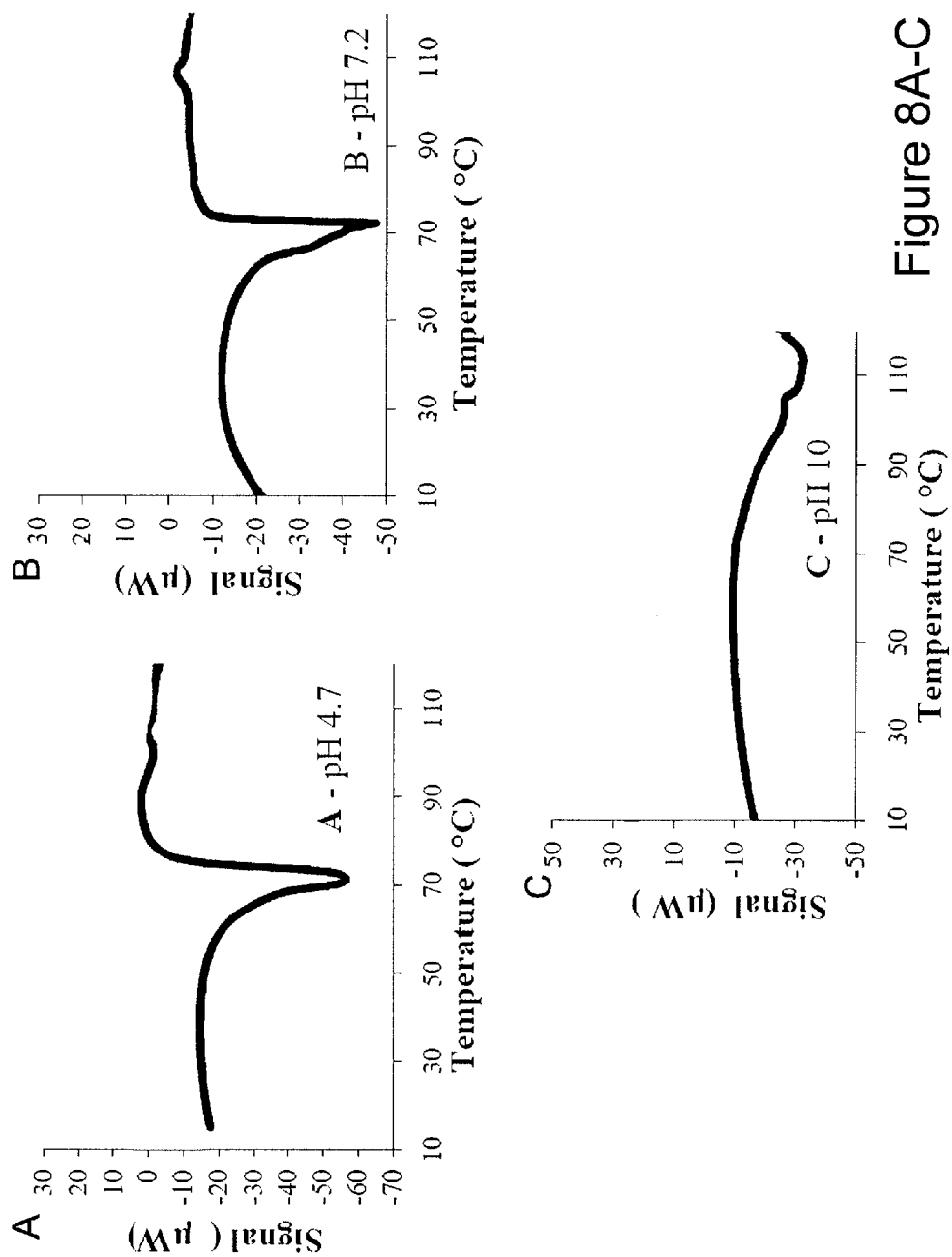
Figure 8A-C

POLYSACCHARIDE COMPOSITION AND METHODS OF ISOLATION OF THE EMULSION STABILIZING CATIONIC POLYELECTROLYTIC POLYSACCHARIDE

RELATED APPLICATIONS

The present application claims priority to U.S. Provisional Application No. 60/056,571 filed May 28, 2008 the content of which is hereby incorporated by reference in its entirety.

GOVERNMENT SUPPORT

Part of the work leading to this invention was carried out with United States Government support provided under a grant from the National Institutes of Health (NIH), Grant Nos. R01 AI055976 & R43 GM075513. Therefore, the U.S. Government has certain rights in this invention.

FIELD OF THE INVENTION

The technical field of the invention is emulsion stabilizing polysaccharide compositions and methods of isolating such compositions.

BACKGROUND OF THE INVENTION

*Acinetobacter venetianus* RAG-1 has been studied for its ability to metabolize a variety of carbon sources such as long chain hydrocarbons, alcohols, fatty acids, and triglycerides and to generate an exopolymer termed emulsan (Gorkovenko, A.; Zhang, J.; Gross, R. A.; Kaplan, D. L. *Carbohydrate Polymers* 1999, 1, 79-84). The bacterium has been reported to secrete this anionic lipoheteropolysaccharide known as emulsan to aid in the capture and transport of the carbon sources to the cell (Pines, O.; Bayer, E. A.; Gutnick, D. L. *Journal of Bacteriology* 1983, 2, 893-905). Emulsan has been described as a 1 MDa anionic lipopolysaccharide composed of the three amino sugars, D-galactosamine, D-galactosamineuronic acid, and diamino-6-deoxy-D-glucose, present in a ratio of 1:1:1 (Zuckerberg, A.; Diver, A.; Peeri, Z. *Applied and Environmental Microbiology* 1979, 3, 414-420). Saturated and monounsaturated fatty acids ranging from C10-C18 were reported to be linked to the polysaccharide backbone by O- and N-acyl bonds and to constitute up to 23% w/w of the polymer (Belsky, I.; Gutnick, D. L.; Rosenberg, E. *FEBS Letters* 1979, 1, 175-178). According to the previous literature, the emulsan amino groups are either acylated or covalently linked by an amide bond to 3-hydroxybutyric acid (Panilaitis, B.; Johri, A.; Blank, W.; Kaplan, D.; Fuhrman, J. *Clinical and Diagnostic Laboratory Immunology* 2002, 6, 1240-1247). The combination of hydrophilic anionic sugar main chain repeat units and the hydrophobic side groups were believed to impart an amphipathic behavior to emulsan and result in its ability to form stable oil-in-water emulsions (Rosenberg, E.; Zuckerberg, A.; Rubinovitz, C.; Gutnick, D. L. *Applied and Environmental Microbiology* 1979, 3, 402-408). Traditionally, studies with emulsan have focused on environmental applications, such as biodegradable surfactants, crude oil viscosity modifiers and the removal of heavy metals (Gutnick, D. L.; Bach, H. *Applied Microbiology and Biotechnology* 2000, 4, 451-460; Pines, O.; Gutnick, D. *Applied and Environmental Microbiology* 1986, 3, 661-663; Zosim, Z.; Gutnick, D.; Rosenberg, E. *Biotechnology and Bioengineering* 1983, 7, 1725-1735).

Recently, emulsan has been investigated for biological uses such as a vaccine adjuvant and as a drug delivery vehicle (Panilaitis, B.; Johri, A.; Blank, W.; Kaplan, D.; Fuhrman, J. *Clinical and Diagnostic Laboratory Immunology* 2002, 6, 1240-1247; Castro, G. R.; Kamdar, R. R.; Panilaitis, B.; Kaplan, D. L. *Journal of Controlled Release* 2005, 1-3, 149-157; Castro, G. R.; Panilaitis, B.; Bora, E.; Kaplan, D. L. *Molecular Pharmaceutics* 2007, 1, 33-46). However, in order to utilize emulsan in these types of biomedical applications, an improved purification process was required to avoid potential contaminants with undesirable biological side effects. Contaminants such as lipopolysaccharides (LPS), host cell protein (HCP), nucleic acids (DNA), and residual salts and solvents can potentially exhibit toxic effects on mammalian systems if present even in relatively low concentrations (Garnick, R. L.; Ross, M. J.; du Mee, Charles P. In *Encyclopedia of Pharmaceutical Technology*; Swarbick, J., Boyland, J. C., Eds.; Marcel Dekker: New York, N.Y., 1988; Vol. 1, pp 253-313). The purification of emulsan, first published in 1979, has traditionally been conducted using four steps; cell removal by centrifugation, ammonium sulfate precipitation of the polymer, hot phenol extraction to remove contaminating proteins, and dialysis against water to remove the phenol (Zuckerberg, A.; Diver, A.; Peeri, Z. *Applied and Environmental Microbiology* 1979, 3, 414-420). The scientific literature utilizing this purification approach has supported consistently that the emulsan from this purification scheme is an essentially pure product. However, the prior purification approaches do not result in a pure product, as demonstrated herein.

SUMMARY OF THE INVENTION

In one aspect, the invention demonstrates a novel polyelectrolyte polysaccharide. The polysaccharide can be isolated from a bacterium and is referred to as an exopolysaccharide (EPS). More specifically, the polysaccharide isolated from an *Acinetobacter* bacterium is referred to as *Acinetobacter* polyelectrolyte exopolysaccharide (APE). In a preferred embodiment, the polysaccharide can be isolated from a *Acinetobacter venetianus* RAG-1 cell.

The EPS of the invention possesses characteristics of a surfactant. Moreover, the APE is capable of reducing the surface tension of water. In particular, APE can reduce the surface tension of water below about 70 dynes/cm when at a concentration of about 5 mg/ml in water. The APE also has a high molecular weight with a tri-saccharide repeating unit. The molecular weight of APE can be greater than 3 MDa. The molecular weight of APE can also be in the range of about 3.4 MDa to about 4.7 MDa. The APE is substantially devoid of fatty acids, rendering it unique from the lipopolysaccharides characterized from emulsan.

The tri-saccharide repeating unit of APE can have the formula:

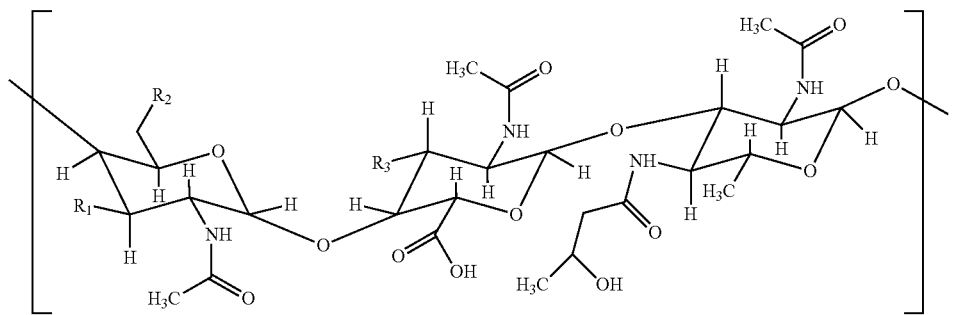

wherein R1, R2 and R3 are selected from the group consisting of OH and OAc. In another embodiment, the tri-saccharide can be →4)α-D-GalpNAc-6-OAc-(1→4)-α-D-GalpNAcA-(1→3)-α-D-QuipNAc4NHb-(1→, wherein NHb is a 3-hydroxybutyramide group. The tri-saccharide can also have at least one hydrophobic group, wherein the hydrophobic group can be an O-acetyl group, an uronic acid and a 3-hydroxybutyramido group. In yet another embodiment, the tri-saccharide repeating unit can comprise at least one N-acetyl galactosamine and can further comprise N-acetyl gluocosamine. Additionally, the tri-saccharide repeating unit can be partially deacetylated, where partially can refer to 1%, 5%, 10%, 20%, 30%, 40%, 50%, 60%, 70%, 80% or 90% deacetylated.

In another aspect, the present invention provides a new purification process capable of purifying a high molecular weight exopolysaccharide (EPS) from a cell supernatant comprising precipitating the high molecular weight EPS from the supernatant and extracting the precipitated EPS from the supernatant. The EPS can be purified to greater than 95% (w/w) using methods such as tangential flow filtration, Triton X-114 phase extraction, ammonium sulfate precipitation and hydrophobic interaction chromatography.

After growth in culture, bacterial cells can be harvested by centrifugation and a supernatant can be collected. The supernatant can be concentrated to reduce the total working volume by methods known in the art. One method of concentration can be by tangential flow filtration (TFF). Preferably, the supernatant can be concentrated to at least 10 times from a starting volume.

The supernatant can also be exposed to a detergent as one method of precipitating the EPS. For example, Triton X-114 can be used as a detergent. Treatment of the supernatant with a detergent can also remove contaminating elements such as LPS and hydrophobic proteins.

In another embodiment, the EPS can be extracted from the supernatant. The supernatant can be treated with a salt to precipitate the EPS. The salt can also aid in removing nucleic acids and contaminating polysaccharides. A preferred example of a precipitating salt can be ammonium salt. In an even more preferred embodiment, EPS can be precipitated with the use of ammonium sulfate. Additionally, the EPS can be extracted by column chromatography. In a preferred embodiment, hydrophobic interaction chromatography column can be used to separate the desired polysaccharide, i.e. EPS or APS, from the supernatant. The extracted polysaccharide can be collected and further dialyzed to remove any contaminating reagents.

Another aspect of the invention can be directed to isolating a lipopolysaccharide (LPS) and a high molecular weight *Acinetobacter* polyelectrolyte exopolysaccharide (APE) from *Acinetobacter venetianus* RAG-1 comprising the steps of obtaining a cell supernatant from *Acinetobacter venetianus* RAG-1, extracting the LPS from the supernatant, and extracting the APE from the LPS-extracted supernatant. The step of extracting the LPS can further comprise treating the supernatant with a denaturant to precipitate the LPS. In a preferred embodiment, the denaturant is guanidine hydrochloride. The denaturant can initiate the precipitation of LPS.

The LPS-extracted supernatant can further be exposed to a detergent as one method of precipitating the APE. The detergent can be one known by a skilled artisan. For example, Triton X-114 can be used as a detergent. Treatment of the supernatant with a detergent can also remove additional contaminating elements such as hydrophobic proteins.

In another embodiment, the APE can be extracted from the LPS-extracted supernatant. The supernatant can be treated with a salt to precipitate the APE. The salt can also aid in removing nucleic acids and contaminating polysaccharides. A preferred example of a precipitating salt can be ammonium salt. In an even more preferred embodiment, APE can be precipitated with the use of ammonium sulfate. Additionally, the APE can be extracted by column chromatography. Chromatography methods known by those skilled in the art with knowledge of APE physical properties, such as size, charge, pH, solubility etc, can be employed. In a preferred embodiment, hydrophobic interaction chromatography column can be used to separate the APE from the supernatant. The pure polysaccharide can be collected and further dialyzed to remove any contaminating reagents.

In another embodiment, the APE can reduce the surface tension of water below about 70 dynes/cm when APE is at a concentration of about 5 mg/mL in water. APE at pH 7.2 did not exhibit a limit to reduction of surface tension as concentrations increased, indicating that higher concentrations of the polysaccharide can further reduce the surface tension at this pH.

In another aspect to the invention, compositions are directed to a lipid nanoparticle comprising a therapeutic agent encapsulated by a high molecular weight polysaccharide wherein the polysaccharide has trisaccharide repeating units and a molecular weight greater than 3 MDa. The nanoparticle can be less than 1 micrometer. Preferably, the size of the particle is in the range from about 500 nm to about 100 nm. The lipid core of the nanoparticle can also comprise at least one lipid, such as monoglycerides, diglycerides, triglycerides, waxes and fatty acids. The tri-saccharide repeating units of the polysaccharide can comprise at least one N-acetyl galactosamine, N-acetyl glucosamine or a derivative.

In yet another aspect, a composition is directed to a therapeutic nanoparticle comprising a therapeutic agent bound together with a high molecular weight cationic polysaccharide cross-linked with a polyanion. In a preferred embodiment, the size of the nanoparticle ranges from about 300 nm to about 50 nm. The polysaccharide can also comprise trisaccharide repeating units and have a molecular weight greater than 3 MDa in an uncross-linked state. The polyanion can also be tripolyphosphate polyanion.

In another aspect, invention can be directed to a method of encapsulating a hydrophobic therapeutic agent. The method can comprise the steps of dissolving the therapeutic agent in a lipid, mixing the lipid solution with an aqueous solution comprising a high molecular weight polysaccharide having trisaccharide repeating units and a molecular weight greater than 3 MDa, homogenizing the resulting mixture at an elevated temperature to form an emulsion and cooling the emulsion to form particles having a therapeutic agent dispersed within a lipid core surrounded by the high molecular weight polysaccharide. Homogenization can be carried out at an elevated temperature. In a preferred embodiment, the temperature can be above 60 degrees C. The emulsion can further be cooled to form particles having a therapeutic agent dispersed within a lipid core surrounded by the high molecular weight polysaccharide. In one embodiment, the step of cooling the emulsion further comprises solidifying the core lipid.

The emulsion stabilizing cationic polysaccharide from *Acinetobacter venetianus* RAG-1 has been produced and purified according to a novel purification scheme. This purification process yields a greater than 95% pure product. The isolated polysaccharide has been determined to have a molecular weight of approximately 3.4 MDa-4.7 MDa, N-acetyl galactosamine rich polysaccharide that carries a net positive charge. It has demonstrated ability to bind negatively charged species at neutral pH, stabilize oil-in-water emulsions for an extended period of time and to be able to move when stimulated by an electrical current. The polysaccharide can also be used in lipid nanoparticles comprising a therapeutic agent or directly bound to the therapeutic agent.

DESCRIPTION OF THE DRAWINGS

FIG. 8. Microcalorimetry curves of APE at pH 4.7 (A), pH 7.2 (B) and pH 10 (C). Concentration of APE for experiments was 5 mg/ml. The heating curve is represented by the black line. The cooling curve is represented by the grey line.

DETAILED DESCRIPTION

Figure 1A:
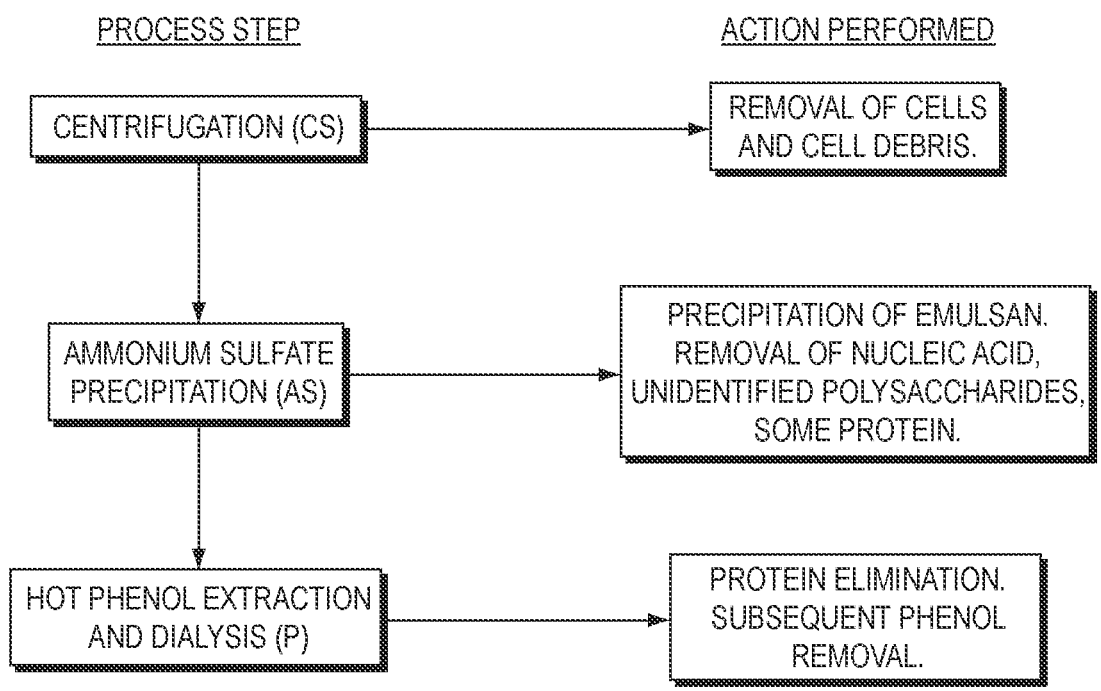
FIG. 1 shows a flow diagram of the purification process for (A) emulsan (EM) and for (B) the exopolysaccharide (EPS).

The invention is based, in part, on the discovery that emulsan is not a single polymer but rather a complex of a high molecular weight exopolysaccharide and R-type lipopolysaccharide. The exopolysaccharide that is produced by *A. venetianus* has been purified to at least 98% (w/w %) in preparation for preclinical work to establish biological safety and biomedical application efficacy.

Enclosed herein are methods for purification and use of a novel emulsion stabilizing polysaccharide. In particular, a polyelectrolyte exopolysaccharide with high molecular weight comprising a high molecular weight polymer with a tri-saccharide repeating unit is disclosed. In one aspect of the invention, methods are directed to isolating and purifying a high molecular weight exopolysaccharide (EPS) from a cell supernatant. In another aspect, methods are disclosed for isolating a lipopolysaccharide (LPS) and a high molecular weight *Acinetobacter* polyelectrolyte exopolysaccharide (APE) from *Acinetobacter venetianus* RAG-1. Compositions are also directed to a lipid nanoparticle comprising a therapeutic agent encapsulated by a high molecular weight polysaccharide and a therapeutic nanoparticle comprising a therapeutic agent bound to a cationic polysaccharide cross-linked with a polyanion.

Emulsan Complex

"Emulsan complex" or "emulsan" of the invention are extracellular products (e.g., secreted) of a bacterium, such as the gram negative bacterium *Acinetobacter venetianus* (*A. venetianus*). In a preferred embodiment, the emulsan is secreted from *A. venetianus*. Secreted refers to release from an intracellular compartment (e.g., cytoplasm, secretory granules) to the outside of the cell, for example, into the culture media.

"Polysaccharides" as defined herein, refer to polyanionic amphiphathic lipoheteropolyaccharides and high molecular weight exopolysaccharides. The term "polysaccharides" includes, but is not limited to, lipopolysaccharides (LPS), exopolysaccharides (EPS) and *Acinetobacter* polyelectrolyte exopolysaccharide (APE).

Carbon sources which can be employed in culture medium of polysaccharide-producing bacteria include but are not limited to ethanol, ethyl propionate, saturated or unsaturated fatty acids, salts thereof, hydroxylated fatty acids and complex carbon sources such as, for example, petroleum and petroleum fractions. In a preferred embodiment, the carbon source includes fatty acids having from about 10 carbon atoms (C10) to about 20 carbon atoms (C20), salts thereof, alkyl esters and in particular methyl esters thereof, hydroxylated C10 to C20 fatty acids, any combinations thereof as well as complex carbon sources including C10 to C20 fatty acids or derivatives or combinations thereof. Both saturated and unsaturated C10 to C20 fatty acids can be employed. Preferred examples of fatty acids include decanoic, lauric, tridecanoic, myristic, pentadecanoic, palmitic, heptadecanoic and stearic acids. These are abbreviated herein as 11:0 (11 carbon atoms), 12:0 (12 carbon atoms), 13:0 (13 carbon atoms), 14:0 (14 carbon atoms), 15:0 (15 carbon atoms), 16:0 (16 carbon atoms), 17:0 (17 carbon atoms) and 18:0 (18 carbon atoms), respectively. In yet another embodiment of the invention, the carbon source includes alkyl esters and in particular methyl esters derived from the above 11:0, 12:0, 13:0, 14:0, 15:0, 16:0, 17:0 and 18:0 fatty acids. In a further embodiment, the carbon source includes hydroxylated, in particular 2-hydroxyl 11:0, 12:0, 13:0, 14:0, 15:0, 16:0, 17:0 and 18:0 fatty acids.

As used herein, "complex carbon source" refers to mixtures which include but are not limited to hydrocarbons, carboxcylic acids, derivatives and salts of carboxcylic acids, alcohol, such as, for example carbon sources generally used in growing emulsan. Specifically, "complex carbon source" refers to crude oil, petroleum fractions or agricultural oils (e.g., safflower oil).

In a preferred embodiment of the invention, the polysaccharides are obtained from *A. venetianus* strain RAG-1 or from mutants of *A. venetianus* RAG-1. Variants of polysaccharides can also be obtained. Variants include polysaccharides which can be produced from bacteria other than *A. venetianus*. polysaccharides or variants also can be synthesized chemically in the absence of a bacterial cell and used in the methods described herein.

A "mutant" refers to any *A. venetianus* which differs from the nonmutant *A. venetianus*, also referred to as native or wildtype bacterium, in a sequence of the genetic material of the bacterium. The mutant can be the result of a spontaneous mutation or the result of an experimental mutation (e.g., transposon mutagenesis). A mutant differs from the nonmutant by any change in any genetic sequence. For example, the difference in the gene sequence can be the result of a single or multiple base pair changes, an interruption in the genetic sequence, a frameshift mutation, or the random or selective insertion of an exogenous nucleic acid sequence (e.g., transposon, such as Tn10) into the genome of the bacterium. The mutant can have metabolic, physiology or phenotypic differences from the nonmutant which lead to the production and secretion of emulsan analogs.

Lipopolysaccharides

Lipopolysaccharides of the invention are characterized as polyanionic amphiphathic lipoheteropolysaccharides whose main chain or backbone has been reported to include three amino sugars: D-galactosamine, D-galactosaminuronic acid and diamino-6-deoxy-D-glucose. Fatty acids are covalently linked by N-acyl and O-ester bonds to the backbone of the lipopolysaccharide.

Lipopolysaccharides having specific structural features can be prepared and characterized as further described below. For example, manipulation in both the composition and degree of fatty acid substitution can be achieved as described in Gorkovenko et al., Proc. Am. Chem. Soc., Div. Polym. Sci. Eng 72:92-93 (1995), Gorkovenko et al., Can. J. Microbiol. 43:384-390 (1997), (Gorkovenko, et al., Carbohydrate Polymers, 39:79-84 (1999) and Zhang, et al., J. Biol. Macromol. 20: 9-21 (1997), the teachings of which are incorporated herein by reference in their entirety. Lipopolysaccharides other than those specifically described herein also can be prepared by those skilled in the art by following methods known in the art as well as methods described herein.

Studies showing that exogenous fatty acids can be incorporated directly have been reported by Gorkovenko et al., Carbohydrate Polymers, 39: 79-84 (1999), the teachings of which are incorporated herein by reference in their entirety). Gorkovenko et al., (Carbohydrate Polymers 39: 79-84 (1999), the teachings of which are incorporated herein by reference in their entirety), used 0.5% (w/v) .sup.13C.sub.1-palmitic acid and 0.5% acetic acids as cosubstrates and reported an lipopolysaccharide from emulsan wherein GC-MS analysis of the 7475 and 87/88 mass ion pairs showed that 80% of emulsan C 16 fatty acid esters are incorporated intact from the C16 carbon source. Other studies have showed that the percent of C14, C15, C16, C17 and C18 fatty acid esters derived from the corresponding n-alkanoic acids that were mono unsaturated were 10.9, 25.6, 33.5, 69.7 and 84.7%, respectively (Gorkovenko et al., Proc. Am. Chem. Soc., Div. Polym. Sci. Eng. 72. 92-93 (1995); Gorkovenko et al., Can. J. Microbiol. 43:384-390 (1997); Zhang, et al., J. Biol. Macromol. 20: 9-21 (1997), the teachings of which are incorporated herein by reference in their entirety). An aerobic desaturation mechanism (.DELTA.9 desaturase activity) has been reported for emulsan lipopolysaccharide synthesis (Gorkovenko et al., Proc. Am. Chem. Soc., Div. Polym. Sci. Eng. 72:92-93 (1995); Gorkovenko et al., Can. J. Microbiol. 43:384-390 (1997); Zhang, et al., J. Biol. Macromol. 20: 9-21 (1997), the teachings of which are incorporated herein by reference in their entirety). Unsaturated fatty acids of emulsan are believed to be directly synthesized from saturated fatty acids of a carbon source based on .sup.13C.sub.1-labeling experiments. Thus, it is likely that fatty acid supplements in *A. calcoaceticus* RAG-1 cultivations can be incorporated intact to large extents within chain lengths C15 to C18, and that the percent unsaturation is chain length dependent.

Measuring units employed herein to describe the lipopolysaccharide include mole % (also referred to herein as mol % or mole %), as nanomoles per milligram of emulsan or as % w/w. For example, the 10:0 and 16:0 fatty acid content of lipopolysaccharide produced by growing *A. venetianus* RAG-1 in an ethanol carbon source are 2.6 mol % (or 11 nmol/mg) and 23 mol % (or 99 nmol/mg), respectively.

In one embodiment of the invention, the lipopolysaccharide has a total fatty acid content in the range of between about 25 nmol/mg and about 900 nmol/mg lipopolysaccharide. In another embodiment of the invention, the lipopolysaccharide has a fatty acid content in the range of between about 25 nmol/mg lipopolysaccharide and about 9000 nmol/mg lipopolysaccharide. "Fatty acid content" (nmol/mg) refers to the nanomoles (nmol) of fatty acid per milligram (mg) of lipopolysaccharide. The term "Fatty acid content" is used herein interchangeably with the term "fatty acid density."

*Acinetobacter* Polyelectrolyte Exopolysaccharide (APE)

The discovery and isolation of *Acinetobacter* Polyelectrolyte Exopolysaccharide (APE) was the result of the development of a new purification process for emulsan complex. The emulsan complex produced by *Acinetobacter venetianus* RAG-1 has been studied extensively for its ability to stabilize oil-in-water (o/w) emulsions due to its amphiphatic behavior. The amphiphaticity of emulsan makes it useful for biomedical purposes. Therefore, methods of purification capable of obtaining a substantially pure emulsan is needed to avoid complications, such as immune rejection.

In one embodiment of the invention, polysaccharides are produced by growing *A. venetianus* in ethylpropionate, myristic acid (C14:0) or ethanol. As seen in Table 1 the carbon source affects the types and amounts of substituents on the polymer backbone. For example, the level of odd chain length fatty acid groups seen with ethylpropionate is about 12 mole percent 17-carbon chain length, while the use of myristic acid does not yield odd chain length pendant groups.

The existence of two polysaccharides, a high molecular weight component and bacterial lipopolysaccharide, are discussed in Mercaldi et al's Discovery of the Dual Polysaccharide Composition of Emulsan and the Isolation of the Emulsan Stabilizing Component, *Biomacromolecules*, vol. 9, pp. 1988-1996. The terms "high molecular weight" as used herein, refer to having a molecular weight greater than 3 MDa. More preferably, high molecular weight refers to having a molecular weight of at least 3.4 MDa. Even more preferrably, high molecular weight refers to having a molecular weight in the range of about 3.4 MDa to about 4.7 MDa.

Discovering APE was further corroborated by the experiments described in the Examples where the LPS was identified as rough LPS from the cell wall of *A. venetianus*. A purification process was also developed to isolate the high molecular weight polysaccharide component and determine if the high molecular weight polysaccharide was comprised of similar physical properties as emulsan. It was determined that the LPS adequately described most of emulsan physical properties such as molecular weight, surface charge, glycosyl composition and fatty acid composition. Surprisingly, the high molecular weight component termed EPS in the paper (Mercaldi et al's Discovery of the Dual Polysaccharide Composition of Emulsan and the Isolation of the Emulsan Stabilizing Component, *Biomacromolecules*, vol. 9, pp. 1988-1996) and termed APE herein was discovered to share some part of the glycosyl composition and most importantly the o/w emulsion stabilization. In fact, it was reported that APE surpassed emulsan in emulsion stabilization in terms of time elapsed. Surprisingly, the APE was also found to be substantially free of lipid acids.

In the present invention, exopolysaccharides can comprise galactose, glucose or analogs thereof such as 3-O-methylglucose, and 2-deoxy-D-glucose. In the method of the present invention, bacterial produced polymers comprise tri-saccharide repeating units, such as galactosamine, glucosamine, N-acetylgalactosamine or N-acetylglucosamine. The term "saccharide" refers to a sugar or an amino sugar created by adding an amino group to a sugar structure. In the method of the present invention, exopolysaccharides can comprise N-acetylgalactosamine and N-acetylglucosamine. In addition, polysaccharides containing at least two different monomers have been isolated by the method of the present invention. GC chromatograms of the fractionated exopolysaccharides, made with N-acetylgalactosamine or N-acetylglucosamine, demonstrated that a mixture of polysaccharides with high molecular weights including N-acetylgalactosamine or N-acetylglucosamine were produced. Modifications to the method are also known by those skilled in the art using standard techniques based, for example, on the size, molecular weight or charge of the polymer. For example, solubility in the appropriate solvent, such as distilled water or 10% acetic acid can be used. Therefore, using the method of the present invention, lipopolysaccharides and high molecular weight polysaccharides, can be isolated and purified.

As used herein, the term polysaccharide comprises at least one saccharide and can comprise different saccharide subunits. Exopolysaccharide refers to polymers of one or more different saccharides produced microbially by a bacteria and present on the outside of the bacterial cell. Parameters regarding the production of the polysaccharide can be varied. The mole percent of glucose, galactose or saccharide analogs in the polymer can be varied by varying the culture conditions. Culture conditions can also vary the yield of the polysaccharides The present invention relates to polysaccharides. In particular, the invention relates to glucose, galactose and analogs thereof containing exopolysaccharides. In one embodiment of the present invention, a mole percent of glucose, galactose or analogs thereof can be about 1 to about 90% in the exopolysaccharides. In another embodiment of the present invention, the mole percent of galatosamine in the exopolysaccharide can be about 5 to about 65%. In a more particular embodiment of the present invention, the mole percent of galatosamine in the copolymer can be about 14 to about 65%. In still another embodiment, the mole percent of N-acetylgalatosamine in the exopolysaccharide can be about 7 to about 90%. In a more particular embodiment of the present invention, the mole percent of N-acetylgalatosamine in the exopolysaccharide can be about 14 to about 60%.

The exopolysaccharide can also be partially deacetylated. Moreover, the exopolysaccharide can be deacetylated after purification to change the net charge of the polysaccharide. In some embodiments, the EPS can be partially deacetylated, where partially refers to 1%, 5%, 10%, 20%, 30%, 40%, 50%, 60%, 70%, 80% or 90% deacetylated. It can be further hypothesized that the free amines on the EPS can interact with the uronic acid residues on the polysaccharide thereby increasing polymer interactions.

The present invention is also drawn to a method for producing the polysaccharides, i.e. the lipopolysaccharide and the exopolysaccharide. The method of the present invention results in production of polysaccharides wherein glucose, galactose and analogs thereof are present in the exopolysaccharide at a mole percent of at least about 1 to about 90. In one embodiment of the method of the present invention, the glucose, galactose or derivatives thereof is selected from the group consisting of glucosamine, 3-O-methylglucose, N-acetylglucosamine, galactosamine, N-acetylgalatosamine, 2-deoxyglucose and combinations thereof. In another embodiment of the method of the present invention, the resulting exopolysaccharide comprises N-acetylglucosamine and N-acetylgalatosamine. In one embodiment of the method, the mole percent of galactose or analogs in the exopolysaccharide is about 1 to about 90%. In another embodiment of the method, the mole percent of galactose in the exopolysaccharide is about 14 to about 65%. In another embodiment of the method, the mole percent of N-acetylgalatosamine in the exopolysaccharide is about 7 to about 60%.

In one embodiment of the present invention, the polysaccharides can be isolated from a microbe. In a more specific embodiment, the polysaccharides are isolated from supernatant of a bacterial cell. The microbe can be selected from the group consisting of: *Acinetobacter venetianus, Acetobacter xylinum, Agrobacter tumefaciens, Sarcina ventriculi, Rhizobium leguminosarum*, and *Acinetobacter calcoaceticus*. In a preferred embodiment, the bacterial cell is a *Acinetobacter venetianus* RAG-1.

The APE polysaccharide shares many similar qualities with the polysaccharide chitosan. Chitosan is derived from the polysaccharide chitin. Chitosan is the result of the deacetylyation of chitin to produce a polymer that is comprised of predominately glucosamine with a varying degree of N-acetyl glucosamine. Two major problems with chitosan are inherent in the production of the polysaccharides. The first issue is that the parent polysaccharide, chitin, is harvested from the shells of crustaceans. This leads to a high degree of variability in the chitin product with different degrees of molecular weight and chain length. The second problem with chitosan is that it needs to be produced through the chemical modification of chitin in order to remove the acetyl groups to give chitosan its positive charge. This introduces another degree of high variability where the degree of deacetylyation is variable from batch to batch. Another major problem with chitosan is its solubility in aqueous solutions. Chitosan is only soluble in solutions below pH 7 and is only highly soluble in solutions where the pH is less than 5. This leads to some limitations of chitosan for use in aqueous and biological systems. The APE polysaccharide is amphipathic, like chitosan, but does not have the problems that are associated with it. In addition, APE can be modified to be either positively (amine groups) or negatively charged (uronic groups). Moreover, APE is produced by bacteria under controlled conditions, so batch to batch variability is very low and APE is very reproducible. The APE polysaccharide can also exhibit a net positive charge due to deacetylation without the need for chemical modifications and it is soluble throughout the pH range, therefore it can be utilized at physiological pH for potential biomedical applications.

For the polymer production by *A. venetianus, R. leguminosarum, S. ventriculi* and *A. tumefaciens*, growth can be carried out under standard culture conditions, for these organisms, with the exception that glucose, galactose or analogs thereof can also be fed as co-substrates or as sole substrates. Culture conditions for *A. venetianus* are described below in the Examples. *R. leguminosarum* bv. Trifolii, NAU 843 and NA 30 strains (Australian National University) can be grown in nutrient broth for routine culture or in defined media according to Napoli et al., App. Microbiol. 30:123-131 (1975) for the incorporation of sugar analogs. *S. ventriculi* (available from ATCC) can be grown under anaerobic conditions on 2% glucose with or without glucose and grown in the presence of glucose analogs and 2% yeast extract as described by Canale-Parola, Bacteriological Reviews, 34:82-97 (1970). *A. tumefaciens* can be grown (Matthysse et al., J. Bacteriol, 177:1069-1075 (1995)) in the presence of sugar analogs, as described. Cultures can be incubated from about 22° C. to about 37° C. with 0-300 rpm rotary agitation. Varying the speed of the agitation can vary the size of the polymer. Flocculation, or clustering of the bacteria, is an indication of polysaccharide formation. Flocs of the bacterium can be harvested by centrifugation and the polysaccharides can be isolated by additional centrifugation.

Culture conditions can be varied to influence the production of the polysaccharides. pH of the medium can be from about 4 to about 9. Carbon sources present in the medium can also be varied. Carbon sources can include but are not limited to ethanol, ethyl propionate, saturated or unsaturated fatty acids, salts thereof, hydroxylated fatty acids and complex carbon sources such as, for example, petroleum and petroleum fractions. In one embodiment, the carbon source includes fatty acids having from about 10 carbon atoms (C10) to about 20 carbon atoms (C20), salts thereof, alkyl esters and in particular methyl esters thereof, hydroxylated C10 to C20 fatty acids, any combinations thereof as well as complex carbon sources including C10 to C20 fatty acids or derivatives or combinations thereof. In a preferred embodiment, ethanol can be the carbon source.

Purification of LPS and EPS

To purify the high molecular weight polysaccharide (EPS), the degree of hydrophobicity, size, and charge can be exploited. During process development, the major impurities that were identified include but are not limited to DNA, HCP, and LPS. Other capsular or exopolysaccharides as well as the target EPS were observed qualitatively through SDS-PAGE with the modified Alcian Blue staining method.

The efficiency of removal of the impurities at each step of purification can be observed at each step of the method. Because no quantitative assay for the target EPS is currently available, a w/w % of the impurity may not be calculated until the very end of the purification process. At the end of the purification process, a valid w/w % calculation could be made for the amount of impurities. In some embodiments, the EPS can be purified to greater than 60%, 70%, 80%, 90%, 95%, 96%, 97%, 98%, or 99% purity (w/w %).

The exopolysaccharide (EPS), is the polysaccharide which we have termed APE. *A. venetianus* RAG-1 can be grown in a medium known by those skilled in the art. For example, the medium can comprise: $K_2HPO_4$, $KH_2PO_4$, $MgSO_4.7H_2O$, $(NH_4)_2SO_4$, and trace metal solutions comprising: $CaCl_2$, $FeSO_4.H_2O$, $ZnSO_4.7H_2O$, $Na_2MoO_4$, $CuSO_4.5H_2O$, $MnSO_4.4H_2O$ and $CoCl_2.6H_2O$. The culture medium can also be supplemented a carbon source. The carbon source can long chain hydrocarbons, alcohols, fatty acids, and triglycerides. the carbon source includes fatty acids having from about 10 carbon atoms (C10) to about 20 carbon atoms (C20), salts thereof, alkyl esters and in particular methyl esters thereof, hydroxylated C10 to C20 fatty acids, any combinations thereof as well as complex carbon sources including C10 to C20 fatty acids or derivatives or combinations thereof. Both saturated and unsaturated C10 to C20 fatty acids can be employed. Preferred examples of fatty acids include decanoic, lauric, tridecanoic, myristic, pentadecanoic, palmitic, heptadecanoic and stearic acids. These are abbreviated herein as 11:0 (11 carbon atoms), 12:0 (12 carbon atoms), 13:0 (13 carbon atoms), 14:0 (14 carbon atoms), 15:0 (15 carbon atoms), 16:0 (16 carbon atoms), 17:0 (17 carbon atoms) and 18:0 (18 carbon atoms), respectively. In yet another embodiment of the invention, the carbon source includes alkyl esters and in particular methyl esters derived from the above 11:0, 12:0, 13:0, 14:0, 15:0, 16:0, 17:0 and 18:0 fatty acids. In a further embodiment, the carbon source includes hydroxylated, in particular 2-hydroxyl 11:0, 12:0, 13:0, 14:0, 15:0, 16:0, 17:0 and 18:0 fatty acids. Preferably ethanol is the carbon source.

After growth in culture, the cells can be harvested by centrifugation and a supernatant can be collected. Additional centrifugation can be performed to ensure adequate removal of the cells. The supernatant can also be concentrated by methods known in the art. One method of concentration can be by tangential flow filtration (TFF). Preferably, the supernatant can be concentrated to at least 10 times from a starting volume.

The concentrated supernatant can be treated with a denaturant. In a preferred embodiment, the denaturant is guanidine hydrochloride. The denaturant can initiate the precipitation of contaminating elements such as LPS. Optionally, the LPS can be extracted as a precipitate after denaturation of the supernatant.

The supernatant can also be further concentrated. The supernatant can also be exposed to a detergent. For example, Triton X-114 can be used as a detergent. Other detergents can include SDS, CTAB, sodium deoxycholate and nonionic surfactants to dissociate the LPS/EPS complex by way of electrostatic interactions. Treatment of the supernatant with a detergent can also remove contaminating elements such as LPS and hydrophobic proteins. Detergent can be removed from the supernatant by the use of organic solvents such as chloroform and methanol. Optionally, the use of a detergent can be substituted with column chromatography purification. Additionally, chromatography can remove detergent added to the supernatant.

The supernatant can also be subjected to phase extractions known by those skilled in the art to remove contaminating elements. For example, a cloud point phase extraction (TX) induces the EPS into an upper detergent poor phase while a lower detergent rich phase can be discarded that contains the contaminating elements such as LPS and proteins. Repeated extractions can also be performed to further purify the EPS.

In another embodiment, the EPS can be extracted from the supernatant. The supernatant can be treated with a salt to precipitate the EPS. The salt can also aid in removing nucleic acids and contaminating polysaccharides. A preferred example of a precipitating salt can be ammonium salt. In an even more preferred embodiment, EPS can be precipitated with the use of ammonium sulfate. Additionally, the EPS can be extracted by column chromatography. Chromatography methods known by those skilled in the art with knowledge of EPS physical properties, such as size, charge, pH, solubility etc, can be employed. In a preferred embodiment, hydrophobic interaction chromatography column can be used to separate the desired polysaccharide, i.e. EPS or APS, from the supernatant. The pure polysaccharide can be collected and further dialyzed against water to remove any contaminating reagents. The polysaccharide can also be lyophilized using a lyophilizer to yield a substantially salt free product.

Physical and Chemical Properties of APE

APE is a high molecular weight polysaccharide. APE can have a molecular weight greater than 3 MDa. More preferably, APE has a molecular weight of at least 3.4 MDa. Even more preferably APE has a molecular weight in the range of about 3.4 MDa to about 4.7 MDa. The APE is also substantially free of lipid acids.

In the present invention, exopolysaccharides or APE can comprise galactose, glucose, analogs and derivatives thereof such as 3-O-methylglucose, and 2-deoxy-D-glucose. In the method of the present invention, microbe produced exopolysaccharides comprising saccharides, such as galactosamine, glucosamine, N-acetylgalactosamine or N-acetylglucosamine. In a preferred embodiment of the invention, the APE comprises a tri-saccharide repeating unit. The term "saccharide" refers to a sugar or an amino created by adding an amino group to a sugar structure. The tri-saccharide repeating unit can comprise N-acetylgalactosamine and can further comprise N-acetylglucosamine. The EPS of the invention can comprise the one monosaccharide or different monosaccharides. Thus, EPS containing at least two different saccharide groups can be isolated by the method of the present invention. In a preferred embodiment, the trisaccharide repeating unit is →4)α-D-GalpNAc-6-OAc-(1→4)-α-D-GalpNAcA-(1→3)-α-D-QuipNAc4NHb-(1→. In another embodiment the trisaccharide repeating unit has the formula:

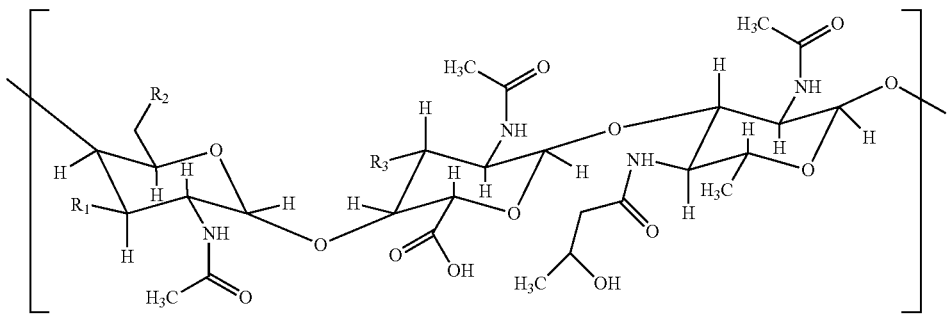

where R1, R2 or R3 can be selected from the group consisting of OH and OAc.

The term "OAc" as used herein refers to acetyl group and can be in the formula: H—CO— or alkyl —CO— group. Preferred acetyl groups can include but are not limited to palmitoyl, lower alkyl, formyl, acetyl, propanoyl, 2-methylpropanoyl, and butanoyl groups.

The structural characteristics of APE classify it as a high molecular weight, zwitterionic, amphiphilic polysaccharide. A polysaccharide with such properties would be a useful candidate for emulsion stabilization. In order to assess the application potential of APE, the intrinsic properties of the polymer were identified. To validate the hypotheses of APE's physical properties, its molecular weight, size, charge, and surface tension were analyzed. Light scattering determined APE to be a high molecular weight exopolysaccharide (~3.4× $10^6$ Da to $4.7 \times 10^6$ Da) with a $R_H$ larger than the $R_g$. The observed increase in $R_H$ over $R_g$ is a result of the perceived radius in solution being greater than the "dry" $R_g$ measurement, indicating that the polysaccharide can absorb water and can possess some rod-like character. Polysaccharides like APE, such as xanthan gum, are neither rod-like nor random coil, but rather can be flexible rods where the polysaccharide displays characteristics from both conformations. The striking feature of the light scattering results was the apparent monosdispersity of the polysaccharide. Polysaccharides of natural origin can polydisperse due to aggregation phenomena and lack of purity which makes molecular weight and size analysis problematic.

The light scattering data consistently demonstrated that APE had a polydispersity of less than 1.1, indicating that the host cell possesses control in polysaccharide production and that the purification process renders APE in a highly pure state. Unlike other bacterial polysaccharide purification processes, the process used for APE produces the polysaccharide with a high degree of purity. In some embodiments, the APE can be purified to greater than 60%, 70%, 80%, 90%, 95%, 96%, 97%, 98%, or 99% purity (w/w %). Typical purification protocols for this class of polysaccharides consist of few steps with the predominant steps being simple alcohol precipitations. This yields a product that has contains contaminating polysaccharides and proteins. To remove contaminating proteins alkaline treatment is usually performed, which can have deleterious effects on the polymer structure. The thorough and mild purification process disclosed herein for APE allows for accurate and detailed examination of the polysaccharide.

The difference between $R_H$ and $R_g$ can be attributed to the functional groups on APE interacting with one and other, which can result in a degree of rigidity. This can be an effect of ionic interactions between polysaccharide chains. From the NMR data it was hypothesized that some of the acetylated amines were deacetylated and could display a positive charge. Titration of the polymer confirmed this hypothesis through calculation that approximately 10% of available amines were deacetylated. In some embodiments, the APE can be partially deacetylated, where partially refers to 1%, 5%, 10%, 20%, 30%, 40%, 50%, 60%, 70%, 80% or 90% deacetylated. It can be further hypothesized that the free amines will interact with the uronic acid residues increasing polymer interactions. APE can also have two pKa values, making APE a zwitterionic polyelectrolyte. More preferably, N-acetyl galactosamine in the APE can be deacetylated and the pKa of APE can be in the range from about 5.5 to about 8.

The degree of the zwitterionic character is dependent on the concentration of deacetylated amines present on the polymer. The majority of the amine functional groups can be linked with either acetyl or 3-hydroxybutyramido groups. These moieties can be hydrophobic and impart an amphipathic character to APE. The 3-hydroxybutyramido group can be more hydrophobic than the acetyl group and it can imparts a greater contribution to polymer amphipathicity. In one embodiment of the invention, the exopolysaccharide can comprise at least one hydrophobic group. In another embodiment of the invention, the tri-saccharide repeating unit of the polysaccharide can comprise at least one hydrophobic group. In yet another embodiment, the hydrophobic group of the polysaccharide tri-saccharide repeating unit can be an O-acetyl group, an uronic acid and a 3-hydroxybutyramido group.

To confirm that APE is an amphiphile, the surface tension of APE in solution was tested. A reduction in surface tension is a result of the water/air interface becoming saturated or close to being saturated with the hydrophobic regions of the polysaccharide. This phenomenon reduces the tension between the water/air interface and confirms an additive as having amphipathic characteristics. APE was demonstrated to be amphipathic since it reduced the surface tension linearly with increasing concentration. The polysaccharide continued to decrease the surface tension to concentrations of about 10 mg/ml. In a preferred embodiment, the exopolysaccharide can be capable of reducing the surface tension of water. In another embodiment, the exopolysaccharide can reduce the surface tension of water below about 70 dynes/cm when APE is at a concentration of about 5 mg/mL in water. APE at pH 7.2 did not exhibit a limit to reduction of surface tension as concentrations increased, indicating that higher concentrations of the polysaccharide can further reduce the surface tension at this pH.

Biophysical Properties of APE

The establishment of APE as an amphiphilic polyelectrolyte suggests that polysaccharide behavior in solution can be dependent on solution temperature, ionic strength, and pH. Initial experimentation was conducted to identify the polysaccharide overlap concentration.

Capillary viscometry was used to identify the intrinsic viscosity, $\eta$ and c*. The value of $\eta$, describes the ability of a polysaccharide to increase the viscosity of a particular solvent at a given temperature. The identification of this parameter can provide insight into the molecular weight, size and shape of the polysaccharide coil. The $\eta$ of APE was shown to decrease with increasing pH. A dramatic decrease was observed in the shift from pH 4.7 to pH 7.2. This effect can be attributed to the transition of the zwitterionic state of the polymer (at pH 4.7) to a decreasing zwitterionic state. At pH 4.7, the free amines were positively charged, while the uronic acid groups were negatively charged, resulting in ionic interactions between the groups. The ionic binding caused a stiffening of the polymer chain and resulted in a more rod-like character, leading to an increase in solution viscosity. This transition was also witnessed with an increase in $R_H$ at pH 4.7 (115 nm) over pH 10 (90 nm). The increase in $R_H$ indicated the presence of a stiffer polymer chain with a larger hydrodynamic volume present. In one embodiment, lowering the pH can increase the viscosity of APE.

In addition to ionic functional groups, APE can comprise hydrophobic groups that can interact with one another resulting in polymer interaction and chain stiffening. The interaction of these groups was identified using the pyrene solublization method for critical aggregation concentration (CAC) determination. The CAC determines the onset of polymer aggregation, by identifying the formation of hydrophobic regions in aqueous solution. CAC represents the concentration at which some of polymer chains start to interact and form hydrophobic regions capable of solublizing hydrophobic molecules. The results showed that the CAC is similar for APE at pH 4.7 and 7.2, but higher at pH 10. This indicates that polysaccharide interactions can be driven by hydrophobic interactions and ionic interactions. Moreover, it was established that APE can form hydrophobic regions capable of solubilizing small hydrophobic molecules in aqueous solution. One embodiment of the invention is directed to APE comprising at least one hydrophobic group. The hydrophobic groups can be an O-acetyl group, an uronic acid and a 3-hydroxybutyramido group attached to the saccharide unit. Preferably, the tri-saccharide repeating unit has at least one hydrophobic group.

The solubilization and viscosity of APE suggest that APE self-assembly can be dependent on concentration and pH. Identification of polymer self assembly was examined using microcalorimetry and circular dichroism. In the microcalorimetry experiments, APE was examined well above c*, the capillary viscometry, since below this critical concentration, no observed transition was observed (data not shown). However, above c*, a marked transition was observed at pH 4.7 and pH 7.2 with no transition occurring at pH 10 (FIG. 8C). The endothermic trough was indicative of an ordered to disordered state transition that has been identified for many polyelectrolytes and amphiphiles. The ordered state in amphiphilic polymers is regarded as a helical association between multiple polymer chains stabilized by an inner core of hydrophobic residues. The disordered state is identified as a random coil or a single chain association to shield hydrophobic residues from the aqueous phase. In an embodiment of the invention, APE can be organized into a multi-stranded helical conformation at pH 4.7 and 7.2 and as a random coil at pH 10.

The lack of spontaneous transition back to a random coid or disordered stated is common for such polysaccharides, since the random coil state has greater entropy than the helical state. Also, the reformation of the helix is an energy intensive process, which is not regarded as spontaneous. However, this process can be reversible as in protein and DNA renaturation under the appropriate solution and time conditions. Further investigation into the thermal transition of the polysaccharide with increasing ionic strength, showed the APE transition at pH 4 disappeared with the addition of salt, while at pH 7.2 an increase in the transition temperature with a decrease in enthalpy was observed. This effect was a result of the polyelectrolyte nature of APE, whereby the creation of a helix involves the formation of an electric double layer that contributes to the overall free energy of the helical state. This increase in free energy leads to a more energetically stable state for the helix and results in an increased transition temperature. The absence of this trend with APE at pH 4.7 can be that the addition of salt positively influences the stability of the helical state. At pH 7.2, the polyelectrolytic character of APE is diminished, since many of the free amines have been electrically satisfied. Therefore, the addition of salt at a neutral pH does not have as pronounced an effect when a weaker electrical double layer is formed. In some embodiments, at least one of a pH, a temperature and a salt concentration/ionic strength of the solution can be varied to obtain a helical APE structure or a random coil APE structure.

The order-disorder transition was further examined using circular dichroism (CD) to examine the effects solution environment has on the conformation of the polysaccharides. The CD spectrum of APE was similar to the spectra of other polymers exemplified with a trough signifying the presence of acetyl chromophore and a peak identifying the presence of carboxyl chromophore. Both groups were shown to be present in APE through NMR analysis. Experiments increasing the ionic strength of the solution appeared to have little effect on the trough. It was also demonstrated that increasing the solution temperature in all samples lead to a decrease in both the peak and trough intensity. This result was an effect of an increased negative character of the carboxyl chiral center and an increased positive character of the acetyl chiral center. Thus in some embodiments, the APE can be a zwitterion, by carrying a negative charge and a positive charge. The APE can also be manipulated to increase negatively charged substituents on the saccharide units through the uronic acid groups. APE can also be positively charged through deacetylation of the amine groups on the saccharide units.

Typically in other polysaccharide systems, the intensity of the trough increases with increasing temperature indicating the movement of the acetyl groups to a more dissymmetric environment and a loss of order. However, the acetyl groups in APE did the opposite. It can be hypothesized that an increase in temperature can shield the acetyl groups more than at lower temperatures and therefore the order-disorder transition is primarily mediated by electrostatic forces rather then hydrophobic interactions. Using the results generated in this report, a model of APE's behavior solution describes how the increase or decrease of an environmental stress affects the order-disorder transition of the polymer. For simplification the ordered state appears as a double helix and the disordered state appears as a random coil. The disordered state can be one polymer strand forming a helix upon itself, which has been observed before with other bacterial polysaccharides. In a preferred embodiment APE solution conditions can be varied to obtain a helical APE structure or a random coil APE structure.

Emulsion Stabilization

Previous experimentation involving the emulsifying potential of APE was exclusively involved with macroemulsion stabilization. Macroemulsions are thermodynamically unstable dispersions containing two immiscible liquids and an additive that acts as a stabilizing force. This type of emulsion is formed through the application of a mechanical force (mixing) to the system. If no additives are present in the system, the emulsion will quickly coalesce and phase separate. In order to slow the rate of coalescence, polymers, such as APE, can be utilized to stabilize the colloidal dispersions. Ideal polymers exhibit the intrinsic properties of surface activity (for favorable polar-apolar interface interactions), electrostatic charge (droplet repulsion) and large molecular weight (steric repulsion). The presence of polymeric additives increases the thermodynamic stability of the emulsion and allows it to exist in a metastable state.

The intrinsic properties for APE indicate its potentially as a polymeric stabilizer. Analysis of its chemical structure reveals hydrophobic and hydrophilic functional groups with charged residues. Based on these results, APE can stabilize emulsions through a combination of steric, electrostatic and amphipathic interactions. The amphipathicity of APE can provide a mode of contact of the polysaccharide with the oil phase. The hydrophobic groups on APE such as but not limited to acetyl and 3-hydroxybutyramido groups, can interact with the apolar oil phase. This can enable the bulk of the polysaccharide to extend into the aqueous medium providing an energetically favorable interface for the oil phase to interact with the aqueous phase. In one embodiment of the invention, APE can increase the thermodynamic stability of a emulsion.

A large portion of the polysaccharide can comprise hydrophilic charged residues that are capable of interacting with the aqueous phase of the emulsion. The charged residues can play an important role in colloidal stability, through electrostatic repulsion of other polymer stabilized oil droplets. This mode of action can decrease the rate of coalescence, and can increase the thermodynamic stability of the system. Since APE is zwitterionic, its ability to stabilize a colloidal dispersion can be dependent on the charge state of the polysaccharide, whereby pH and/or ionic strength can have an effect on the system. At pH values below 3.5 and above pH 8, the charge of the polysaccharide can be net positive and then net negative. Solutions at pH values in between this range can yield zwitterionic molecules. In this state, a polysaccharide comprising free amines and uronic acids can interact with one another leading to an increased rate of coalescence. Amines on the polysaccharide can also be ionically bound to the uronic acid residues before emulsion formation. CD and microcalorimetry have also indicated the polysaccharide can self-associate in this range of pH values.

The solution pH can also influence the viscosity of APE solutions. An increase in solution viscosity can increase the steric stabilization of an emulsion. It was determined that as pH increases, viscosity decreases. More rigid polysaccharides can sterically repel oil droplets better then more flexible or random coil polysaccharides. At pH 10, the random coil state can be predominate with a lower viscosity, while at pH 4.7, the random coil state is minimized and rigid conformations can be present. The increase in polymer rigidity can decrease the rate of coalescence by preventing the free motion of oil droplets in the emulsion. The polysaccharide can also be a surfactant to decrease the surface tension of a solution or emulsion. In a preferred embodiment, APE can be capable of reducing the surface tension of water when APE is at a concentration of about 5 mg/mL in water. APE at pH 7.2 did not exhibit a limit to reductin of surface tension as concentrations increased, indicating that higher concentrations of the polymer can further reduce the surface tension at this pH.

In one aspect of the invention, the APE can be used as a stabilization component. The emulsion stabilization properties of APE have been documented in stabilizing a hexadecane/water emulsion. In another embodiment, APC can stabilize an emulsion for at least 1 day, 2 days, 3 days, 4 days, 5 days, 10 days, 20 days, 1 month, 2 months, 3 months, 4 months, 5 months, 6 months, 7 months, 8 months, 9 months, 10 months, 11 months, 1 year, 2 years, 3 years, 4 years and 5 years. In a preferred embodiment, the APE can stabilize an emulsion for at least 3 months.

Uses

Uses of the polysaccharide of the present invention are numerous. Since it is a amphipathic polysaccharide that is biodegradable it can be used for a vast number of biomedical applications. The uses of the polysaccharide exploit in some manner the polyelectrolytic amphipathic, zwitterionic behavior of the polysaccharide.

The polysaccharide can be formulated to be administered to a host (e.g., mammal) using various routes of administration known in the art. Methods of administration of compositions for use in the invention include, but are not limited to, intradermal, intramuscular, intraperitoneal, intravenous, subcutaneous, intraocular, oral and intranasal. In a preferred embodiment, the route of administration is intramuscular or intraperitoneal. The polysaccharide formulations of the invention can also be administered to the host in combination with other physiologically acceptable medium (e.g., water, buffered saline, polyols such as glycerol, propylene glycol, liquid polyethylene glycol and dextrose solutions).

In some embodiments, APE can be used in drug delivery with nanoparticles, microparticles, hydrogels or emulsions. In other embodiments, APE of the present invention can be used in wound healing by way of hydrogels. In other embodiments, the polysaccharide of the present invention can be used in the development of biodegradable actuators. In other embodiments, APE can be used in stabilizing oil in water emulsions, such as for food uses. In some embodiments, the polysaccharide of the present invention can be used as a vaccine adjuvant. In other embodiments, APE can be used as a component in the development of a tissue engineering scaffold. In other embodiments, APE can be used for therapeutic uses, such as an antibacterial.

Solid lipid nanoparticles (SLN) are a recently developed colloidal system for the encapsulation and controlled release of therapeutic agents. The advantages of colloidal drug delivery systems are high drug loading capacities, drug targeting potential, increased drug bioavailability and minimal invasiveness of administration when compared to other systems. Colloidal carriers can be injected subcutaneously, intraperitonealy, or intravenously and do not have be surgically administered. Some disadvantages of these systems are that they often use toxic organic solvents for production, employ the use of nonbiodegradable constituents, have potentially toxic degradation products and could have scale up issues affecting large scale production. In order to overcome the disadvantages of the other colloidal systems, SLN were formed with biologically safe materials, without the presence of organic solvents or non-biodegradable constituents. One of most important advantages of SLN when compared to its colloidal counterparts is the ease of production. SLN can be formed using established pharmaceutical formulation methodologies such as high pressure homogenization. This process has been used to produce parenteral emulsions and has the ability to be scaled for large scale manufacturing.

The resulting SLN emulsion is a mixture of solid lipid core nanoparticles that is stabilized through the combination of lipophilic and hydrophilic surfactants. The stabilized solid lipid core entraps the drug and increases the stability of the emulsion. The advantages of the solid lipid core is that it prevents diffusional loss of the drug out of the particle, prolongs release of the drug over time and helps to prevent emulsion coalescence. All materials used to form SLN are biologically safe and biodegradable. Examples of commonly used surfactants for SLN development have included lecithins, phospholipids, poloxamers, and bile salts. All lipids to be used must be pharmaceutically approved and have been comprised of mono-, di-, and triglycerides, waxes or fatty acids.

SLN have been used for the encapsulation and controlled release of drugs such as small molecule chemotherapeutics. The advantages of SLN for this purpose are its ability to encapsulate hydrophobic agents in the lipid core and to be passively targeted toward the tumor site. Since the size of SLN can be less than 500 nm, the particles can take advantage of the enhanced permeation and retention (EPR) effect. By exploiting this tumor property, the particles can enter the tumor site through the leaky vasculature and unleash their drug payload. Materials that comprise SLN can impart stealth properties to the particles to evade reticuloendothelial system (RES). SLN can also maintain a long circulating, slow releasing nanocarrier for use in multiple applications, such as chemotherapeutics.

In one embodiment of the invention, a lipid nanoparticle can comprise a therapeutic agent dispersed within a lipid core surrounded by an encapsulating high molecular weight polysaccharide, wherein the polysaccharide has trisaccharide repeating units and a molecular weight greater than 3 MDa. In another embodiment, a therapeutic nanoparticle can comprise a therapeutic agent bound together with a high molecular weight cationic polysaccharide cross-linked with a polyanion. The size of the particle can also be less than 1 micrometer. In another embodiment, the size of the particle ranges from about 500 nm to about 100 nm. More preferably, the size of the particle ranges from about 300 nm to about 50 nm. Additionally, SLN can be larger than 100 nm which is the upper limit for renal clearance. The polysaccharide can also be a polyelectrolytic exopolysaccharide isolated from *Acinetobacter* bacteria. The polysaccharide can further comprise tri-saccharide repeating units and have a molecular weight greater than 3 MDa in an uncross-linked state. The tris-accharide repeating units can also comprise N-acetyl galactosamine, N-acetyl glucosamine or a derivative. The polyanion can also be tripolyphosphate.

In one aspect of the invention, a hydrophobic therapeutic agent can be encapsulated. Examples of a therapeutic agent include, but are not limited to small molecule drugs, anti-tumor agents, anti-angiogenesis agents, antibiotics, proteins, growth factors, antibodies, nucleic acids molecules, carbohydrates, and the like. Growth factors useful in the present invention include, but are not limited to, transforming growth factor-alpha (TGF-α), transforming growth factor-beta (TGF-β), platelet-derived growth factors (PDGF), fibroblast growth factors (FGF), including FGF acidic isoforms 1 and 2, FGF basic form 2 and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-alpha, and TNF-beta. Immunoglobulins useful in the present invention include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Other molecules useful as therapeutic or biological agents include, but are not limited to, growth hormones, leptin, leukemia inhibitory factor (LIF), endostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha.

Embodiments involving amino acids, peptides, polypeptides, and proteins may include any type or combinations of such molecules of any size and complexity. Examples include, but are not limited to structural proteins, enzymes, and peptide hormones. These compounds can serve a variety of functions. In some embodiments, the matrix may contain peptides containing a sequence that suppresses enzyme activity through competition for the active site. In other applications antigenic agents that promote an immune response and invoke immunity can be incorporated into a construct. In substances such as nucleic acids, any nucleic acid can be present. Examples include, but are not limited to deoxyribonucleic acid (DNA), and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787, 567). DNA can be present in vectors of any kind, for example in a viral or plasmid vector. In some embodiments, nucleic acids used will serve to promote or to inhibit the expression of genes in cells inside and/or outside the electrospun matrix. The nucleic acids can be in any form that is effective to enhance its uptake into cells.

An example of a therapeutic agent that has been shown to be successfully encapsulated in SLN was paclitaxel (PTX). PTX has been investigated for use in SLN because it is one of the most potent anti-cancer drugs available, but suffers from poor aqueous solubility (<0.33 µg/ml). Since it is not soluble in aqueous solution, its clinical use has been very problematic. Typically, PTX has been solublized in a 50:50 mixture of Cremophor EL:Ethanol and then intravenously administered to the patient. This solvent system for PTX is very toxic and also confers unpredictable pharmacokinetics to the drug. Due to these issues, the application of the drug has been limited and only used in extreme circumstances. However, SLN can be seen as a possible alternative for the formulation of PTX. Recent studies have shown that SLN can be used to solublize and effectively deliver PTX with a high degree of carrier safety.

The particles can be designed by one skilled in the art. The design can also be adapted from previous work performed by Lee, M.-K. et al (Lee C-, Lee H-, Lee K-. O-palmitoylcurdlan sulfate (OPCurS)-coated liposomes for oral drug delivery. *Journal of Bioscience and Bioengineering*. 2005; 100(3): 255-259), which demonstrated that SLN can successfully encapsulate and release PTX. It was determined that a mixture of trimyristin, a triglyceride, and egg phosphatidylcholine were able to solublize the drug when the lipid was melted. However, if the drug is not able to be solublized in the lipid phase, the formation of SLN is greatly affected. Unsolublized drug crystals can interfere with particle formation, leading to emulsion flocculation and an eventual collapse of the emulsion based system. Therefore, it is critical to be able to solublize the drug in the lipid phase.

In one embodiment, APE can be used to solubilize a therapeutic agent and in the formation of SLN. In a specific embodiment, a lipid nanoparticle comprising a therapeutic agent can be dispersed within a lipid core surrounded by an encapsulating high molecular weight polysaccharide. The high molecular weight polysaccharide can have tri-saccharide repeating units and a molecular weight greater than 3 MDa. In one embodiment, the tri-saccharide repeating units can be N-acetyl galactosamine, N-acetyl glucosamine or a derivative. In a preferred embodiment, the polysaccharide is a polyelectrolytic exopolysaccharide isolated from *Acinetobacter* bacteria. The lipid core can also comprise at least one lipid, such as monoglycerides, diglycerides, triglycerides, waxes and fatty acids.

Solid lipid nanoparticles can be formed by methods known to those skilled in the art. In a preferred embodiment, the hot homogenization method can be used. The particles can be formed in a two step process. The first step can be to form a pre-emulsion of APE with lipid and the therapeutic agent. In a preferred embodiment, the therapeutic agent can be dissolved in the lipid. The lipid can be a monoglyceride, a diglyceride, a triglyceride, a wax and a fatty acid. The lipid solution can further be mixed with an aqueous solution comprising a high molecular weight polysaccharide having trisaccharide repeating units and a molecular weight greater than 3 MDa. In a preferred embodiment, the polysaccharide is a polyelectrolytic exopolysaccharide isolated from *Acinetobacter* bacteria.

After the formation of the pre-emulsion, the hot emulsion can undergo hot homogenization to solidify the lipid core and form the particles. Homogenization can be carried out at an elevated temperature. In a preferred embodiment, the temperature can be above 60 degrees C. The emulsion can further be cooled to form particles having a therapeutic agent dispersed within a lipid core surrounded by the high molecular weight polysaccharide. In one embodiment, the step of cooling the emulsion further comprises solidifying the core lipid. Any insoluble drug or lipid that was not incorporated can be removed from the mixture. Modifications to the method by those skilled in the art can also be incorporated.

The size of the nanoparticles can further be varied and determined. The relative concentrations of lipid and polysaccharide can influence the size of the nanoparticles. In addition, the addition of pressure homogenization to the hot homogenization can also vary the size of the nanoparticles. Higher pressures can yield smaller, compact nanoparticles, whereas lower pressures can yield larger nanoparticles. Determining the size of the nanoparticles can be done by methods known by those skilled in the art. In one embodiment, dynamic light scattering analysis can be used.

SLN nanoparticles can also be stable for extended lengths of time. For example, the SLN nanoparticles can be stable for at least 1 day, 2 days, 3 days, 4 days, 5 days, 10 days, 20 days, 1 month, 2 months, 3 months, 4 months, 5 months, 6 months, 7 months, 8 months, 9 months, 10 months, 11 months, 1 year, 2 years, 3 years, 4 years and 5 years at room temperature. In a preferred embodiment, the SLN are stable for at least 4 weeks at room temperature.

It was observed that the loaded SLN exhibited a greater effect on the cell viability as compared to Cremophor EL solublized PTX and unloaded SLN in the higher concentration ranges (100 ng/ml and 1000 ng/ml). This result demonstrated the loaded SLN could effectively deliver the drug in a more effective manner than the commonly used Cremophor EL carrier. Furthermore, the effect on cell viability of the unloaded system was fairly minimal with the exception of lowest cell viability near 60% at highest simulated concentration of PTX. This decrease in cell viability was attributed to an excessive amount of carrier present in the media. This effect can be avoided if more PTX can be encapsulated in the nanoparticles. Regardless, the reduction in cell viability of the unloaded carrier was shown to higher than the loaded SLN, which signified the drug and not the carrier was exerting the cytotoxic effect on the cells. The results from this experiment indicated that the APE based system has potential for the safe and effective delivery of PTX.

The exopolysaccharide of the invention can be produced and secreted by bacterium and further combined with an antigen for use in the immunization formulations of the invention. One or more exopolysaccharide from mutant bacterium can be mixed or administered with the antigen alone or with the antigen and exopolysaccharide secreted from a nonmutant bacterium. The terms nonmutant, wild type, native or control bacterium are used interchangeably herein to refer to a bacterium that is not a mutant bacterium.

The exopolysaccharide of the invention produced and secreted by mutant bacterium can lead to immune responses (e.g., T-cell and/or B-cell activation and recruitment, antibody production to an antigen) which are similar to, less than or greater than emulsan analogs produced and secreted by nonmutant bacterium cultured under a variety of feeding strategies (e.g., varying fatty acid chain length, varying fatty acid density, fatty acids with varying amounts of saturated bonds).

It is envisioned that the mutants of the invention can be used to produce readily available cellular sources to generate large volumes of exopolysaccharide for use in immunization formulations and methods of stimulating cytokine responses. Clonal populations of mutants can be stored, cultured and exopolysaccharide with consistent properties generated under standards laboratory techniques. Mutants deficient in fatty acid utilization can lead to further 'tailoring' of structural profiles. Mutants can be grown on various carbon sources, such as the carbon sources described above, also resulting in further tailoring of exopolysaccharide.

Thus, another aspect of the invention relates to a method of forming an exopolysaccharide composition for use as an adjuvant, comprising the steps of making a mutant bacterium, screening the mutant bacterium for the production and secretion of exopolysaccharide, wherein the exopolysaccharide secreted from the mutant bacterium is used as an adjuvant or a stimulate.

Thus, the immunization formulation comprising the antigen and exopolysaccharide can be used as a vaccine. A vaccine refers to any immunization formula comprising an antigen and exopolysaccharide described herein which result in immunological prophylaxis.

The exopolysaccharide from nonmutant or mutant bacterium can be administered alone or simultaneously to a host with or without an antigen. Alternatively, or additionally the antigen and exopolysaccharide can be administered separately to the host. For example, the host can be administered the antigen followed by administration of the exopolysaccharide. Likewise, the host can be administered the exopolysaccharide followed by administration of the antigen. One of skill in the art would be capable of determining a suitable administration strategy.

The exopolysaccharide or immunization formulation of the invention can be administered to the host (e.g., mammal) using various routes of administration known in the art. Methods of administration of compositions for use in the invention include, but are not limited to, intradermal, intramuscular, intraperitoneal, intravenous, subcutaneous, intraocular, oral and intranasal. In a preferred embodiment, the route of administration is intramuscular or intraperitoneal. The exopolysaccharide and immunization formulations of the invention can also be administered to the host in combination with other physiologically acceptable medium (e.g., water, buffered saline, polyols such as glycerol, propylene glycol, liquid polyethylene glycol and dextrose solutions).

The amount, optimum concentration and dose of exopolysaccharide, and antigen in the immunization formulation needed to elicit an immune response or immunodulation of the host can be determined empirically, according to procedures well known to one of skill in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

This invention is further illustrated by the following examples which should not be construed as limiting. The following experiments were performed to demonstrate various aspects of the invention.

Example 1

Materials and Methods

Strain and Culture Conditions

*Acinetobacter venetianus* RAG-1 (ATCC 31012) was obtained from the American Type Culture Collection. Unless otherwise noted all chemicals and media components were purchased from Fisher Scientific or Acros Organics.

The strain was grown in a defined medium which consisted of (per liter of water): $K_2HPO_4$, 17 g; $KH_2PO_4$, 7.26 g; $MgSO_4 7H_2O$, 0.5 g; $(NH_4)_2 SO_4$, 4 g; and 3 ml of a trace metal solution which contained (per 100 ml): $CaCl_2$, 36.8 mg; $FeSO_4.H_2O$, 60.4 mg, $ZnSO_4.7H_2O$, 42.2 mg, $Na_2MoO_4$, 69.6 mg; $CuSO_4.5H_2O$, 62.4 mg; $MnSO_4.4H_2O$, 59.4 mg; $CoCl_2.6H_2O$, 78.8 mg. The $MgSO_4.7H_2O$ stock solution was sterilized separately and then added to the culture medium.

Cultures grown for development of a purification process were according to the previous literature using 1% (w/v) ethanol as the carbon source (13). Each culture was produced in five 4 L baffled flasks each containing 1 L of media and incubated at 30° C. for 72 hours with agitation at 250 rpm. Five separate cultures were grown in order to evaluate the effectiveness of the purification process.

Emulsan Purification

Emulsan was purified according to the previously outlined methods (FIG. 1A) (Johri, A. K.; Blank, W.; Kaplan, D. L. *Applied Microbiology and Biotechnology* 2002, 2-3, 217-223). After 72 hours of cell growth, the culture was centrifuged at 10,000×g and 4° C. for 30 min using a Sorvall RCSB SuperSpeed Floor Centrifuge (Thermo Scientific, Waltham, Mass.). The cells were discarded (CS) and emulsan was precipitated by the addition of ammonium sulfate (AS) to obtain a 40% saturated solution. The precipitated product was isolated by centrifugation and then extracted three times with hot phenol at 65° C. (P). The polysaccharide containing aqueous phase was collected, dialyzed to remove any remaining phenol, and lyophilized to yield a final product.

Exopolysaccharide Purification

Figure 1B:
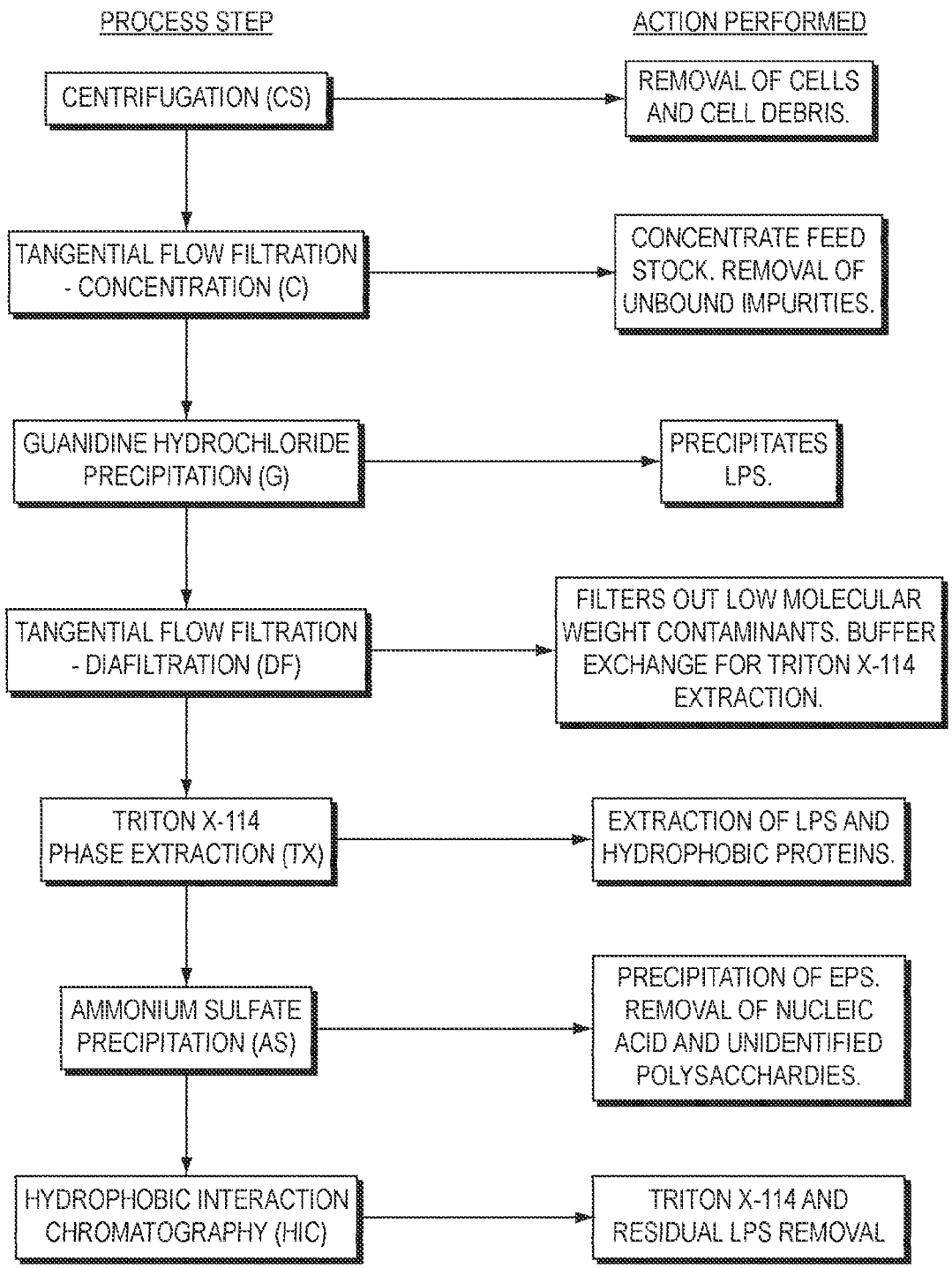

The exopolysaccharide was purified according to the flowsheet in FIG. 1B. After 72 hours of culture growth, cells were removed by centrifugation (CS). The culture was centrifuged at 10,000×g for 30 min at 4° C. as described above. The supernatant was collected and then centrifuged again at the same conditions to ensure complete removal of all the cells.

The supernatant was concentrated (C) by tangential flow filtration (TFF) in a Centramate system (Pall BioPharmaceuticals, East Hills, N.Y.) using a Pall Omega Membrane with a surface area of 0.1 $m^2$ and a molecular weight cutoff of 50 kDa. The fluid was driven by a Watson Marlow 600 RE4 Series peristaltic pump (Watson Marlow, Wilmington, Mass.) at a crossflow of 1.60 L/min and a transmembrane pressure of 22 psi at room temperature. The supernatant was concentrated 10-fold from a starting volume of 5 L to a final volume of 500 ml.

The concentrated supernatant was then treated with an equal volume of 6M guanidine hydrochloride (G). This resulted in a cloudy white precipitate was then removed by centrifugation at 10,000×g and 4° C. for 30 min. The pellet was discarded and the supernatant was subjected to centrifugation twice more.

The resulting supernatant was then concentrated two-fold to 500 ml using the aforementioned TFF system, under the same conditions as described for concentration. When the volume was at 500 ml, the solution was diafiltered (DF) 10 times with 20 mM sodium acetate, 150 mM sodium chloride, and 20 mM EDTA, pH 4.75 to prepare the sample for the ensuing Triton X-114 phase extraction.

A 5% (w/v) solution of untreated Triton X-114 was prepared at 4° C. using the resulting diafiltrate as the solvent. This solution was mixed for 1 hour at 4° C. until a clear micellar solution was apparent and then subsequently centrifuged for 1 hour at 10,000×g at 4° C. The pellet was discarded and the supernatant was saved.

The supernatant was then subjected to a cloud point phase extraction (TX). The sample was heated in a water bath heater to 40° C. for 1 hour and then centrifuged for 30 min at 10,000×g at 25° C. The upper detergent poor phase was collected while the lower detergent rich phase was discarded. To the aqueous phase, Triton X-114 was added to generate a 5% (w/v) solution, mixed for 1 hour at 4° C., heated at 40° C. for 1 hour and then centrifuged for 30 min at 10,000×g at 25° C. This was repeated one more time and then repeated with a 2% (w/v) Triton X-114 extraction to give a total of four extractions.

Ammonium sulfate was added to the extract and mixed for 1 hour at 4° C. to generate a 40% w/v solution that resulted in a precipitate (AS). The precipitate was then removed by centrifugation at 10,000×g for 30 min at 4° C. The supernatant was discarded and the precipitate was resuspended back to its original volume in 20 mM bis-tris propane (Sigma, St Louis, Mo.), 1 M sodium chloride, pH 9.5 to prepare the sample for chromatography.

A Phenyl FF HiSub 16/10 hydrophobic interaction chromatography column (GE Healthcare, Piscataway, N.J.) was used in flowthrough mode to separate the polysaccharide from the remaining Triton X-114 and LPS (HIC). The column was connected to a FPLC Chromatography System (GE Healthcare, Piscataway, N.J.) with UV detection at 280 nm for monitoring Triton X-114 removal. A 20 ml injection of the resuspended polysaccharide precipitate was injected onto the column that was equilibrated with the aforementioned bis-tris buffer at room temperature. The column was washed with 50 ml of equilibration buffer at a linear velocity of 149 cm $h^{-1}$. The polysaccharide was collected starting at 6 ml to 27 ml of the flowthrough. After collecting all of the polysaccharide, the column was cleaned using 30% isopropanol in order to remove all the bound Triton X-114. The pure polysaccharide was collected, dialyzed against water using a 3,500 kDa MWCO membrane (Spectrum Laboratories, Rancho Dominguez, Calif.) and lyophilized yielding a salt free pure product.

Lipopolysaccharides Purification

LPS was extracted from RAG-1 cells discarded in the exopolysaccharide purification by the phenol-chloroform-petroleum ether (PCP) extraction with minor modifications as previously described (Brade, H.; Galanos, C. European *Journal of Biochemistry* 1982, 122, 233-237). After the cells were collected from centrifugation they were washed once with distilled water, once with ethanol, twice with acetone, and once with ethyl ether. Once washing was complete, the cells were dried under a stream of nitrogen. The mass of cells was taken and then brought up in 90% phenol to produce 0.5 g of cells/ml of phenol solution. The cells were then warmed to 65° C. and homogenized for one minute to ensure a fine suspension of cells. After stirring, the cells were then subjected to chloroform and heptane. The LPS was the extracted at 65° C. and the cells were removed. The cells were again subjected to the same treatment in order to increase the yield of LPS.

Chloroform and heptane were removed in a RV 05 basic 2-B rotary evaporator (IKA, Wilmington, N.C.) at 40° C. The remaining LPS in phenol was precipitated with small amounts of water added dropwise. Once a precipitate was seen the addition of water was stopped and the solution was centrifuged at 5000×g for 10 min. The LPS precipitate was washed twice with 80% phenol, followed by seven washes with acetone.

After washing with acetone, the LPS was solubilized in MilliQ water by drop wise addition of a 0.5 M EDTA solution until the LPS became soluble. Once solubility was obtained, the LPS was dialyzed against water using dialysis membrane tubing with a MWCO of 3,500 kDa. After 8 water changes the LPS was lyophilized.

Quantitative Assays

All assays were performed at the end of every purification step in order to monitor the purification process of the exopolysaccharide. The assays were performed at the very end of purification for the emulsan purification except for the LAL assay due to the exorbitantly high values of LPS present in the purified emulsan.

Proteins were identified by the method of Bradford (Bradford, M. M. *Anaytical. Biochemistry* 1976, 248-254). DNA was measured using the Quant-IT High Sensitivity dsDNA kit (Molecular Probes, Eugene, Oreg.). Triton X-114 was monitored using UV 280 nm on the FPLC system.

LPS contamination was monitored with the TBA assay for the measurement of 2-keto-3-deoxyoctonoic acid (Karkhanis, Y. D.; Zeltner, J. Y.; Jackson, J. J.; Carlo, D. J. *Analytical Biochemistry* 1978, 85, 595-601) with the purified LPS from *Acinetobacter venetianus* RAG-1 used as a standard. LPS was measured by the Pyrogent Plus Gel Clot Assay (Lonza, Walkersville, Md.) at the end of purification for the EPS. The TBA assay was used due to the large amount of LPS present in all of the purification steps before the Triton X-114 extraction step. The extremely high levels of LPS in these early purification steps caused the gel clot assay to be very inaccurate since significant dilutions needed to be produced. After the Triton X-114 phase extraction the TBA was unsuccessful in determining the amount of LPS as the levels dropped below the sensitivity limit of $1 \times 10^5$ EU/ml. LAL was attempted for the Triton X-114 and ammonium sulfate steps but it proved to be ineffective due to the contaminating Triton X-114. Attempts to precipitate the polysaccharide from the Triton X-114 using organic solvents also proved to be unsuccessful. Therefore, the calculation of the LPS in these purification steps could not be performed. After chromatography the LPS could be satisfactorily quantified using the LAL gel clot assay since all of the Triton X-114 was removed and the EPS exhibited no inhibition of the assay.

EPS detection Using Modified Alcian Blue Staining

The polysaccharide and lipopolysaccharides were monitored by SDS-PAGE using an 8-16% Tris-Glycine gel (Invitrogen, Carlsbad, Calif.) with a modification of the Alcian Blue staining method for acidic polysaccharides (Dams-Kozlowska, H.; Kaplan, D. L. *Applied and. Environmental. Microbiology* 2007, 12, 4020-4028) that would allow for staining of cationic polysaccharides. After gel electrophoresis, the gel was washed in 200 ml of deionized water with water changes every 10 minutes for 1 hour. After washing, the gel was stained with a solution of 0.1% (w/v) of Alcian Blue 8GX (Sigma, St. Louis, Mo.) in 40% ethanol/20 mM sodium acetate, pH 4.75 for 1 hour. The stain was discarded and the gel was destained overnight in a 40% ethanol/60% 20 mM sodium acetate pH 4.75 solution.

Fatty Acid Composition

The fatty acids putatively covalently coupled to the EPS, LPS, and emulsan were removed after purification and analyzed by GC-MS to establish composition and degree of substitution using previously published methods (Gorkovenko, A.; Zhang, J.; Gross, R. A.; Belsky, I.; Gutnick, D. L.; Kaplan, D. L. *Carbohydrate Polymers* 1999, 1, 79-84; Belsky, I.; Gutnick, D. L.; Rosenberg, E. FEBS Letters 1979, 1, 175-178). Briefly, starting material of 25 mg of each polysaccharide was used and dissolved in 90% methanol/10% water 0.45M potassium hydroxide solution. The mixture was then heated for 6 hours at 100° C. with vortex agitation every 30 minutes to prevent scorching of precipitated material. After the saponification procedure, the resulting fatty acids were converted to fatty acid methyl esters (FAMES) using the methanol-sulfuric acid method (*Advances in Lipid Methodology—Two*; Christie, W. W.; Oily Press: Dundee, Scotland, 1993; pp 69-111). The fatty acids were dissolved in 1 ml of toluene in a VariClean 40 ml pre-cleaned glass vial fitted with a Teflon top (Pierce, Rockford, Ill.). To the toluene mixture, 2 ml of a 1% (w/v) solution of concentrated sulfuric acid in dry methanol was added. The mixture was incubated overnight in a 50° C. water bath to allow the reaction to go to completion. After the incubation, a 5% (w/v) sodium chloride solution was added and the FAMES were extracted with two 5 ml washes of hexane. The hexane was washed with 4 ml of a 2% (w/v) potassium carbonate solution in water and then dried over anhydrous sodium sulfate. The salt was removed by filtration with coarse filter paper (Whatman, Florham Park, N.J.) and the hexane was evaporated over a stream of nitrogen.

The resulting FAMES were dissolved in an appropriate amount of carbon tetrachloride to produce a 1 mg/ml solution. The sample was then subjected to GC/MS using a Shimadzu QP5050A GC/MS with FID detection (Shimadzu Scientific Instruments, Columbia, Md.) A splitless injection of 1 μl of the FAMES were injected onto a RTX_XLB column (30 m, 0.25 um, 0.25 mm) (Restek, Bellefonte, Pa.) at a linear velocity of 43.8 cm/s. The temperature at the time of injection was 100° C., and held for 2 min before increasing at a rate of 4.0° C./min until it reached 320° C. A 37 FAME standard kit (Supelco, Bellefonte, Pa.) was used as a standard and used to develop a calibration curve to quantify the amount of fatty acids present in all the samples. The resulting spectra were compared to the standard and an internal library connected with the NIST Chemistry WebBook.

Glycosyl Composition of the EPS and LPS

Glycosyl analysis of the EPS and LPS samples were independently analyzed at an outside vendor (M-Scan Inc. West Chester, Pa.) utilizing the following method. A portion of the sample was dissolved in ultra high quality water to produce a 0.5 mg/ml solution. Two aliquots of sample solution (200 μl each, equivalent to 100 μg of the supplied sample were taken and 10 μg of Arabitol (internal standard) was added to each. Two standard mixtures containing 10 μg each of Fucose, Xylose, Mannose, Galactose, Glucose, N-Acetylgalactosamine, N-Acetylglucosamine and N-Acetylneuraminic acid, and two tube reagent blanks all containing all containing Arabitol (10 μg) as internal standard were also prepared. The resulting mixtures were lyophilized.

Following lyophilization the sample aliquots were hydrolyzed (1.5M Trifluoroacetic acid (TFA), 2 hr at 120° C.) alongside one blank and standard, and lyophilized. The hydrolyzed and non-hydrolyzed sample aliquots, blanks and standards were methanolysed (1N methanolic/HCl, 16 hours at 80° C.) and the products were lyophilized, TMS-derivatized and analyzed by GC-MS.

For GC-MS, a 1 μA aliquot of the derivatized carbohydrate samples dissolved in hexane, were analyzed by GC/MS using a Perking Elmer Turbomass Gold mass spectrometer (Perkin Elmer, Waltham, Mass.) with integrated capillary gas chromatograph using helium as a carrier gas. The injector temperature was 95° C. and the program was carried out as follows: 1 min at 90° C. then 25° C./minute to 140° C., then 5° C. minute to 220° C., then 10° C./minute to 300° C., finally held at 300° C. for 5 minutes. Spectra were complied and analyzed against standards and an internal library.

Emulsion Stabilization

An emulsion stabilization assay was performed on the purified EPS, LPS and emulsan. A 5 mg/ml solution of each polysaccharide in 2.7 ml of 20 mM sodium phosphate buffer pH 7.2 was prepared and 300 µl of hexadecane was added to give a concentration of the hydrophobic phase (φ) a 10% (v/v) concentration. The solution was shear dispersed using a Branson Digital Sonifier (Branson Instruments, Danbury, Conn.) for 30 seconds at 15% amplification. The resulting emulsions were allowed to stand at room temperature for 6 weeks. After the allotted time interval photographs were taken of the emulsions for visual analysis. A stable emulsion is indicated by a single turbid phase. An unstable emulsion is indicated by the observed phase separation of packed turbid phase from the bulk aqueous phase coupled with the separation of the hydrophobic phase from the packed turbid phase. The presence of phase separation in this manner is indicative of an unstable emulsion (*The Colloidal Domain: Where Physics, Chemistry, Biology and Technology Meet*; Evans, D. F.; Wennerstrom, H.; Wiley-VCH: New York, 1999; pp 539-597).

Anti-EPS Antibody Development

Purified EPS was linked to Keyhole Limpet Hemocyanin (KLH) with p-Azidobenzoyl hydrazide (ABH) according to manufacturer's specifications (Pierce, Rockford, Ill.). Five female BALB/c inbred mice (Charles River Laboratories, Andover, Mass.) were immunized intraperitonealy with 200 µl of vaccine formulation, comprised of 100 µg of EPS-KLH complex and 100 µl Complete Freund's Adjuvant. The animals were boosted 3 weeks after the primary immunization with an identical antigen concentration and 100 µl of Incomplete Freund's Adjuvant. Serum was collected at 7-day intervals starting at 7 days after the boost.

Western Blot

Samples from the EPS purification scheme, purified LPS and purified emulsan were separated by SDS-PAGE using an 8-16% Tris-Glycine gel and transferred to a nitrocellulose membrane according to the manufacturer's specifications (Invitrogen, Carlsbad, Calif.). The membrane was blocked in 5% BSA/PBS/Tween 20 overnight. The membrane was then incubated for 1 hour with a 1:1000 dilution of anti-EPS serum raised as described above or an anti-emulsan rabbit serum (Quality Controlled Biochemicals, Hopkinton, Mass.). After three 15 minute washes with PBS/Tween 20 wash, the membrane was incubated with a 1:5,000 dilution of an alkaline phosphatase-conjugated goat anti-murine or anti-rabbit Ig (whole molecule) (Pierce, Rockford, Ill.) at 4° C. The blot was developed with a BCIP/NBT solution according to manufacturer's instructions (Pierce, Rockford, Ill.). The blot was then imaged using Syngene GeneSnap software. (Syngene, Frederick, Md.)

Example 2

Emulsan Complex Identification

Since its discovery in 1979, emulsan has been described as a complex polyanionic lipopolysaccharide, which could be produced as a crude emulsan or a protein-free apoemulsan (Zuckerberg, A.; Diver, A.; Peeri, Z. *Applied and Environmental Microbiology* 1979, 3, 414-420). Emulsan was the product resulting from ammonium sulfate precipitation, whereas apoemulsan was the outcome of the hot phenol extraction. Emulsan has consistently been shown to have high levels of protein impurities, on the order of 12-17% by weight. However, apoemulsan was previously considered to be pure, with impurities less than 1% (w/w %) (Zuckerberg, A.; Diver, A.; Peeri, Z. *Applied and Environmental Microbiology* 1979, 3, 414-420).

Contrary to that previous work, recent studies in our laboratory have indicated that apoemulsan (from now on known as emulsan) is not a single homogenous polysaccharide, but likely a complex of two or more components, with LPS as a major contaminant. In light of this finding, we pursued detailed isolation and characterization of the components of the emulsan complex. With this goal in mind, emulsan was purified according to the protocol previously used and fractions at the end of each step were analyzed for comparison with the fractions generated during the new purification process. SDS-PAGE gels using Alcian Blue staining for polysaccharides were used to monitor each step of the purification scheme (for the emulsan purification scheme. M-SeeBlue Plus2 Marker (Invitrogen, Carlsbad, Calif.), CS—Cell Supernatant, AS—40% Ammonium Sulfate Precipitation, P-Hot Phenol Extraction, LPS—Pure lipopolysaccharide). A high molecular weight smear has been previously attributed to emulsan, while a low molecular weight band has not been identified. The pure lipopolysaccharide was run for comparison to low molecular weight bands present in the final product.

At the end of purification, the presence of two distinct polysaccharide species was observed, a high molecular weight smear at approximately 250 kDa, previously attributed to emulsan (Nakar, D.; Gutnick, D. L. *Journal of Bacteriology* 2003, 3, 1001-1009) and a low molecular weight band centered at 6-14 kDa, which has not been previously identified. When the various fractions of the new purification process were compared on the gel to the purified R-LPS from the bacterium, the low molecular weight band was identified as the Rough (R) LPS from the *A. venetianus* cell membrane.

Quantification of LPS in the purified emulsan preparation was conducted with the TBA assay. The results of the TBA assay indicated that LPS represented at least 80% of the of the purified emulsan preparation. The high molecular weight polysaccharide (now termed exopolysaccharide (EPS)) comprised about 19% (w/w %) of the emulsan complex (Table 1). These results demonstrate that emulsan is not a single molecule, but instead a polymer complex representing approximately 19% EPS, and 81% LPS.

TABLE 1

Mass and weight percent of total purified complex of impurities present in the phenol purified emulsan complex. An impurity is defined as being host cell protein (protein), lipopolysaccharide (LPS), and DNA. The EPS content was determined by mass balance versus the calculated impurities.

|  | mass (µg/mg of emulsan) | weight % |
| --- | --- | --- |
| protein | 4.84 | 0.48 |
| LPS | 808 | 80.8 |
| DNA | 0.104 | 0.01 |
| total impurities | 813 | 81.3 |
| EPS | 187 | 18.7 |

Example 3

Exopolysaccharide Purification

The impetus for the discovery of the complex nature of emulsan was the development of a new purification process for emulsan, with the primary focus to eliminate the hot phenol extraction for the purification scheme. Work had commenced on the purification process concurrently with the complex identification studies. However, once the discovery of the LPS impurity was realized the development of a purification process to isolate the high molecular weight component became the highest priority.

In order to purify the high molecular weight component (EPS), the degree of hydrophobicity, size, and charge were exploited in order to realize this goal. During process development, the major impurities that were identified and monitored throughout the purification process included DNA, HCP, and LPS. Other capsular or exo-polysaccharides as well as the target EPS could not be adequately quantified but rather were observed qualitatively through SDS-PAGE with the modified Alcian Blue staining method.

In the gel, the EPS is indicated by the high molecular weight smear present at approximately 250 kDa while the LPS is indicated by the low molecular weight band present between 6 kDa and 14 kDa. It is not clear whether other bands present represent other polysaccharides, or rather LPS and or EPS with modified mobility due to the presence of various contaminants. The disappearance of the LPS and other polysaccharides (OPS) can be observed as the purification process progresses. After the last purification step, the LPS was not observed and a single high molecular weight polysaccharide species was present.

the precipitated material it was elucidated that the material comprised of approximately 81% (w/w %) LPS. Due to the high molecular weight nature of the LPS, it could either be in the S-type or aggregates of R-type. The over abundance of this type of LPS was shown to inhibit any accurate calculation of protein using several protein assays including Lowry, BCA and Bradford. Therefore, the final mass removal percentage was taken from the results after the guanidine hydrochloride precipitation step.

As seen in Table 2 & 3, the EPS was purified to approximately 98% (w/w %) at the end of the purification scheme. All contaminants were significantly reduced, with LPS displaying the largest decrease by mass with seven orders of magnitude mass reduction. A large part of this can be attributed to the Triton X-114 extraction due to the disappearance of the LPS from the Alcian Blue stained gel when comparing the diafiltration fraction with the Triton X-114 fraction.

Each purification step had an important role in removing contaminants from the EPS. The TFF steps were effective in removing impurities that were not associated with high molecular weight aggregates. The more important aspects of the TFF steps were to reduce the total volume, concentrate the product and exchange the buffer for further purification steps. The unorthodox guanidine hydrochloride precipitation step between concentration and diafiltration was discovered unintentionally when attempting to denature proteins to dissociate

TABLE 2

Mass reduction of LPS, protein and DNA throughout the course of the EPS purification process (n = 5 purification runs).

| purification step | total protein (mg) | removal (% weight) | total DNA (mg) | removal (% weight) | total LPS (EU) | removal (% weight) |
|---|---|---|---|---|---|---|
| CS | 320.95 ± 56.7 | n.d. | 30.48 ± 7.9 | 0.00 ± 0.0 | $3.92 \times 10^{10} \pm 8.1 \times 10^9$ | 0.00 ± 0.0 |
| C | 153.28 ± 14.4 | n.d. | 21.07 ± 4.1 | 27.03 ± 13.7 | $2.17 \times 10^{10} \pm 3.2 \times 10^9$ | 43.32 ± 12.8 |
| G | 328.44 ± 49.8 | 0.00 ± 0.0 | 19.97 ± 3.8 | 30.81 ± 12.6 | $1.68 \times 10^{10} \pm 2.9 \times 10^9$ | 55.38 ± 12.2 |
| DF | 173.73 ± 30.1 | 46.88 ± 8.7 | 16.75 ± 3.4 | 41.93 ± 10.3 | $1.21 \times 10^{10} \pm 1.6 \times 10^9$ | 67.95 ± 8.7 |
| TX | 30.35 ± 7.0 | 90.80 ± 1.6 | 5.78 ± 1.2 | 77.82 ± 8.5 | $<1.00 \times 10^5$ | 99.99 ± 0.0 |
| AS | 10.50 ± 2.4 | 96.78 ± 0.9 | 0.26 ± 0.1 | 99.08 ± 0.2 | $<1.00 \times 10^5$ | 99.99 ± 0.0 |
| HIC | 4.28 ± 1.3 | 98.68 ± 0.5 | 0.19 ± 0.1 | 99.33 ± 0.3 | $6.21 \times 10^3 \pm 1.0 \times 10^2$ | 99.99 ± 0.0 |

[a]n = five purification runs.

The efficiency of removal of the impurities at each step of purification is displayed in Table 2. Since there is currently no quantitative assay for the target EPS a w/w % of the impurity could not be calculated until the very end of the purification process. At the end of the purification process a valid w/w % calculation could be made for the amount of impurities (Table 3).

TABLE 3

Final values for contaminants at the end of purification for EPS. Values are reported in a weight percent (w/w %) and as a mass ratio for clarity. Sample size (n = 5 purification runs).

| | |
|---|---|
| yield per batch (mg) | 185.2 ± 9.52 |
| purity (w/w %) | 98 ± 0.11 |
| protein (w/w %) | 1.98 ± 0.08 |
| protein (μg/mg) | 19.76 ± 0.76 |
| DNA (w/w %) | 0.08 ± 0.01 |
| DNA (ng/mg) | 788.40 ± 123.33 |
| LPS (w/w %) | $2.33 \times 10^{-6} \pm 7.48 \times 10^{-7}$ |
| LPS (EU/mg) | 44 ± 14 |

Some discrepancies in the quantitative tables can be attributed to the presence of what is hypothesized to be free smooth (S-type) LPS or LPS aggregates present before guanidine hydrochloride precipitation. By performing a TBA assay on aggregates during diafiltration. This proved ineffective due to a white precipitate that formed during the guanidine addition. It closely resembled the by-product removed during the 40% ammonium sulfate cut according to the SDS-PAGE gels in the emulsan purification procedure. Silver staining gels indicated the substance to be primarily S-type (smooth) LPS or LPS aggregates, since it covered a higher molecular weight range (20-200 kDa) and was shown to be extracted in an R-type-specific LPS extraction procedure performed in this work (data not shown).

The mechanism of precipitation can be electrostatic interaction of the guanidine cation which has three positive charges and the negative charges of LPS. This interaction causes an aggregate that precipitates. It was noted that R-type LPS did not appear to be removed in this step, which could indicate that is likely bound to the EPS.

After the guanidine step, approximately $1 \times 10^7$ EU/ml LPS contamination remained, which is greater than that present in high density culture supernatants from *E. coli* (Petsch, D.; Anspach, F. B. *Journal of Biotechnology* 2000, 97-119). The high levels of LPS can be attributed to the unique property of the *Acinetobacter* species to release 60% of their LPS to the culture media (Brade, H.; Galanos, C. *European Journal of Biochemistry* 1982, 122, 233-237). At this point in the purification process, it was believed that the LPS was bound to the EPS. When other purification methods failed to dissociate the complex and adequately remove large amounts of LPS, such as chromatography and salt precipitation, detergents were examined. The use of SDS, CTAB and sodium deoxycholate to dissociate the LPS/EPS complex by way of electrostatic interactions failed to achieve sufficient separation. It was hypothesized that the interaction of the EPS to the LPS was stronger than any interaction the detergents could have had with either polysaccharide. A different class of surfactants, non-ionic, were then attempted to dissociate the EPS/LPS interaction after investigating the work performed on the purification of exopolysaccharides using Triton X-114 phase separation (Adam, O.; Vercellone, A.; Paul, F.; Monsan, P. F.; Puzo, G. *Analytical Biochemistry* 1995, 225, 321-327).

The Triton X-114 phase extraction proved to be highly effective. Unlike the other detergents, the Triton X-114 phase extraction dissociated the LPS from the EPS by way of hydrophobicity at elevated temperatures. The elevated temperature (40° C.) aided in weakening the interactions between the two polysaccharides. This effect then allowed the LPS to be extracted from the aqueous phase to the hydrophobic detergent phase. The EPS does not migrate to the hydrophobic detergent phase indicating its high degree of hydrophilicity.

The Triton X-114 phase extraction also provides a means to extract copious amounts of protein from the system as well. At the time of the Triton X-114 step the process fluid has been treated with 3M guanidine hydrochloride and then subsequently diafiltered to an acidic buffer. The guanidine hydrochloride treatment therefore partially denatured all proteins and the sudden removal of the salt through diafiltration led to improper refolding of the proteins creating hydrophobic protein aggregates. These aggregates were then able to be removed to the detergent phase of the extraction. Table 2 displays a 54% (w/w) reduction of protein after Triton X-114 treatment, thus validating the effectiveness of the three steps (G, DF, TX) in order to reduce protein.

While the Triton X-114 phase extraction has been shown in this work to effectively remove LPS from the EPS, the removal of the remaining detergent has posed an additional challenge (Adam, O.; Vercellone, A.; Paul, F.; Monsan, P. F.; Puzo, G. *Analytical Biochemistry* 1995, 225, 321-327; Salek-Ardakani, S.; Stuart, A. D.; Arrand, J. E.; Lyons, S.; Arrand, J. R.; Mackett, M. Cytokine 2002, 1, 1-13; Bordier, C. *The Journal of Biological Chemistry* 1981, 4, 1604-1607). In other reports, the detergent was removed using organic solvents such as chloroform and methanol (Adam, O.; Vercellone, A.; Paul, F.; Monsan, P. F.; Puzo, G. *Analytical Biochemistry* 1995, 225, 321-327). This proved unsuccessful in the present case and was also undesirable as one of the goals of the purification procedure was to avoid the use of organic solvents. After nucleic acid was removed using the ammonium sulfate precipitation, HIC was utilized to eliminate the remaining detergent.

Initially, HIC was performed with acidic (pH 4.75) or neutral (pH 7.40) pH which did not completely remove the Triton (data not shown). However, when the pH was increased to 9.50, the Triton was eliminated, along with the residual LPS remaining after the Triton X-114 extraction step. The efficacy of this step may be explained by the remaining LPS becoming dissociated from the EPS at pH 9.5 in the presence of the residual Triton X-114. At that pH, both molecules carry a net negative charge. The addition of 1 M sodium chloride aids in the dissociation of the molecules by repelling any electrostatic interactions between the two polysaccharides. LPS and the Triton X-114 bound to the fatty acids of the LPS and free in solution were then free to bind to the stationary phase of the column, while the EPS was allowed to flow through the column. In order to maximize the binding capacity for Triton, the Phenyl FF resin was selected over more hydrophobic resins due to the high degree of ligand density and thus high binding capacity for hydrophobic molecules.

The behavior of the EPS in the column demonstrated again its high degree of hydrophilicity. The EPS showed no binding to the column even when the mobile phase consisted of 1 M ammonium sulfate or 4 M sodium chloride, which are common hydrophobic binding inducing salts for HIC (Queiroz, J. A.; Tomaz, C. T.; Cabral, J. M. S. *Journal of Biotechnology* 2001, 2, 143-159). After chromatography, the EPS was present in a highly pure state with approximately 98% (w/w) purity. The amount of LPS present in the final product was measured at 44 EU/mg, which would allow for an approximately 8 mg dose according to the USP guideline of 350 EU/dose (Grandics, P. *Pharmaceutical Technology* 2004, 4, 26-32).

Example 4

Structural Comparison Between the Polysaccharides and Explanation of the Emulsan Complex'S Physical Properties and Mechanism of Formation After the EPS was purified, it had to be compared to LPS and emulsan in order to elucidate to which polysaccharide, the LPS or EPS, gave the reported properties of emulsan. SDS-PAGE mobility and molecular weight have already been discussed previously in this manuscript. However, other properties that defined emulsan structurally and functionally such as glycosyl and fatty acid composition had to be compared.

To begin comparison and to illustrate that the EPS and the LPS are two distinct biomolecules that are complexed to form emulsan, western blots analysis was conducted. The blots were performed at every step of the purification scheme developed for the EPS, pure emulsan and pure LPS. One of the blots was developed using the antibody raised against the EPS and the other blot was developed using the antibody developed against emulsan. When the anti-EPS antibody was used, the low molecular weight bands of the LPS fraction were not observed, indicating that the antibody did not recognize LPS. When the anti-emulsan antibody was employed, the high molecular weight bands were visualized along with the low molecular weight bands. In this blot the LPS fraction was now observed along with the low molecular weight bands in the emulsan fraction.

These results demonstrate that the anti-emulsan antibody was developed for a complex of EPS and LPS. The anti-EPS antibody showed no affinity for the LPS, therefore exemplifying the high degree of purity present in the final EPS fraction and that the LPS and EPS are different polymers. In the anti-EPS blot, the high molecular weight component of the emulsan fraction was weakly developed. The explanation for this is that the high molecular weight component was present in low amounts when compared to the LPS in the emulsan complex. This corroborates the data displayed earlier that LPS is the dominant polysaccharide in the complex.

The polyelectrolytic behavior of EPS was also determined by applying an electrical voltage to a 2% (w/v) solution of the EPS in 20 mM sodium phosphate buffer pH 7.2. The voltage was supplied by a power supply with an attached anode and cathode outputs. Once the voltage was applied to the solution, the solution proceeded to "climb" up the cathode. The results hold promise for the development of the EPS as a "smart" material for use in the developing of actuators for biodegradable electrical products.

Further work was then conducted to structurally identify and compare all three polysaccharides. The fatty acid profiles of all of the three polysaccharides, emulsan, LPS, and EPS, were examined (Table 4). The fatty acid profile of the LPS matches that of emulsan, while fatty acids were not present in the EPS. This indicates that the emulsan fatty acid profile was due to LPS contamination and did not represent covalently-linked acyl chains attached to the high molecular weight polysaccharide (Belsky, I.; Gutnick, D. L.; Rosenberg, E. *FEBS Letters* 1979, 1, 175-178; Gorkovenko, A.; Zhang, J.; Gross, R. A.; Kaplan, D. L. *Carbohydrate Polymers* 1999, 1, 79-84; Gorkovenko, A.; Zhang, J.; Gross, R. A.; Allen, A. L.; Kaplan, D. L. *Canadian Journal of Microbiology* 1997, 4, 384-390). (1, 27, 28). Other literature has noted the presence of these fatty acids in LPS from *Acinetobacter* and other bacterial species, especially 3-hydroxylated fatty acids (Caroff, M.; Karibian, D. *Carbohydrate Research* 2003, 2431-2447).

TABLE 4

Fatty acid composition of the polysaccharides. The fatty acids are represented by the percentage of weight as compared to all fatty acids present and as the percentage of weight for the entire polysaccharide. For the EPS no fatty acids were detected.

| polysaccharide | fatty Acid | mole % |
| --- | --- | --- |
| LPS | decanoic acid | 3.07 |
|  | dodecanoic acid | 16.18 |
|  | 2-hexadecenoic acid | 3.24 |
|  | 2-hydroxydodecanoic acid | 26.03 |
|  | 3-hydroxytridecanoic acid | 51.48 |
| emulsan | decanoic acid | 2.74 |
|  | dodecanoic acid | 9.06 |
|  | 2-hexadecenoic acid | 2.28 |
|  | 2-hydroxydodecanoic acid | 23.46 |
|  | 3-hydroxytridecanoic acid | 62.46 |
| EPS | none present | none present |

Unlike the fatty acid profile, the glycosyl composition of emulsan was not solely attributed to the LPS. The glycosyl composition of the polysaccharides can be seen in Table 5. The glycosyl profile of the LPS indicated the presence of D-glucose and D-glucosamine with D-glucose being the dominant sugar. The EPS contains N-acetyl galactosamine (GalNac) and N-acetyl glucosamine (GlcNac) with GalNac as the major sugar. Yield after hydrolysis proved to be low, but with increasing acid strength a reduction in the levels of aminosugars was observed.

TABLE 5

Composition of the LPS and EPS polysaccharides according to GC-MS analysis. All masses of monosaccharides are given in μg of sugar detected per μg of hydrolyzed polysaccharide.

| polysaccharide | monosaccharide composition (μg/μg sample) | | |
| --- | --- | --- | --- |
|  | Glc | GlcNac | GalNac |
| LPS | 0.11 | 0.04 | 0.00 |
| EPS | 0.00 | 0.02 | 0.12 |

Glc-Glucose,
GlcNac-N-Acetyl glucosamine,
GalNac-N-acetyl galactosamine.

The original monosaccharide identity work with emulsan reported the presence of three primary sugars, D-glucose, D-galactosamine, and 2-amino-2-deoxyhexuronic acid (Zuckerberg, A.; Diver, A.; Peeri, Z. *Applied and Environmental Microbiology* 1979, 3, 414-420). Glucose and galactosamine were present in the LPS and EPS respectively, however the uronic acid sugar was not detected. Two potential causes for this discrepancy can be the hydrolysis conditions and the detection methodology. The hydrolysis conditions in this work were not as stringent as the ones in the original emulsan composition. The conditions were 5M hydrochloric acid at 100° C. for 30 min (Zuckerberg, A.; Diver, A.; Peeri, Z. *Applied and Environmental Microbiology* 1979, 3, 414-420) which would have led to a greater degree of hydrolysis, but could have also degraded hydrolyzed sugars, potentially skewing the results. The 1.5M trifluoroacetic acid hydrolysis used in this work provided a more gentle reaction and mitigated the degree of destruction of the hydrolyzed sugars (Merkle, R. K.; Poppe, I. In *Methods in Enzymology*; Academic Press: New York, N.Y., 1994; Vol. 230, pp 1-15).

The detection methods employed in the original emulsan paper (paper chromatography) were less sensitive than the method presented here (GC-MS) (Merkle, R. K.; Poppe, I. In *Methods in Enzymology*; Academic Press: New York, N.Y., 1994; Vol. 230, pp 1-15). The use of paper chromatography could lead to improper identification of the monosaccharides while the GC-MS provides a more precise sugar identification method. However, the outlined GC-MS method is not absolute and future work will be conducted potentially utilizing more definitive techniques such as NMR or high performance anion exchange chromatography coupled with a pulsed amphoteric detection (HPAEC-PAD) to fully elucidate the composition and structure of the EPS reported here.

Other physical properties of emulsan attributable to LPS are the molecular weight, surface charge, and low solubility in aqueous media. LPS can form elaborate vesicle structures that can exceed 1,000,000 Da that are aided by the presence of divalent cations in aqueous solutions (Petsch, D.; Anspach, F. B. *Journal of Biotechnology* 2000, 97-119). Prior work has demonstrated the presence of vesicles being produced by the RAG-1 strain (Leahy, J. G.; Khalid, Z. M.; Quintero, E. J.; Jones-Meehan, J. M.; Heidelberg, J. F.; Batchelor, P. J.; Colwell, R. R. *Canadian Journal of Microbiology* 2003, 9, 569-575). The supplementation of the culture media with $Mg^{2+}$ provides the LPS with an adequate amount of divalent cations to form these vesicle structures. Coupled with the EPS, these vesicles probably led to the reported molecular weight of 1,000,000 Da. Our attempts to determine the molecular weight of emulsan by static light scattering (SLS) or size exclusion chromatography (SEC) were unsuccessful, due the presence of these vesicles (data not shown). Previous work determined the molecular weight by viscometry (Zuckerberg, A.; Diver, A.; Peeri, Z. *Applied and Environmental Microbiology* 1979, 3, 414-420) and not by SEC or SLS, a method which can be skewed by the presence of aggregates. Thus we conclude based on the Alcian Blue stained gels that the LPS is in the range of 6-14 kDa and the EPS is in the range of 200-250 kDa.

The presence of significant content of LPS in the purified emulsan preparation provides a clear explanation to the low solubility of the complex in aqueous media. If no divalent cations were present, the LPS would not form vesicle structures and would be soluble. This is supported by the increased solubility of the emulsan complex in the presence of EDTA (data not shown). In the presence of divalent cations, R-type LPS is found to precipitate in aqueous solutions. This observation, supported with the fact that LPS was extracted with a procedure developed for the purification of only R-type LPS, indicates that R-type LPS comprises the major contaminant for EPS in the emulsan preparation.

Figure 2:
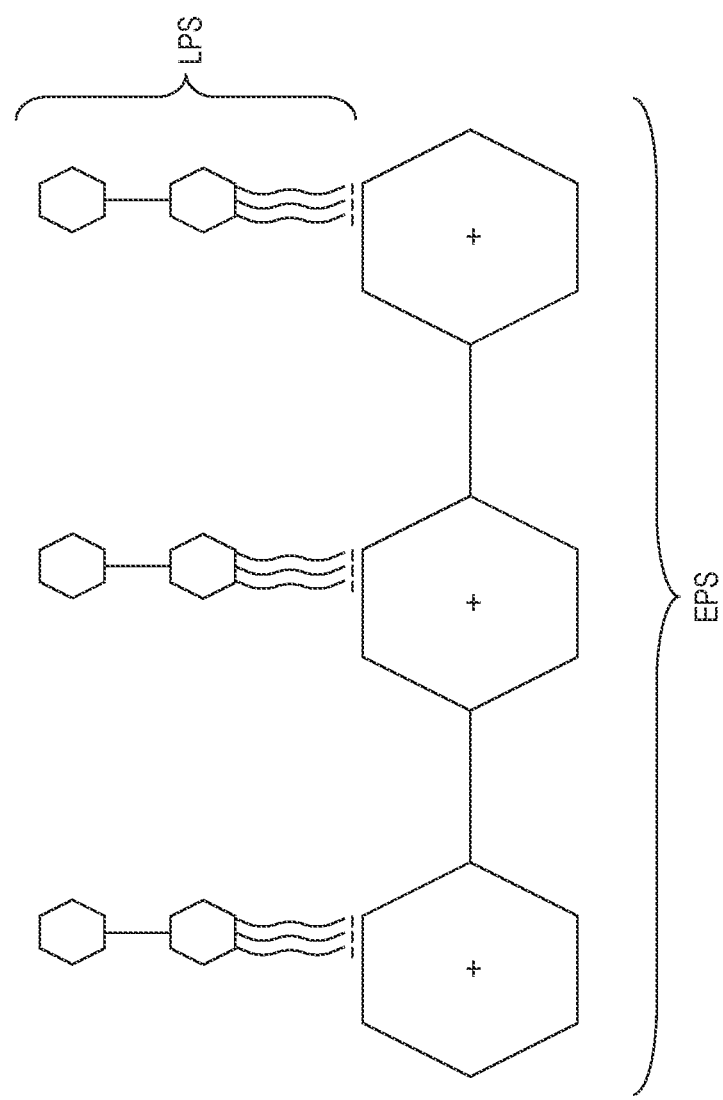
FIG. 2 shows a diagram for the association of LPS with the EPS in solution. The EPS has a net positive charge at this pH while the LPS is negatively charged. The fatty acids on the lipid A portion, designated by the curved black lines is the negative charge dense region that will interact with the free amines that are present on the EPS. The resulting electrostatic interaction provides an explanation for the EPS being present with the LPS at the end of the phenol extraction in the emulsan purification procedure.

The determination of LPS to be R-type provides an explanation of why the emulsan complex exhibits a high negative charge, as well as a methodology for formation. R-type LPS displays a negative charge due to the presence of free carboxylic acid groups, fatty acids and phosphate groups present on the lipid A portion. The EPS is not known to contain any acidic monosaccharides, but does contain N-acetyl saccharides which, when deacetylated, carry net positive charges due to the free amine. There is some degree of deacetylation present due to the solubility of the EPS in aqueous solutions, its high degree of hydrophilicity as observed during the HIC purification step and preliminary work using ion exchange chromatography as a purification step (data not shown). During cultivation, the media is kept at pH 7.2, giving the LPS a negative charge (due to the lipid A) whereas the EPS will have a positive charge (from deacetylated saccharides). Based on these conditions we hypothesize that the emulsan complex is formed through electrostatic interactions (FIG. 2). This complex is expected when performing purification of LPS preparations with phenol based solvents (Raetz, C. R. H. *Annual Review of Biochemistry* 1990, 129-170). Purified LPS is frequently contaminated with cationic impurities such as polyamines, which in this situation will be the deacetylated GalNac rich EPS.

After the physical and structural properties of LPS, EPS and emulsan were assessed the final and most significant property of emulsan to be analyzed was its ability to stabilize o/w emulsions. Since this property of the emulsan complex is its most defining property (Bach, H.; Berdichevsky, Y.; Gutnick, D. *Applied and Environmental Microbiology* 2003, 5, 2608-2615; Gutnick, D. *Research in Microbiology* 1997, 6, 519-521; Kim, P.; Oh, D.; Kim, S.; Kim, J. *Biotechnology Letters* 1997, 5, 457-459; Zhang, J.; Lee, S.; Gross, R. A.; Kaplan, D. *Journal of Chemical Technology and Biotechnology* 1999, 8, 759-765), it was important to assess the stabilization properties of the LPS and the EPS and compare it to emulsan. Each preparation (emulsan, LPS, & EPS) was subjected to the same emulsion formation mechanism and the resulting o/w emulsions were observed over a 6 week interval. All emulsions were created through sonication simultaneously and allowed stand for 6 weeks until comparison. A stable emulsion is indicated by a single turbid phase present in the vial. An unstable emulsion is indicated by the formation of two phases with a clear oil phase present on top of a packed turbid phase.

After the allotted time period the EPS sample continued to stabilize the shear-dispersed emulsion. The emulsan and LPS fractions had exhibited coalescence and phase partitioning. This result indicates that these two polysaccharides (emulsan and LPS) cannot stabilize an emulsion in the long term. The results clearly indicate that the EPS is the stabilizing agent in the emulsan complex. In previous literature, the mechanism for emulsion stabilization was thought to be based upon the purported amphipathic behavior of the biomolecule. The work presented here clearly demonstrates that the EPS which does not contain any fatty acids is able to stabilize emulsion stabilizing behavior. The emulsion stabilizing mechanism of the EPS can be an electrostatic and steric stabilization mechanism similar to that exhibited in chitosan preparations (Del Blanco, L. F.; Rodriguez, M. S.; Schulz, P. C.; Agulló, E. *Colloid and Polymer Science* 1999, 11, 1087-1092).

Example 5

NMR Analysis and Structure Identification

The APE polysaccharide structure was determined using the $^1$H and $^{13}$C NMR spectroscopic methods of 1D $^1$H and $^{13}$C with the 2D COSY, TOCSY, NOESY, and ge-HSQC experiments. Analysis was conducted through examination of first the $^1$H and $^{13}$C spectra and then these results were compared to the more robust 2D techniques in order to render a structure. Furthermore, to accurately elucidate the structure, native polymer was compared to deacetylated polymer.

The native APE 1H spectrum contained six anomeric proton resonances, two of which 5 were incompletely resolved, with chemical shifts in the range of 4.6 to 5.5 ppm (Table 6). The peaks at 2.1 ppm suggested methyl groups of the O-acetyl functional group origin, while the peaks at 2.0 ppm indicated methyl groups of the N-acetyl functional group origin in acetamido sugars. The peak at 1.24 ppm was assigned to the methyl hydrogen atoms of the 3-hydroxy butyramido group of C4 of residue C. The peak at 1.12 ppm was assigned to the methyl hydrogen atoms of a 6-deoxy sugar.

The $^{13}$C NMR spectrum of the native APE contained six carbonyl signals in the range of 174 to 176 ppm (Table 6). These peaks confirmed the presence of three N-acetyl groups, one O-acetyl group, one uronic acid, and one additional group which was identified as the 3-hydroxybutyramido group at C4 on residue C (Table 6). Further analysis identified the six peaks in the range of 98 to 102 ppm as anomeric carbon atoms. Two CH2OH groups in the range of 62 to 65 ppm and four N-substitutes carbon atoms in the range of 52-58 ppm were also observed. The absence from the $^{13}$C NMR spectrum of any signals for non-anomeric sugar ring carbons in the region below 81.0 ppm indicated the pyranosidic nature of the monosaccharides.

TABLE 6

NMR chemical shifts of native APE polysaccharide in D2O at 50° C. 1H and 13C NMR chemical shifts are given with reference to internal standard of (TSP) at −0.017 ppm and −0.18 ppm, respectively.

| Residue Atom | Galp NAc (Aa*) ppm | Galp N (Ad**) ppm | Galp NAcA (B) ppm | Quip NAc4NHb*** (Cd**) ppm | Quip NAc4NHb*** (Ca*) ppm |
|---|---|---|---|---|---|
| H1 | 5.42 | 5.39 | 5.24 | 4.82 | 4.71 |
| H2 | 4.23 | 4.21 | 4.3 | 4.16 | 4.14 |
| H3 | 4.1 | 4.07 | 3.94 | 4.07 | 4.09 |
| H4 | 4.01 | 3.99 | 4.4 | 3.71 | 3.73 |
| H5 | 4.1 | 4.06 | 4.08 | 4.32 | 4.33 |
| H6 | 4.21 | 3.7 | — | 1.12 | 1.12 |
| H6' | 3.9 | 3.56 | — | — | — |
| C1 | 100.52 | 100.3 | 99.6 | 100.98 | 101.18 |
| J$_{(HC)}$ | 177.4 Hz | 177.8 Hz | 172.6 Hz | 168.6 Hz | 173.0 Hz |
| C2 | 52.99 | 52.99 | 52.17 | 57.72 | 57.72 |

TABLE 6-continued

NMR chemical shifts of native APE polysaccharide in D2O at 50° C. 1H and
13C NMR chemical shifts are given with reference to internal standard of (TSP)
at −0.017 ppm and −0.18 ppm, respectively.

| Residue Atom | Galp NAc (Aa*) ppm | Galp N (Ad**) ppm | Galp NAcA (B) ppm | Quip NAc4NHb*** (Cd**) ppm | Quip NAc4NHb*** (Ca*) ppm |
|---|---|---|---|---|---|
| C3 | 75.46 | 75.46 | 71.5  | 75.39 | 75.39 |
| C4 | 79.66 | 79.66 | 77.78 | 57.98 | 57.98 |
| C5 | 69.36 | 69.36 | 74.58 | 69.94 | 69.94 |
| C6 | 64.14 | 62.76 | —     | 19.48 | 19.48 |

*Acetylated form of APE,
**"d" - O-Deacetylated form of APE,
***side chain of QuipNAc4Hb C1(177.4), C2 (47.9), C3(67.8), C4(25.15), H2(2.42, 2.32), H3(4.14), H4(1.24) ppm.

Figure 12A:
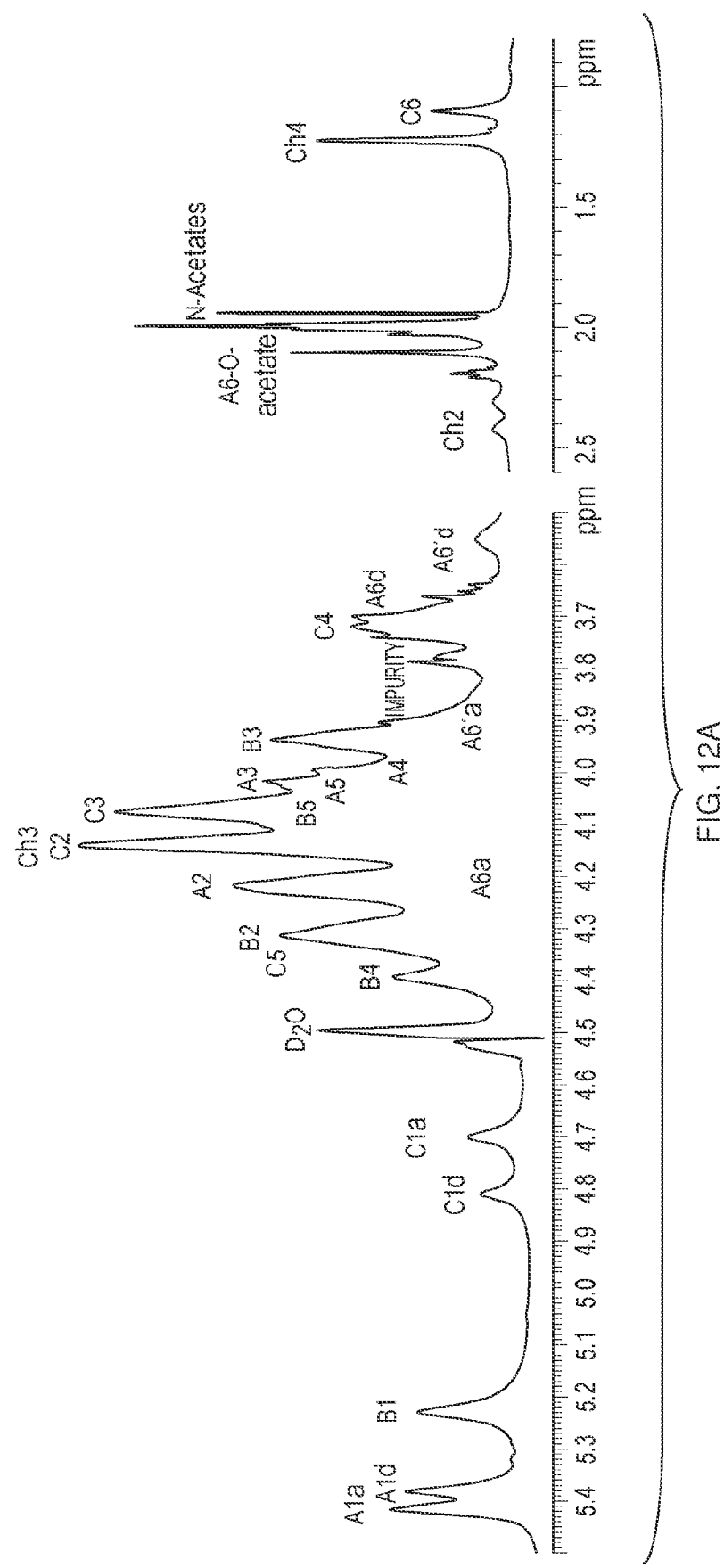
Figure 12B:
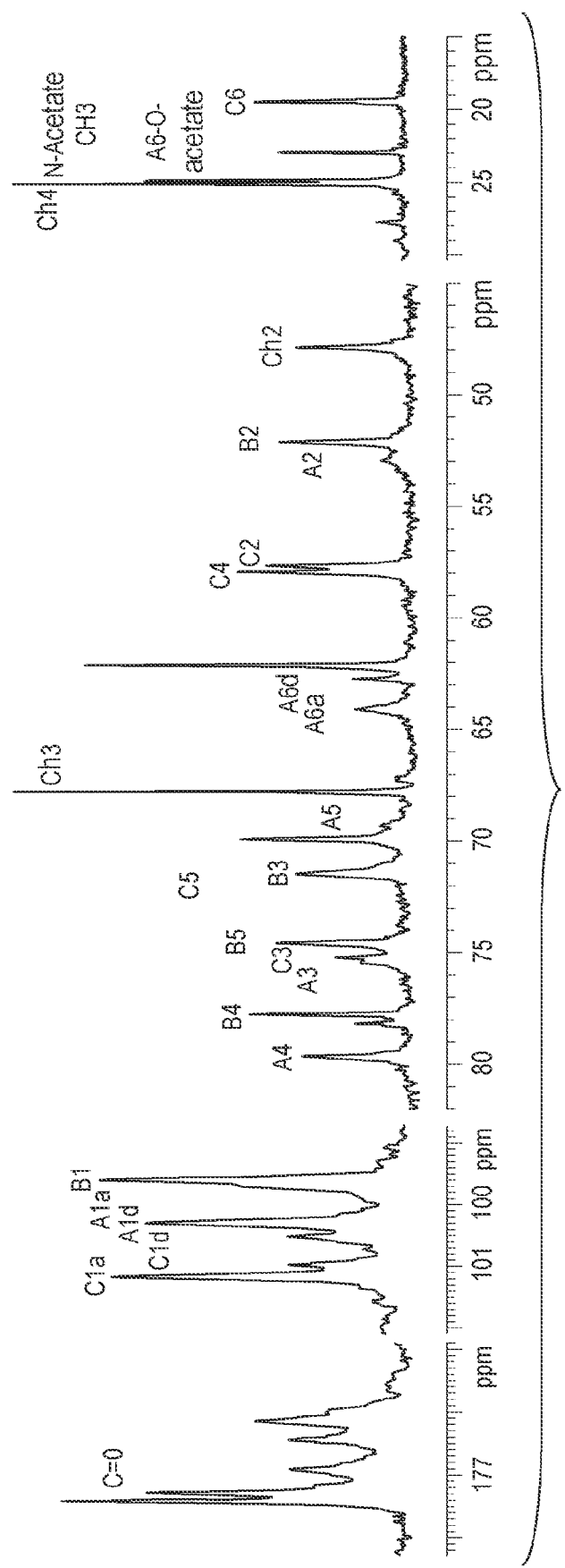

The $^1$H and $^{13}$C NMR spectra of APE were analyzed after polysaccharide deacetylation (FIGS. 12A-B). The major feature of the $^1$H spectrum was three anomeric protons with chemical shifts of 4.82, 5.24, and 5.39 ppm. Major features present in the $^{13}$C spectrum were five peaks in the 174-176 ppm (carbonyl carbon) region, three signals in the range of 98 to 102 ppm for anomeric carbons, and one CH$_2$OH at 62.76 ppm. The analysis of the spectra of the native and deacetylated polymer was determined to be typical of a regular polysaccharide with a linear trisaccharide repeating unit. To further identify the monosaccharide structure and polymer linkage, 2D NMR spectra experiments were performed. Complete $^1$H assignments of native and deacetylated APE were made from 2D DQF-COSY and TOCSY experiments (Table 6). From the DQF-COSY (Table 7), starting from each anomeric proton (A1, B1, or C1) (Table 6), most of the $^1$H spin systems in each sugar residue were able to be assigned. The 2D TOCSY further confirmed these assignments (data not shown). Complete $^{13}$C assignments of native and deacetylated APE were made from 2D ge-HSQC experiments (Table 6). In deacetylated APE, the assigned anomeric proton resonances at 4.82, 5.24, and 5.39 ppm showed correlations to directly bonded carbon resonances in the chemical shift range of 98 to 102 ppm. This was characteristic of anomeric carbon atoms in covalently linked monosaccharide residues, confirming the presence of three monosaccharide residues in the repeating unit.

TABLE 7

NOE correlations of native APE polysaccharide in D2O at 50° C.

| Residue | Initial position ppm | Intra residue ppm | Inter residue ppm |
|---|---|---|---|
| Galp NAc (Aa*) | A1a 5.42 | A2a (s), A5a (s) 4.23  4.10 | B4 (m), B3 (m), B2 (w) 4.40  3.94  4.30 |
| Galp N (Ad**) | A1a 5.42 | A2d (s) A5d (s) 4.21  4.07 | B4 (m), B3 (m), B2 (w) 4.40  3.94  4.30 |
| Galp NAcA (B) | B1 5.24 | B2(s) B3(m) 4.30  3.94 | C3(s) 4.09 |
| Quip N4NHb (Cd**) | C1d 4.82 | C2d (s) C3d(w), 4.16  4.07 | A4d (s) 3.99 |
| Quip NAc4NHb (Ca*) | C1a 4.71 | C2a (s) C3a(w), 4.14  4.09 | A4a (s) 4.01 |

*Acetylated form of APE,
**Deacetylated form of APE.

Analysis of 1D spectra (Table 1) with correlations from the 2D spectra, was able to identify the three monosaccharide spin systems which were assigned to residues of (A) 6-Oacetyl-2-acetamido-2-deoxy-α-Dgalactopyranose (α-D-GalpNAc-6-OAc), (B) 2-acetamido-2-deoxy-α-D-galactpyranosyluronic acid (α-D-GalpNAcA), and (C) 2-acetamido-4-(3-hydroxybutyramido)-2,4,6-trideoxy-α-Dglucopyranose (α-D-QuipNAc4NHb). The last sugar might also be described as a quinovose derivative, as that is an alternative name for 6-deoxy glucose. The sequence of the monosaccharide repeating units was also determined from the 2D NOESY spectra (Table 7). NOE correlations between protons A1 and B4 and B3 indicated a 1-4 linkage of residue A to B. Anomeric B1 corrolated to C3 indicated a 1→4 linkage of residue B to C, and anomeric C1 correlated to A4, A3, and A5, indicated a 1→4 linkage of residue C to A. From this, the sequencing of the polysaccharide APE was determined to be -α-D-GalpNAc-6-OAc-(1→4)-α-DGalpNAcA-(1→3)-α-D-QuipNAc4NHb-(1→4).

Example 6

Surface Charge Identification

Figure 3:
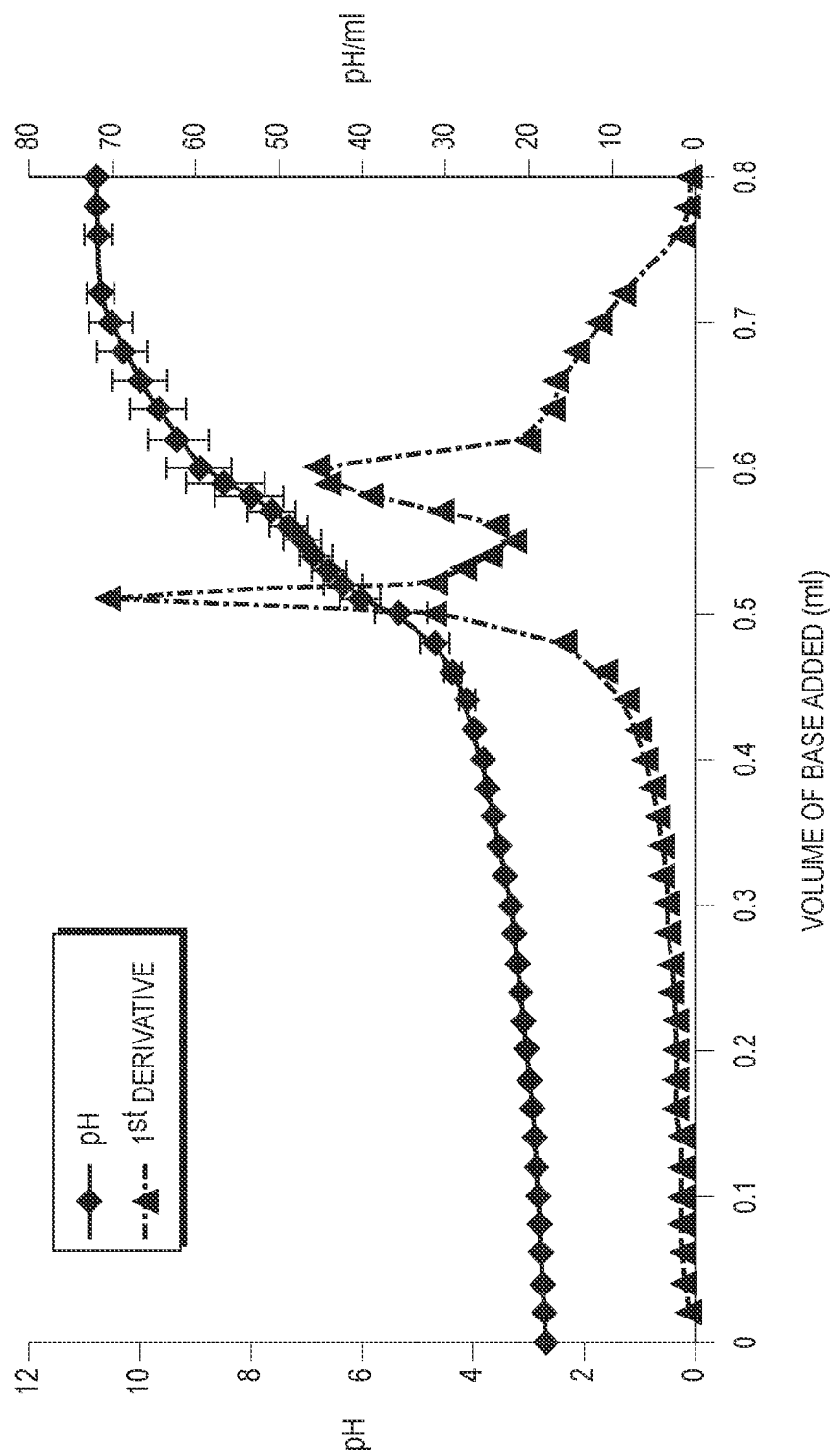
FIG. 3. pH Titration curve of APE and its resulting 1st derivative. The pKa is indicated by the peaks of the 1st derivative and the change in slope of the region of 6.0-7.5. The pKa present of the uronic acid at ~pH 3.5 is masked by the titration of the strong acid (HCl) by the strong base (NaOH). N=6.

Analysis of the NMR results revealed that APE is negatively charged through the presence of the galactouronic acid functional group and positively charged through the presence of deacetylated amines. Acid base titration was employed to determine the presence of the deacetylated amines and the degree of deacetylation (DDA) (FIG. 3). The presence of a plateau or a change in slope of the titration curve indicated the presence of a pKa. In order to better identify the presence of a pKa, the 1st derivative of the titration curve was taken. The 6 region between the two peaks of the curve corresponds to a pKa range of the polymer. The resulting titration curve and its 1st derivative (FIG. 3) showed that APE possesses a pKa in the range of pH 6.0-pH 7.5 which is indicative of a free amines (pKa≈6.8) present on the polymer. The uronic acid pKa (≈3.5) is not observed due to the titration of the strong acid (HCl) with the strong base (NaOH) overshadowing this pKa. The calculation of the degree of deacetylation was adapted from the chitosan literature. Since APE has one amine group per monosaccharide, like chitosan, this methodology was considered as a valid approximation of this parameter. Using equations 1 through 3 for the data generated in the titration curve the resulting degree of deacetylation was calculated to be 8.2%±2.8%.

Example 7

Physical Properties of APE

Capillary Viscometry

Figure 4A:
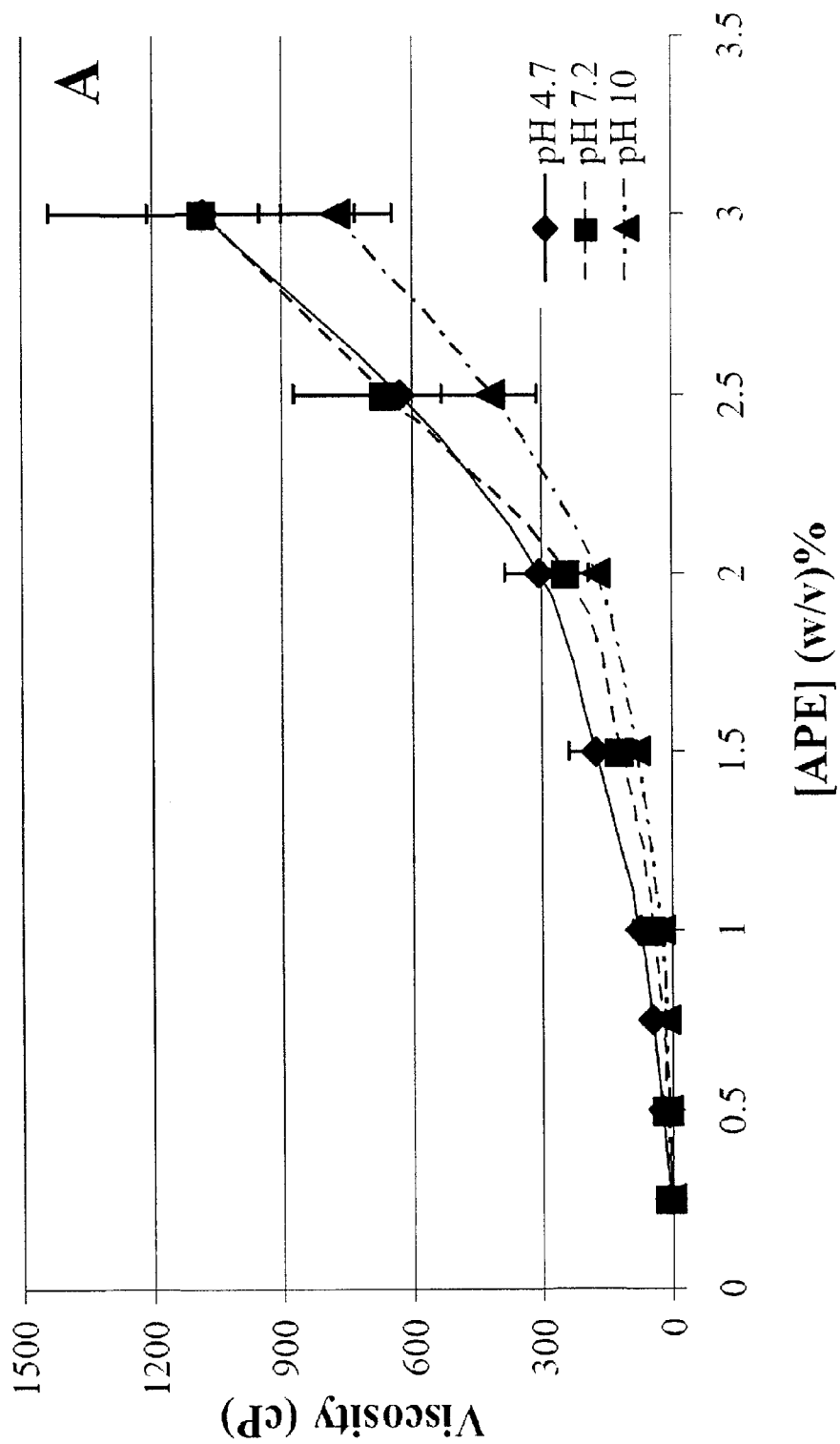
FIG. 4. Viscosity (cP) versus concentration of APE (w/v %) at different pH plotted from 0.25% (w/v %) to 3% (w/v %) APE (A) (N=3). Below that is the Fedors' plot of viscosity values of APE at different pH values for determination of intrinsic viscosity (B). Data was analyzed for concentrations of APE from 2.5 mg/ml to 15 mg/ml. Linear trend fits were developed and the corresponding equations are displayed next to the representative line. The values for η, the intrinsic viscosity, were calculated from the reciprocal of the slope.
Figure 4B:
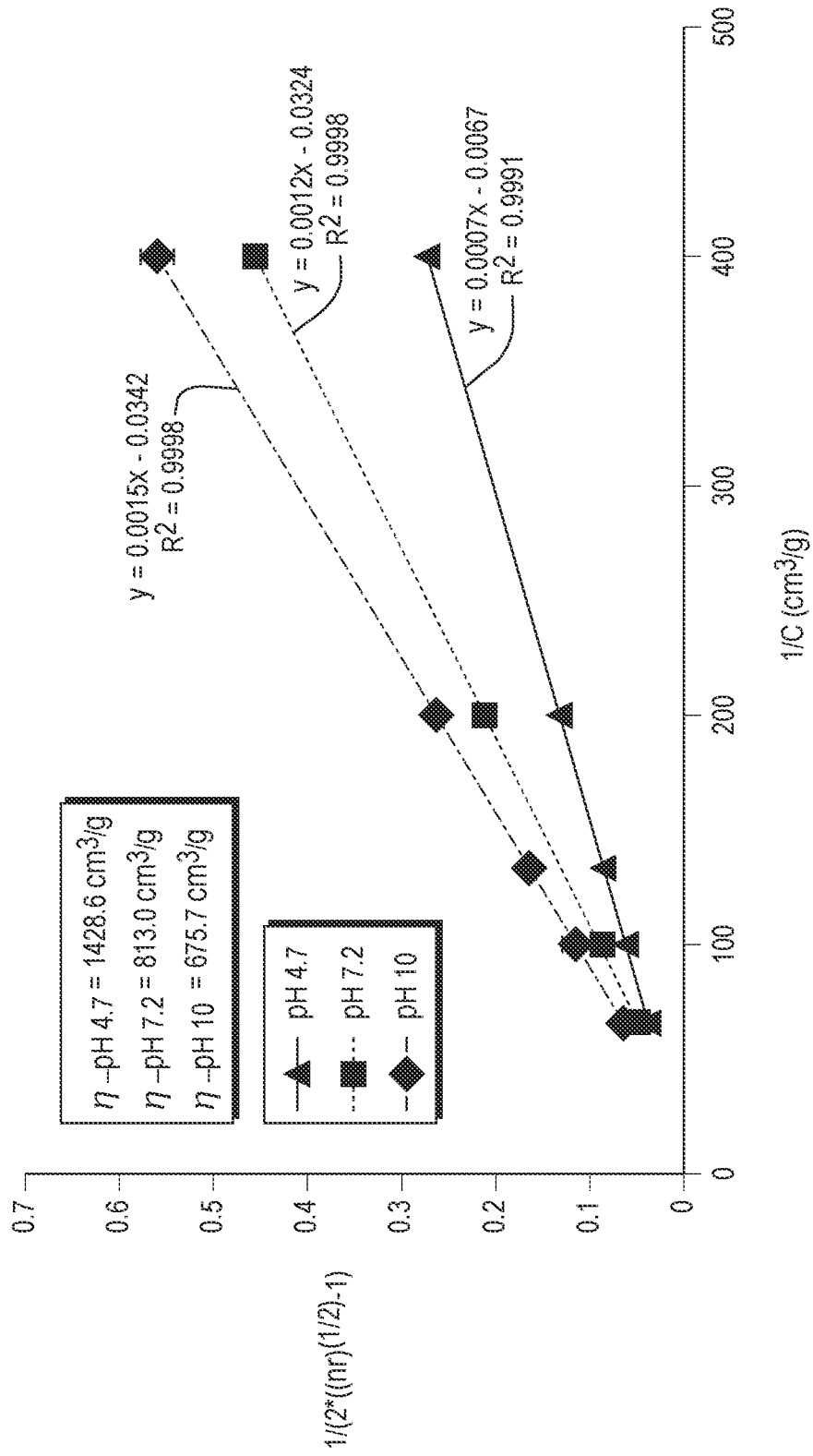

Capillary (Ubbleholde) viscometry was employed to determine the intrinsic viscosity, η, of APE solutions. The inverse of η is used to identify the value of c*, the polymer overlap concentration. The value of c* is the concentration at which the polymer concentration transitions from the dilute to semi-dilute regime. Ideal polymer analysis should take place below c* so it is important to identify this parameter. The viscosity curves indicated an exponential increase in viscosity with a linear increase in concentration (FIG. 4A). An increase in viscosity can be observed with a decrease in solution pH. The exponential increase in viscosity is representative of amphipathic polymers. Traditionally, η is determined through either the Kraemer or Huggins fits, but these mathematical manipulations do not accurately determine the intrinsic viscosity of amphipathic polymers. For this class of polymers, Fedors' fit is used to determine η (FIG. 4B).

As seen in the resulting plot (FIG. 4B), η increased with a decrease in pH. The value of η at pH 4.7 was significantly higher than η at pH 7.2 and more that twice that at pH 10. The values for η at all pHs are significantly higher than many polymers in its class and are comparable to known polymeric emulsifiers such as xanthan gum and chitosan. Using the value of η at each pH, c* was determined. The values of c* increased with an increase in solution pH where c*pH4.7=0.7 mg/ml, c*pH7.2=1.23 mg/ml and c*pH10=1.5 mg/ml.

Molecular Weight and Polymer Size

APE was prepared for chromatography at concentrations below c* and in buffers that were hypothesized to prevent polymer-polymer and polymer-column interaction. (Table 8). The ammonium bicarbonate buffers were selected in order to inhibit ionic interactions between the functional groups through charge satisfaction. The role of the modifier salt ($NaNO_3$ and LiBr) was to inhibit polymer absorption to the stationary phase and inhibit any ionic interactions. Both salts were selected due to their high degree of chaotrophism as indicated by the Hofmeister series. Samples were also analyzed in a sodium acetate buffer in order to attempt to identify the physical properties of the polymer at a lower pH. At this pH, accurate MW and Rg calculations were not able to be performed due to non-Gaussian chromatographic peaks (data not shown).

TABLE 8

Results from SEC-MALLS experiments. Two main buffer systems were selected for molecular weight analysis, ammonium bicarbonate (ABIC) and sodium acetate (SA). Modifier salt concentration was varied in order to be able to accurately analyze a single chain of APE.

| Buffer | Modifier Salt | Mw (g/mol) | $R_g$ | Poly | $R_H$ |
|---|---|---|---|---|---|
| 50 mM ABIC | 200 mM $NaNO_3$ | 3.34E+06 | 53.1 | 1.055 | 90.4 |
|  | 100 mM LiBr | 4.02E+06 | 48.6 | 1.02 | 93.5 |
|  | 500 mM $NaNO_3$ | 4.70E+06 | 51.3 | 1.12 | 100.5 |
| 50 mM SA | 200 mM $NaNO_3$ | could not be determined | | | 125.6 |

Mw—Molecular weight,
$R_g$—radius of gyration,
Poly—polydispersity of polymer,
$R_H$—Hydrodynamic radius.

Figure 5:
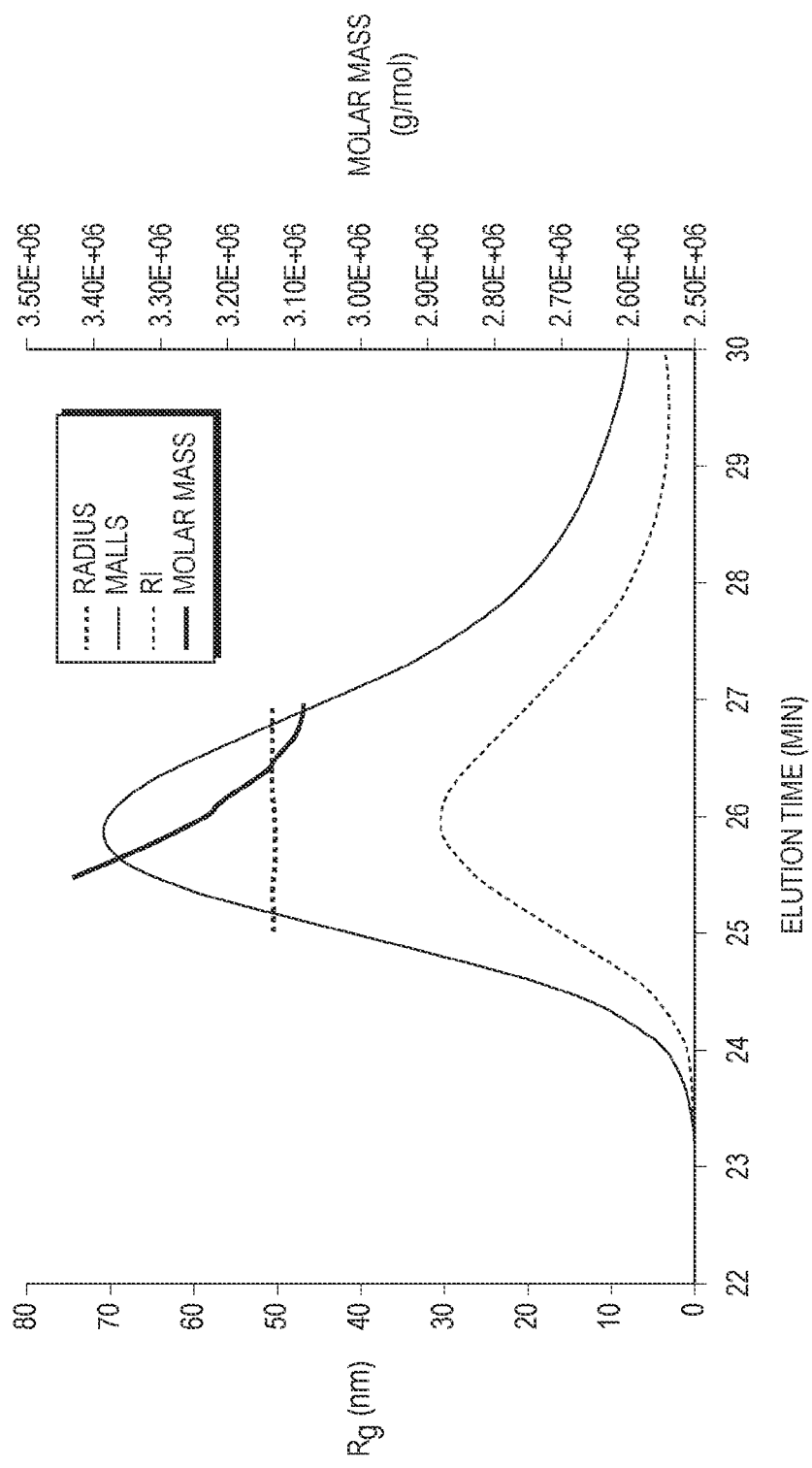
FIG. 5. A representative SEC-MALLS chromatogram. This chromatogram is the results of a SEC-MALLS run where 50 mM ABIC, 200 mM NaNO3, pH 10 was the mobile phase. Using analysis software the distributions of the molar mass and radius of APE were able to be determined. Legend: Radius—Rg distribution, Molar Mass—Molar mass distribution, RI—Differential Refractometer data, MALLS—Light Scattering data at one angle, 90°.

To perform MW analysis the dn/dc was calculated to be 1.23 ml/g (data not shown). The molecular weight was determined to be in the range of $3.4 \times 10^6$ to $4.7 \times 10^6$ with a corresponding $R_g$ of approximately 50 nm (Table 8). The light scattering results and the observed shape of the corresponding chromatographic peak indicated that APE has a high degree of monodispersity (FIG. 5). The sample that generated the lowest MW and $R_g$ was 200 mM $NaNO_3$. At higher concentrations of $NaNO_3$ both parameters increased, indicating a swelling or stiffening of the polymer coil. This was also observed for the stronger chaotroph LiBr. The hydrodynamic radius, $R_H$, demonstrated the same behavior. Moreover, $R_H$ was observed to be significantly larger than $R_g$ (Table 8). These observations are indicative of a polymer possessing a large hydration shell and having increasing rod-like character with increased counterion (salt) concentration and chaotrophism.

Surface Tension

Figure 6:
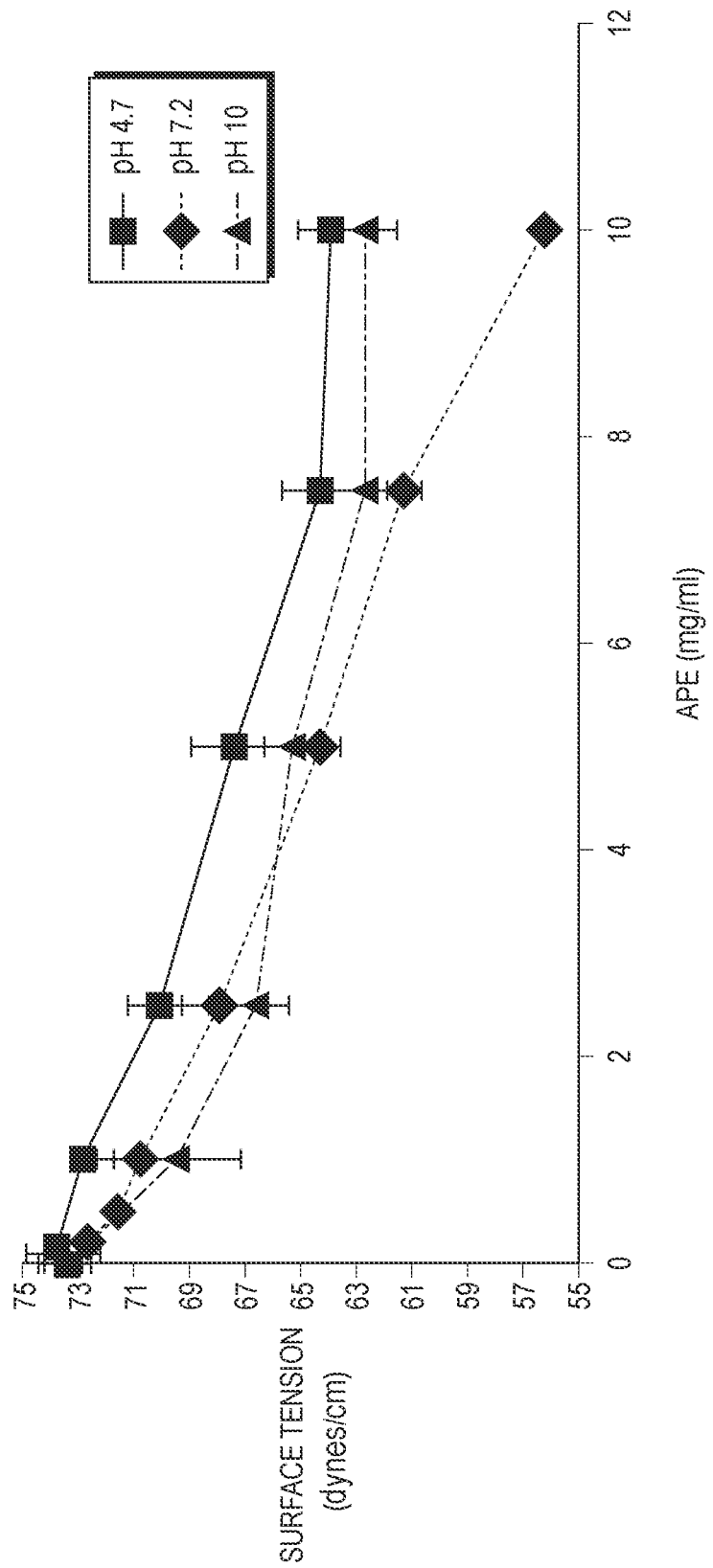
FIG. 6. Surface tension of APE solutions as different solution pH. (N=3)

The presence of the acetylated amino sugars and 3-hydroxybutyramido functional groups on APE indicate the presence of amphipathicity associated with the polymer. Amphipathicity can be determined through the observation of the reduction of surface tension of the polymer in solution when compared to water. To identify this behavior, the surface tension of increasing concentrations of APE at different pHs were assessed (FIG. 6). APE reduced the surface tension of water significantly, as concentration of the polymer increased with a linear dependence. No strong relationship between pH and surface tension was seen except at high concentrations where the APE at pH 7.2 had a lower surface tension than at pH 4.7 or pH 10. The surface tension value for 1% (w/v %) solution of APE at pH 7.2 was compared to other polymers at the same concentration (data not shown). APE was observed to reduce the surface tension more than chitosan (65.1 dynes/cm) but not as much as polyvinyl alcohol (PVA) (50.0 dynes/cm), indicating that it is comparatively more amphipathic than chitosan, but not as much as known synthetic amphipathic polymers such as PVA.

Critical Aggregation Concentration Determination

Figure 7:
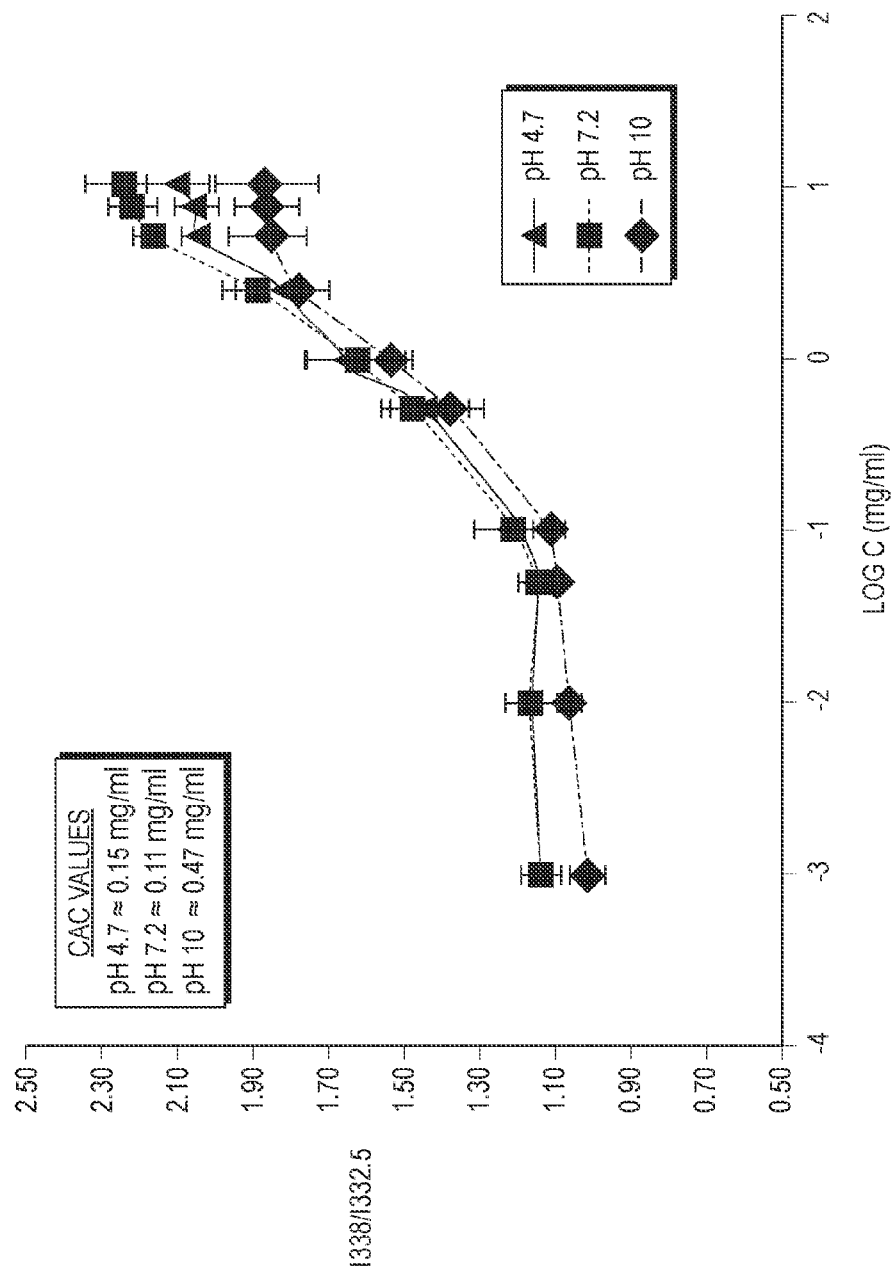
FIG. 7. Determination of the critical aggregation constant of APE. The CAC was determined through the observation of solublization of pyrene in aqueous solution. An increase in the fluorescence signal and the ratio of the two vibronic peaks signify an increase in the amount of pyrene solublized in hydrophobic regions in an aqueous solution. The CAC was established at three pH solutions, pH 4.7, pH 7.2 and pH 10. (N=3).

The pyrene solublization method has been widely used in order to determine the critical micelle concentration of block copolymers and surfactants. The method has been transferred to the analysis of amphipathic polymers to determine the concentration of the onset of hydrophobic association, known as the critical aggregation concentration (CAC). In the process of this aggregation phenomenon, hydrophobic regions that can entrap hydrophobic molecules begin to form. The CAC of a polymer can be identified by monitoring the solublization of pyrene through fluorescence spectroscopy. The amount of pyrene solubilized increased with increasing concentration of APE over all range of pH (FIG. 7). The shape of the resulting curves is typical of the technique, where at concentrations below the CAC there was no observed increase in fluorescence ratio (I), followed by a rapid ratio increase above the CAC (II), until a maximal fluorescence ratio was realized (III). The CAC was calculated by extrapolating section I and section II and identifying the concentration at which these lines intersect. At pH 4.7 and 7.2, the CAC was similar at values near 0.1 to 0.15 mg/ml. At pH 10, the CAC value was significantly higher at approximately 0.5 mg/ml. The results indicated that at lower solution pH, the onset of aggregation occurs at decreased polymer concentration.

Microcalorimetry

Microcalorimetry was employed to identify conformational changes of APE as a function of pH, temperature and ionic strength. APE was analyzed at these different conditions at a concentration of 5 mg/ml which was well above c*. The first set of experiments established a conformational transition in a low ionic strength environment (FIG. 8). A strong endothermic trough was observed at pH 4.7 and pH 7.2 and not witnessed at pH 10. The temperature at which the transition takes place was similar between the two troughs at approximately 72° C. The trough at pH 4.7 corresponded to a greater change in enthalpy than at pH 7.2, which indicated a stronger association being disrupted. Interestingly, neither transition was reversible upon cooling and not noticed again during subsequent heating (data not shown). This behavior has been witnessed with other bacterial polysaccharides and has been described as an ordered state to disordered state transition.

Figure 9A:
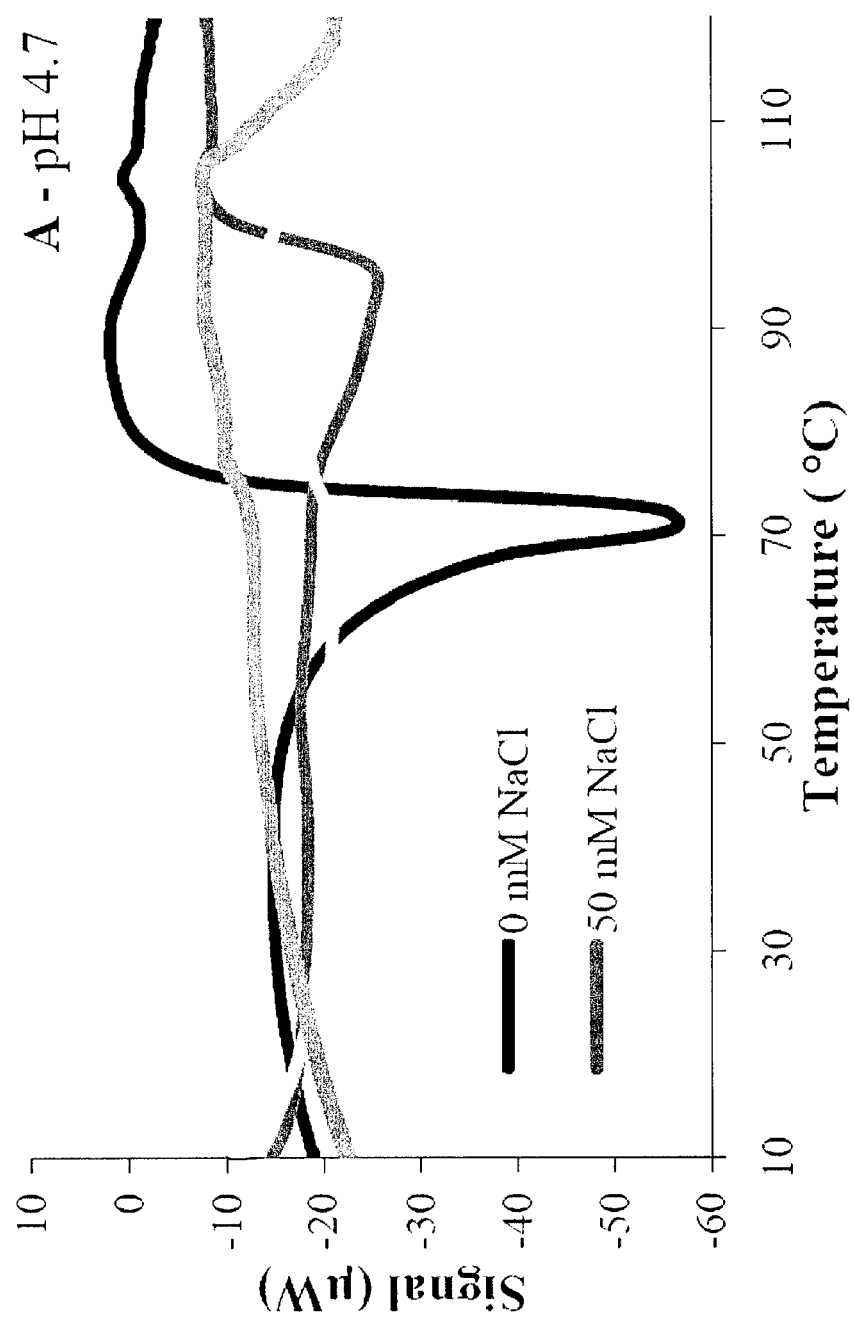
FIG. 9. Microcalorimetry data of APE solutions at varying concentrations of ionic strength at pH 4.7 (A), pH 7.2 (B), and pH 10 (C). The inset legend identifies the each curve corresponding to its respective ionic strength. All concentrations of APE were 5 mg/ml.
Figure 9B:
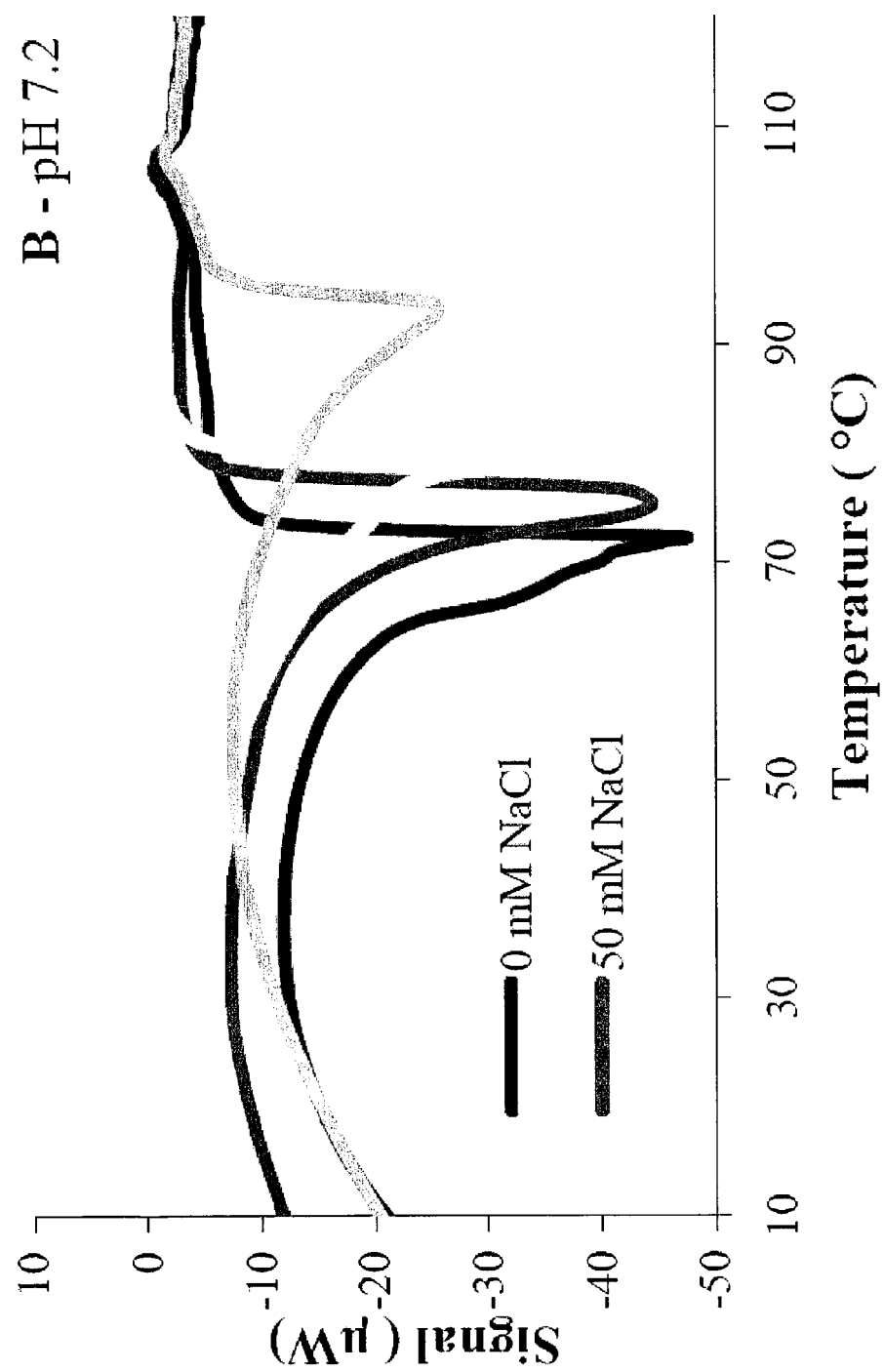
Figure 9C:
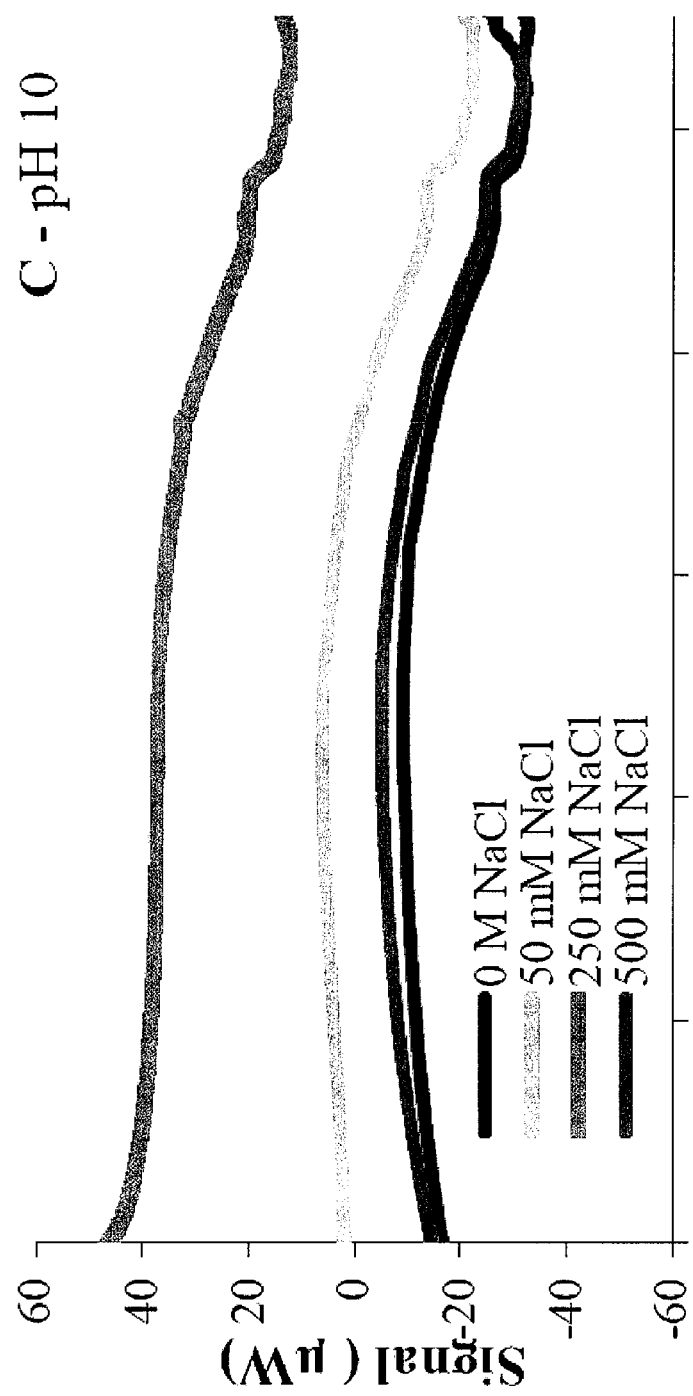

To further analyze the transition, the enthalpic behavior of the polymer was monitored as a function of ionic strength (FIG. 9). No change in behavior was observed at pH 10. At pH 4.7, the increase in the ionic strength caused a complete disappearance of the conformational transition. This is contrary to pH 7.2, where the appearance of the trough occurred at increased temperatures with increased ionic strength. With increased ionic strength, the enthalpy of the transition decreased, indicating that less polymer chains were undergoing the conformational transition (Table 9). All of the transitions were irreversible as witnessed during the low ionic strength experiments (data not shown).

TABLE 9

Transition temperature and enthalpy of transition for microcalorimetry data presented in FIG. 8. Enthalpies of transition were only calculated for microcalorimetric curves that exhibited transitions.

| Buffer | [NaCl] | $T_m$ (° C.) | ΔH (kJ/mol) |
|---|---|---|---|
| SP | 0 | 72.2 | 77.7 |
| | 50 | 75.6 | 74.2 |
| | 250 | 78.9 | 52.67 |
| | 500 | 93.6 | 45.93 |
| SA | 0 | 71.5 | 121.6 |
| ABIC | | n/a | |

Legend
SP—Sodium phosphate, pH 7.2,
SA—Sodium acetate pH 4.7,
ABIC—Ammonium bicarbonate, pH 10.

Circular Dichroism

Figures 10A, 10B:
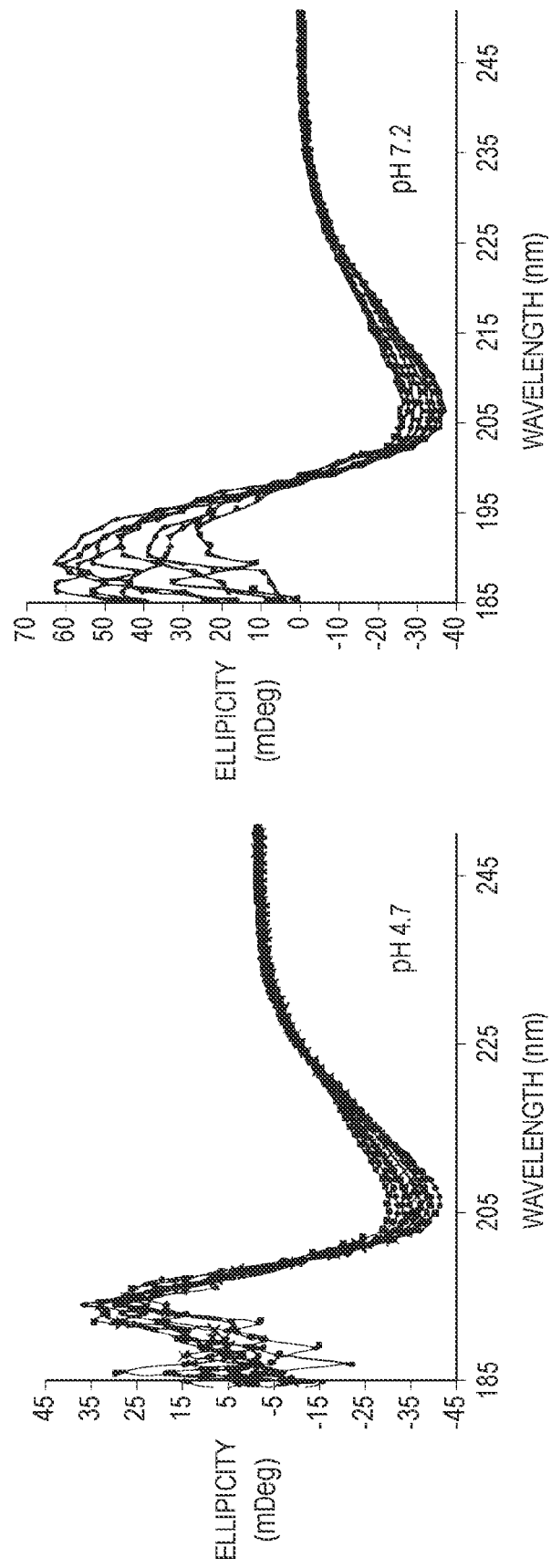
FIG. 10. Circular Dichroism Spectra of APE solutions. Figures (A), (B) and (C) are CD spectra at different pH will temperature increasing from 10° C. to 80° C. Figure (D) highlights the net change in ellipticity associated with trough depth as compared to the base value of 10° C. Legend for A-C ♦-10 C, ■-20 C, ▲-30 C, X-40 C, *-50 C, ●-60 C, +-70 C, ■-80 C.

Circular Dichroism can be used for polysaccharides as a means to qualitatively examine conformational transitions through manipulation of environmental conditions. The effects of temperature and ionic strength on APE were examined. The resulting CD spectrum of APE consisted of a trough at approximately 205 nm with a peak in the range of 190-195 nm (FIG. 10 A-C). The trough was well defined, but the peak was present in the far UV range which has been documented to be problematic for analysis due the noise associated with the C—H bond. The spectra had striking similarities to that of xanthan gum, where the trough is attributed to the presence of the acetyl chromophore and the peak is indicative of carboxyl chromophore. This result corroborated the chemical composition of APE, which identified the presence of these functional groups.

Figure 10D:
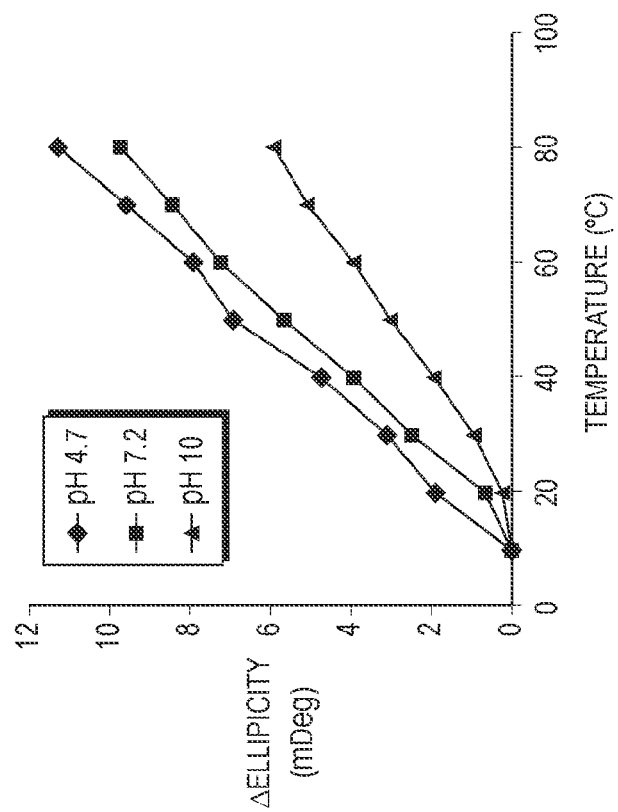
Figure 10C:
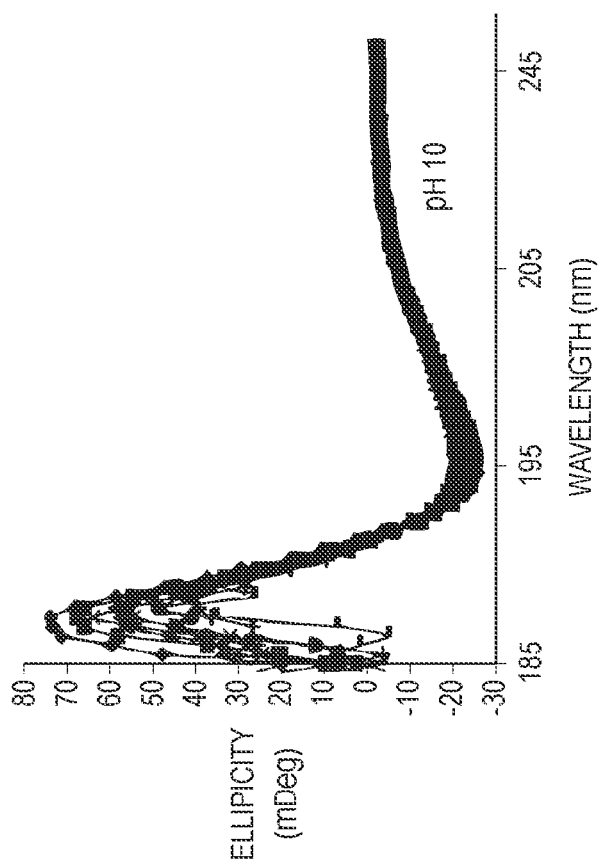

Increasing temperature resulted in an increase in the trough signal, while the peak signal decreased (FIG. 10D). This behavior is indicative of an observed order to disorder conformational transition, which has been identified in the study of xanthan gum. The amount by which the signal increased had a dependence on pH, where at pH 4.7 and pH 7.2, the rate at which the signal increased was significantly higher than at pH 10. The pH of the solution had a different effect on the peak and trough intensity. With an increase in pH both the peak and trough intensity increased. The effect of ionic strength on the CD spectra of APE was not as pronounced as the effect of temperature. At pH 10 no observed difference of spectra was noticed (data not shown). At pH 4.7 and 7.2 there appeared to be a slight decrease in trough signal, but it was not as pronounced as the effect temperature had on the signal. Due to the increase in solution ionic strength the far UV signal overwhelmed the CD instrument and the far UV peak could not be analyzed.

Structural Definition of APE

Figure 11:
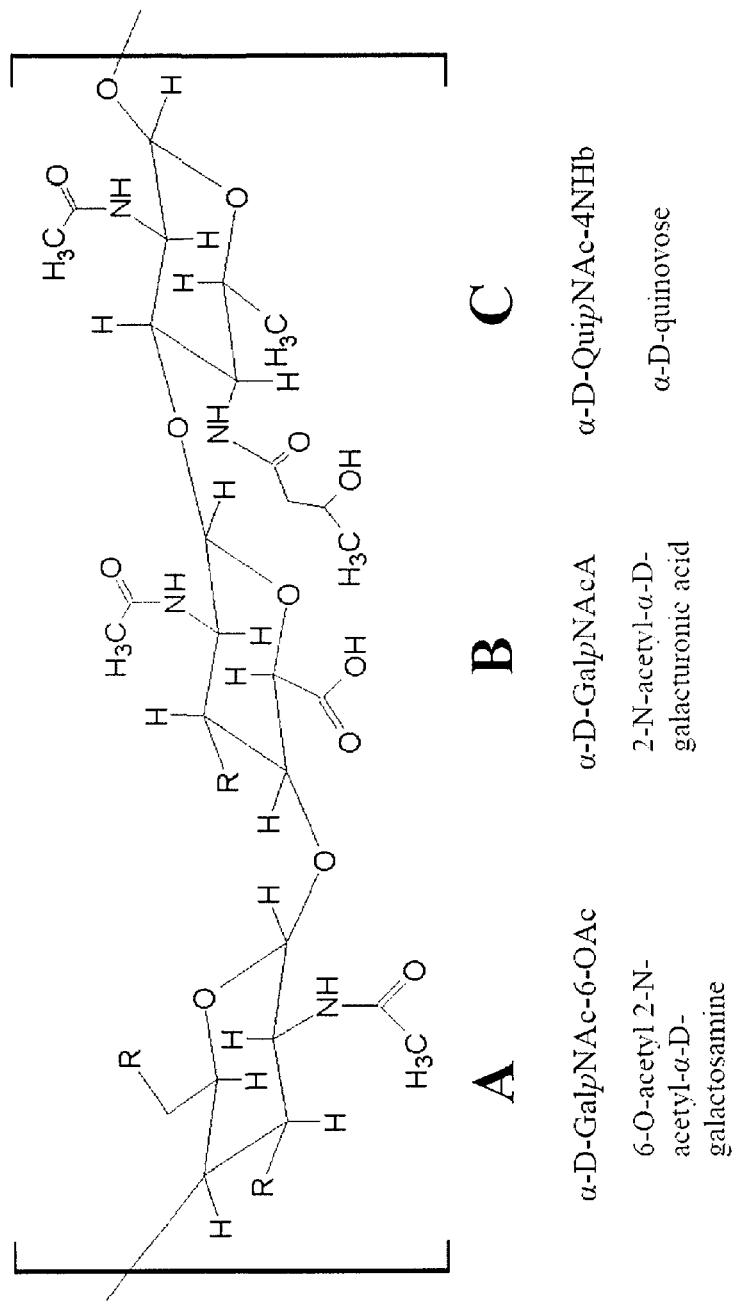
FIG. 11. Structure of the repeating unit of the APE polysaccharide from *Acinetobacter venetianus* RAG-1. hydroxybutyramide linked to C4 of residue C, R═OH or OAc FIG. 12. (A) $^1$H NMR spectrum of the native form of APE, (B) $^{13}$C NMR spectrum of same.

Analysis of the NMR spectra identified APE as a linear polysaccharide with a tri-saccharide repeating unit (FIG. 11). The recognition of this structure was made through the combination of 1D and 2D NMR techniques. At first, deacetylation of the polymer was not considered, but after analysis of the $^{13}$C spectra (FIG. 12B) it was observed that the peaks had weak shoulders and possibility of a large number of monosaccharides. The presence of these features suggested the possibility of additional O-acetylation. However, O-acetylation would only be possible at positions C3 and C6 on A and C3 on B (FIG. 11). In order to elucidate the presence of acetylation, the native APE was treated with 12.5% aqueous NH3 solution to O-deacetylate the polysaccharide. After deacetylation the NMR spectra of the modified polysaccharide was more clear and easier to interpret. It was observed that the spectra generated were more typical of a regular polysaccharide with a linear trisaccharide repeating unit.

At this point, it was known that there were three N-acetyl groups, one O-acetyl group, one uronic acid, and a 3-hydroxybutyramido group at C4 on residue C (Table 7). However, there was no indication on the exact structure of the monosaccharides that comprised the repeating units. To identify these sugars, the 2D spectra with resulting coupling constants were examined. The $^{13}$C spectra of the native APE sample (FIG. 12B) showed the presence of six peaks in the range of 98 to 102 ppm which were designated as alpha anomeric carbon residues, an observation that was confirmed by the 2D $^1$H—$^{13}$C HSQC coupled spectrum. The J(HC) were in the range of 168 to 178 Hz, which was typical for alpha proton-carbon coupling constants (Table 6). Furthermore, the ge-HSQC spectrum contained four resonances in the 48 to 54 ppm window, which was characteristic of both carbon bound to nitrogen and the presence of three acetamido groups and one 3-hydroxybutyramido group. Each of the three acetamido groups was correlated to carbon 2 in residue A, B, or C. The 57.98 ppm signal for carbon 4 in residue C indicated that it was the acylation site for the 3-hydroxybutyramido group.

Figure 13:
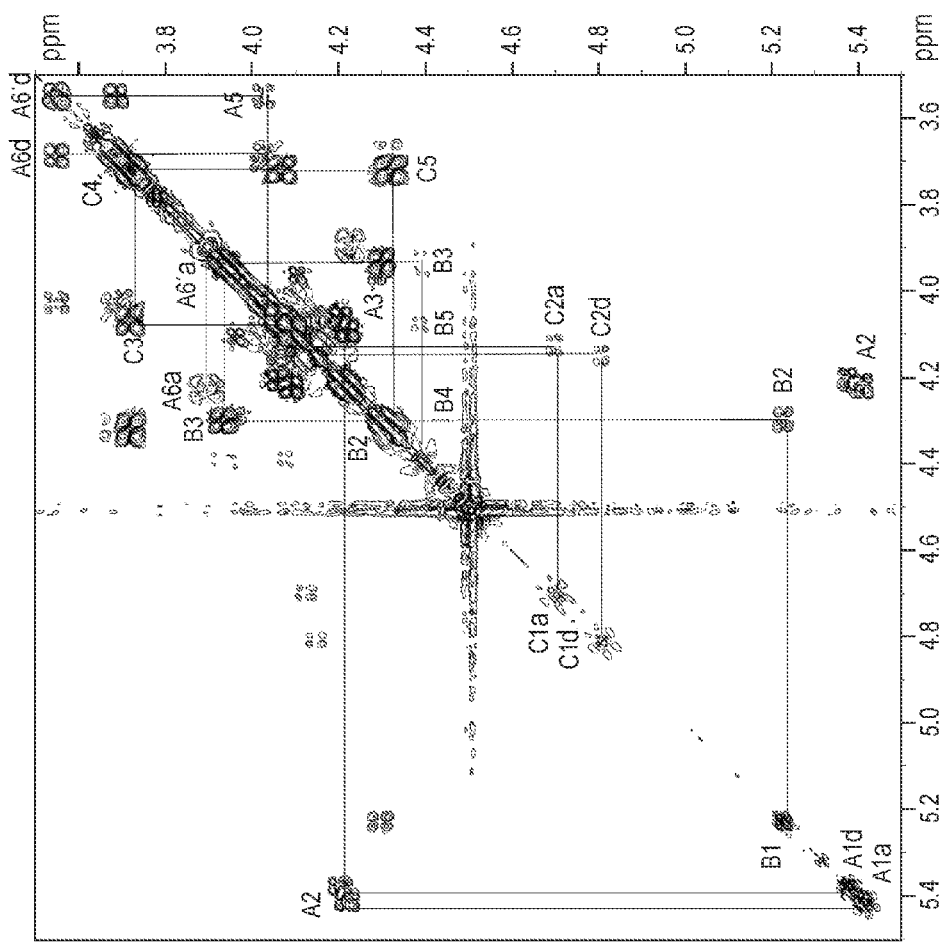
FIG. 13. Phase-sensitive DQF-COSY spectrum of native APE.

Complete $^1$H assignments of native and deacetylated APE were then designated from the 2D DQF-COSY and TOCSY experiments (Table 6). The DQF-COSY (FIG. 14) was able to confirm most of the $^1$H spin systems (FIG. 12A). These results were then further confirmed by the 2D TOCSY spectra (data not shown). The majority of the work to identify the individual monosaccharides was performed through the analysis of these spectra. It was noticed from the DQF-COSY in FIG. 13 that the anomeric resonance at 5.39 ppm from residue AdH1 had a cross peak to 1-12 at 4.21 ppm, and a subsequent cross peak from H2 to H3 at 4.07 ppm. However, further spin connectivity could not be determined from H3 to H4 in the DQF-COSY. Cross peaks from H6, H6' at 3.70, 3.56 ppm to H5 at 5.06 ppm were observed, but H5 to H4 was not observed. The absence of further spin connectivity in DQF-COSY was considered to arise from small J3,4 and J4,5 coupling constants, which prevented magnetization transfer past either H3 or H5. This result was expected for a galactopyranosyl residue. An inter-residue NOE correlation from H1 in residue Cd at 4.82 ppm to H4 in residue A was observed at 4.01 ppm. The 2D NOESY spectrum (Table 7 and FIG. 14) also exhibited intra-residue NOE correlations from A1 to A2 and A5 that supported the galactopyranosyl configuration.

Figure 14:
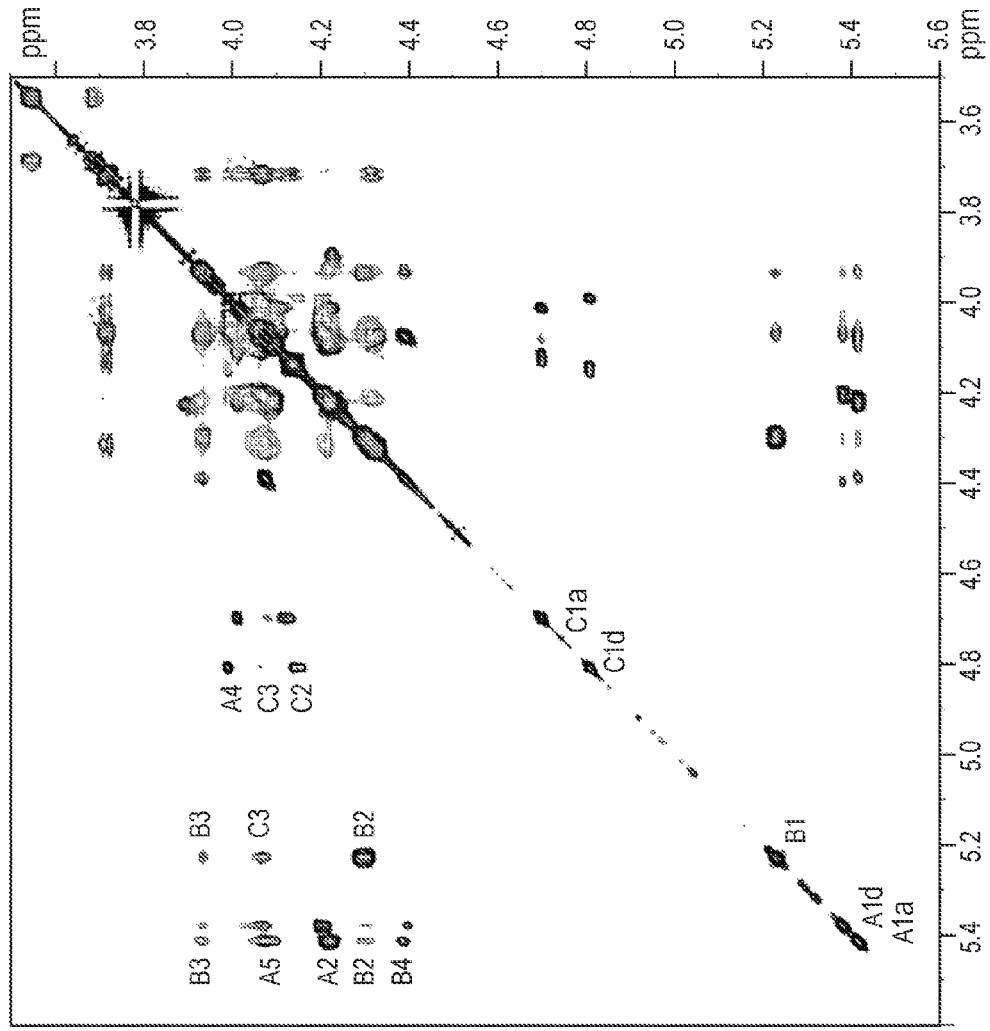
FIG. 14. Phase-sensitive NOESY spectrum with 80 ms mixing time of native APE.

Monosaccharide B1 showed an anomeric resonance at 5.24 ppm and gave a cross peak to H2 at 4.30 ppm, which in turn gave a cross peak to H3 at 3.94 ppm. Spin connectivity from H3 to H4 was very weak at 4.40 ppm, likewise from H4 to H5 was also very weak at 4.08 ppm. The chemical shift of H4 at 4.40 ppm was typical of an uronic acid, suggesting that residue B was galacturonic acid. The 2D NOESY showed intra NOE correlations from H1 to H2 and H3 which supported the galactopyranose configuration (FIG. 14). The analysis of residue Cd's anomeric resonance at 4.82 ppm showed a series of cross peaks starting with H2 at 4.16 ppm and in turn, successively, to 113 at 4.07 ppm, to H4 at 3.71 ppm, to H5 at 4.32 ppm, and finally to H6 at 1.12 ppm. Strong coupling throughout this spin system suggested a glucopyranosyl configuration with a 6-deoxy methyl group, i.e., quinovose.

The 2D NOESY spectrum (FIG. 14) also showed three intra-ring NOE correlations from H1 to H2 (s), H4 (w) and H5 (w), which lent further credence to the glucopyranosyl configuration. The 13C spectra discussed below established the presence of a second N-acyl chain at C4 of residue C. Based upon the coupling sequence beginning with the methyl resonance at 1.24 ppm coupled to a CH—OH group at 4.14 ppm and finally to a methylene groups at 2.42 and 2.32 ppm, this side chain was shown to be a 3-hydroxybutyramido group.

Further identification of the polymeric structure was completed through the $^{13}$C assignments from the native and deacetylated APE in the 2D ge-HSQC experiments (Table 6). In deacetylated APE, the assigned anomeric proton resonances at 4.82, 5.24, and 5.39 ppm showed correlations to directly bonded carbon resonances in the chemical shift range of 98 to 102 ppm. This was characteristic of anomeric carbon atoms in covalently linked monosaccharide residues, confirming the presence of three monosaccharide residues in the repeating unit. The native APE sample showed the presence of six peaks in the range of 98 to 102 ppm which were designated as alpha anomeric carbon residues, an observation that was confirmed by the 2D $^1$H—$^{13}$C HSQC coupled spectrum. The J(HC) were in the range of 168 to 178 Hz, which was typical for alpha protoncarbon coupling constants (Table 6). The ge-HSQC spectrum contained four resonances in the 48 to 54 ppm window, which was characteristic of both carbon bound to nitrogen and the presence of three acetamido groups and one 3-hydroxybutyramido group. Each of the three acetamido groups was correlated to carbon 2 in residue A, B, or C. The 57.98 ppm signal for carbon 4 in residue C indicated that it was the acylation site for the 3-hydroxybutyramido group.

Additionally, it was noticed that native APE exhibited partial O-acetylation in residue A at position 6, and possibly at position 3 in residues A and B. The first was readily seen in the ge-HSQC spectrum by shifts in the signal for the hydroxymethyl group at 64.1 ppm (deacetylated 62.7 ppm). Expansion of the 1D 10 $^1$H spectrum (Table 6) suggested that additional, weaker peaks were concealed beneath the corresponding A6-O-acetyl methyl protons at 2.1 ppm. This was further confirmed in the potentiometric titration experiment. Where it was noticed that the monosaccharides were partially deacetylated at these carbons since a positive charge was observed during the titration.

Example 8

Preparation of APE-BSA Nanoparticles

Briefly, a solution of 5 mg/mL BSA was incubated with the appropriate sodium tripolyphosphate (TPP) solution for each formulation in the same buffer as the BSA for 15 minutes to allow for equilibration. Following this incubation, an APE solution in the same buffer of the appropriate concentration for each formulation was added to the mixture and incubated at room temperature on a rocker for 1 hour. The final concentration of BSA was always 1 mg/mL, whereas the final concentration of APE was 0.5 mg/mL, 1.0 mg/mL or 2 mg/mL and the ratio of TPP to APE was 1:1, 5:1, or 10:1. These parameters were varied in order to optimize formulation conditions for these nanoparticles. Final reaction volume was restricted to 250 µL.

Example 9

Isolation of APE-BSA Nanoparticles

Because the stability of the particles was not known, we chose to avoid the usual practice of ultracentrifuging the samples to isolate the nanoparticles in favor of a milder isolation technique. Briefly, after incubation for 1 hour the samples were put into centrifugal membrane filters with a molecular weight cut off (MWCO) of 300 kDA (Nanosep 300K, Pall Life Sciences) and spun at 5,000 rcf until dry. The nanoparticles should have been too large to pass through the filter pores, while the unbound BSA should pass through in the flow through. The flow through was assessed for protein content and subtracted from the total protein in the starting solution.

Figure 15:
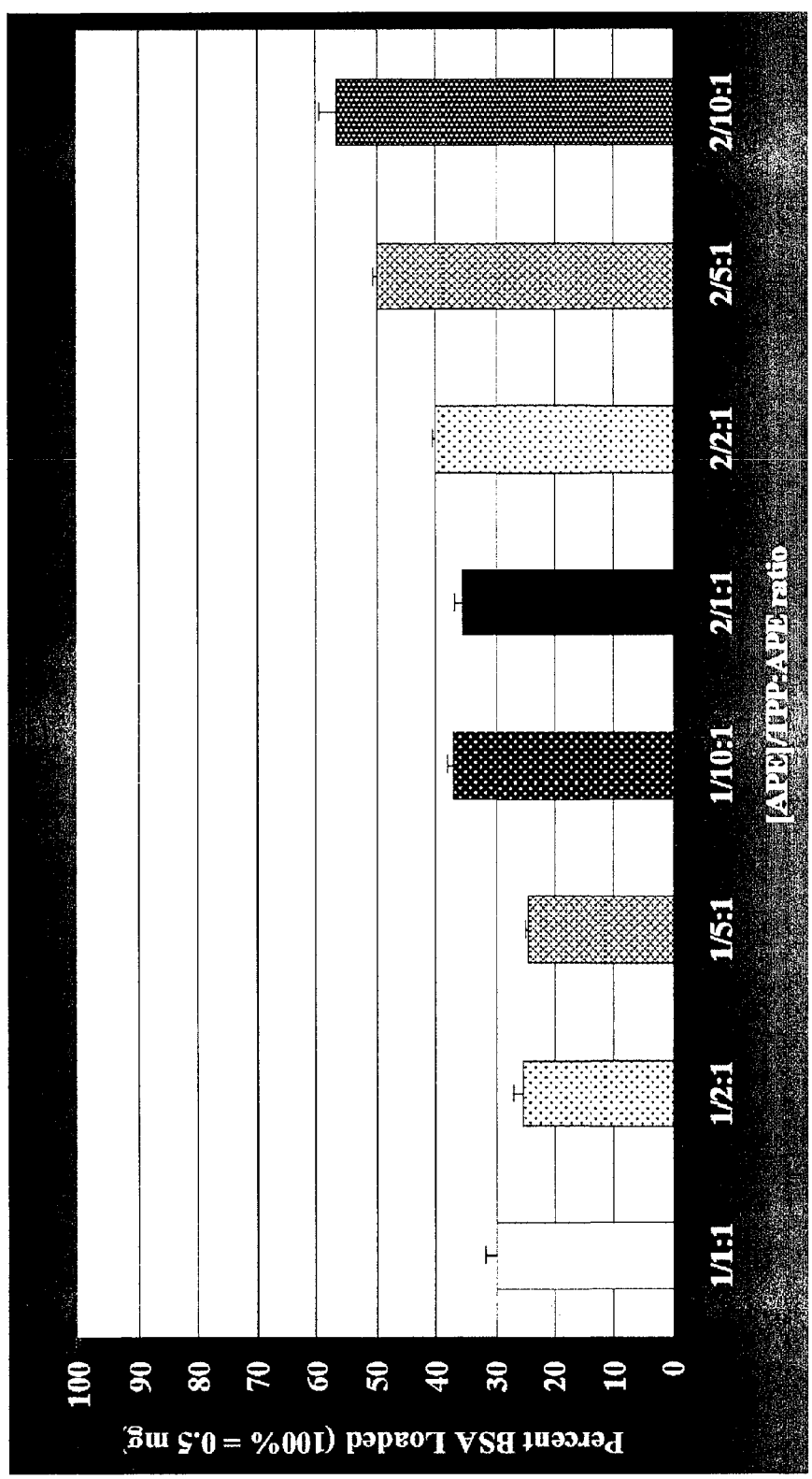
FIG. 15. Loading efficiency of APE nanoparticles by ionic gelation ranged from approximately 30-50%.

Loading efficiency of APE nanoparticles by ionic gelation ranged from approximately 30-50% is seen in FIG. 15. Nanoparticles had an average diameter of approximately 150 nm, see Table 10.

TABLE 10

Concentration of BSA, APE and TPP relative to diameter of nanoparticle and polydispersity of the nanoparticles.

|  | BSA | TPP | APE | Partical Diam. (nm) | Polydispersity |
| --- | --- | --- | --- | --- | --- |
| 1/1:1 | 1 mg/ml | 1 mg/ml | 1 mg/ml | 157 nm | 0.161 |
| 1/2:1 | 1 mg/ml | 2 mg/ml | 1 mg/ml | 128 nm | 0.353 |
| 1/5:1 | 1 mg/ml | 5 mg/ml | 1 mg/ml | 141 nm | 0.236 |
| 1/10:1 | 1 mg/ml | 10 mg/ml | 1 mg/ml | 136 nm | 0.221 |
| 2/1:1 | 1 mg/ml | 2 mg/ml | 2 mg/ml | 155 nm | 0.304 |
| 2/2:1 | 1 mg/ml | 4 mg/ml | 2 mg/ml | 160 nm | 0.208 |
| 2/5:1 | 1 mg/ml | 10 mg/ml | 2 mg/ml | 161 nm | 0.293 |
| 2/10:1 | 1 mg/ml | 20 mg/ml | 2 mg/ml | 158 nm | 0.305 |

Example 10

Antigen Delivery of APE

To ascertain if previous adjuvant activity demonstrated with vaccine formulations containing emulsan could be attributed to APE, a pilot study was conducted utilizing ovalbumin (OVA) as the model antigen. Immunized animals were assessed for their response by OVA-specific ELISA.

Figure 16:
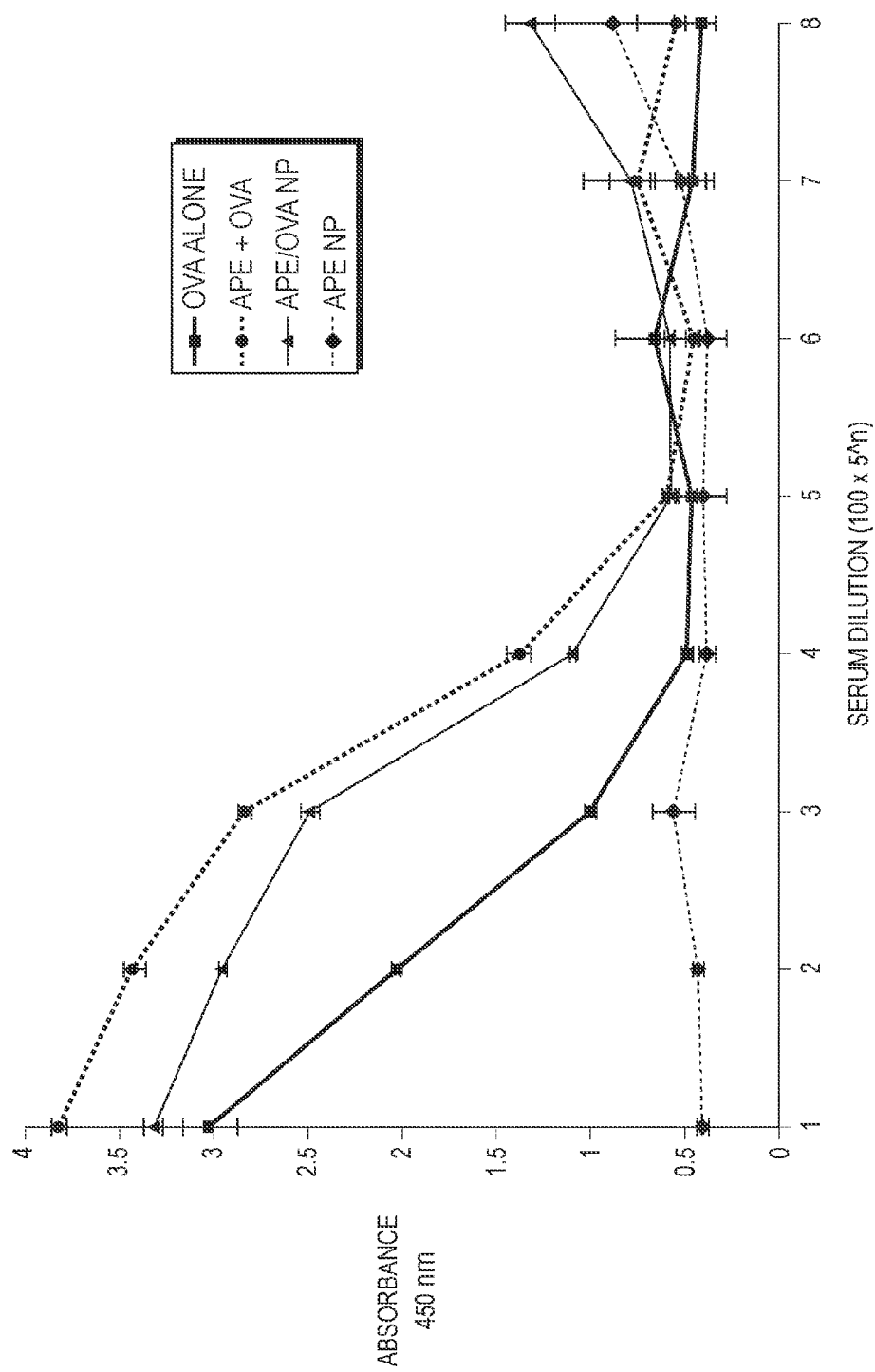
FIG. 16. OVA-specific titers in animals immunized with OVA and APE, or OVA loaded in APE nanoparticles were higher than those observed immunized with OVA alone.

OVA-specific titers in animals immunized with OVA and APE, or OVA loaded in APE nanoparticles were higher than those observed immunized with OVA alone (FIG. 16). Further studies utilizing a challenge model of *Yersinia pseudotuberculosis* are underway.

Example 11

Solid Lipid Nanoparticles for Delivery of Paclitaxel

Nanoparticle Formation

The goal of this study was to examine the viability of using the bacterial polysaccharide APE as the primary constituent in a drug delivery system, a lipid nanoparticle system. The role of APE in the proposed SLN system was to act as the hydrophilic surfactant that would help form and stabilize the emulsion. Additionally, it was hypothesized that APE would coat the SLN as a polymeric shell, potentially imparting the ability to prolong drug release and add stealth to the nanoparticles. This hypothesis was tested by developing a SLN system for the encapsulation and release of PTX. The feasibility of such a system was demonstrated through analysis of particle size, particle morphology and degree of drug encapsulation. The effectiveness of this system was demonstrated through an in vitro cell viability assay where the cancer cell line MCF-7 (human breast adenocarcinoma) was subjected to the SLN.

Solid lipid nanoparticles were formed by the hot homogenization method. The particles were formed in a two step process. The first step was to form a pre-emulsion of APE, egg phosphatidylcholine (EPC) (Sigma, St Louis, Mo.), trimyristin (TM) (Sigma, St. Louis, Mo.), and paclitaxel (PTX) (LC Laboratories, Woburn, Mass.). The materials were mixed in a volume of 6 ml in the following proportion of APE/EPC/TM/PTX of 30/60/200/6 mg. In order to form the pre-emulsion, the PTX, EPC and TM were heated at 65° C. and water bath sonicated (Branson Ultrasonics Danbury, Conn.) to dissolve the PTX in the lipid phase. An aqueous APE solution was heated to 65° C. and added to the mixing vessel with the lipid. The pre-emulsion was formed by mixing the two phases using a tissue homogenizer set at 24,000 rpm (UltraTurrax T25, IKA, Germany) for 10 min at 65° C.

After pre-emulsion formation, the hot emulsion was transferred to a high pressure homogenizer (Microfluidics, Newton, Mass.) for hot homogenization. Homogenization was carried out at 65° C. The emulsion was homogenized for 5 cycles at 6,000 psi and then immediately placed in an ice-water bath at 4° C. for 30 min to solidify the lipid core and form the particles. After cooling, the particles were centrifuged at 4,000×g for 15 min in order to precipitate any insoluble drug or lipid that was not incorporated. The resulting supernatant was collected as the SLN and the precipitate was discarded.

Particle Size and Formation

The size of the nanoparticles was determined using a Brookhaven Instruments BI-200SM Goniometer with a 532 nm wavelength laser light scattering system (Brookhaven Instruments, Holtsville, N.Y.). To prepare the samples of the nanoparticles for analysis, the particles were diluted 1000× in WFI water (HyClone Labs, Logan, Utah) and filtered with a 1 μm Puradisc polyethersulfone (PES) syringe filters (Whatman, Kent, United Kingdom). In order to breakup any non-specific particle aggregation the particles were water bath sonicated for 5 min at room temperature. For dynamic light scattering analysis, the temperature was maintained at 25° C. and the goniometer arm was set to 90°. Rx was determined by using the Dynamic Light Scattering software (Brookhaven Instruments, Holtsville, N.Y.) using the cubic cummulant data analysis algorithm.

Particle Stability

The stability of the SLN was analyzed using dynamic light scattering. The samples that were prepared for initial particle size identification were saved and stored at room temperature for 4 weeks. At the end of each week, each sample was measured. $R_H$ was determined by using the Dynamic Light Scattering software using the cubic cummulant data analysis algorithm.

Scanning Electron Microscopy

Scanning electron microscopy (SEM) of the particles was performed using a Zeiss Ultra55 FESEM (Carl Zeiss, Germany) at the Harvard University Center for Nanoscale Systems. SLN nanoparticles were frozen and lyophilized to prepare for analysis. Particles were streaked onto sample stubs and sputtered with platinum-palladium metal. Samples were also prepared by diluting the SLN in filtered DI water and placing a drop of the dilute SLN solution on the SEM stub. The drop was allowed to dry overnight and the sample was then sputtered for analysis.

Encapsulation Efficiency

The determination of encapsulated paclitaxel was performed with a hot methanol extraction (276). A 100 μl sample of the SLN was lyophilized, added to 3 ml of methanol and heated at 65° C. in a water bath for 30 min to dissolve the lipid core and solublize PTX. After heating, the methanol solution was placed in a −20° C. freezer for 30 min in order to solidify the lipid. Once the lipid was noticed to be solidified, the sample was centrifuged at 10,000×g for 20 min in order to precipitate the lipid. The supernatant was decanted and saved for analysis, while the precipitated lipid was discarded.

The methanol solution containing the extracted PTX was analyzed using HPLC. Samples were prepared by centrifuging the samples at 10,000×g for 10 min to precipitate any insoluble material. The method used was a reversed phase chromatographic method that has been described previously (277). A Waters 2690 HPLC system (Waters Corporation, Milford, Mass.) was used to manage the experiments with a Source RPC 4.6/150 mm column (GE Healthcare, Piscataway, N.J.) and a Waters 996 photodiode array UV spectrophotometer detector (Waters Corporation, Milford, Mass.) at 227 nm for detection of PTX. Each sample of SLN and standards were injected at 50 μl volumes for analysis.

A standard curve of known PTX concentration was formed based on the areas of the resulting chromatographic peaks. The peak areas from the SLN samples were compared to the standard curve developed for PTX in order to get a concentration and mass of PTX in each sample. The encapsulation efficiency was calculated as a percentage by mass of PTX encapsulated in the particles as compared to the amount of PTX added to the emulsion mixture.

In Vitro Cytotoxicity

The effect on the viability of cells when subjected to SLN was performed using the MCF-7 human breast adenocarcinoma cell line (ATCC, Manassas, Va.). The MCF-7 cells were grown in Dulbecco's Modified Eagle Medium (D-MEM) (Invitrogen, Carlsbad, Calif.) supplemented with 10% (v/v %) Fetal Bovine Serum (Invitrogen, Carlsbad, Calif.) and 50 μg/ml of Penicillin-Streptomycin (HyClone, Logan Utah). After the cells reached confluency, they were plated in a 96-well plate with a density of 10,000 cells/well and were allowed to grow overnight at 37° C. with 5% CO2. The next day the media was removed and replaced with fresh growth media (for positive control samples) or media supplemented with the sample (SLN or PTX solublized in Cremophor EL) or DI water to kill the cells through isotonic shock (negative control). The cells were then allowed to grow for 3 days undisturbed.

After 3 days, the media was removed and replaced with 200 μl of RPMI 1640 media without Phenol Red (Invitrogen, Carlsbad, Calif.). The viability was determined using the CellTiter 96® AQueous One Solution Cell Proliferation Assay (MTS) (Promega, Madison, Wis.). To the cells in RPMI media, 20 μl of the MTS solution was added and allowed to incubate for 1 hour at 37° C. and 5% CO2. After one hour, the plate was measured at λ=490 nm in a SpectraMax microplate reader (Molecular Devices, Sunnyvale, Calif.). The resulting data was extrapolated and calculated according to the manufacturer's recommendations in order to get a percentage of cell viability. Standard 160 deviations were calculated to compare the differences in cell viability between the cell treatments.

Example 11

Solid Lipid Nanoparticles for Delivery of Paclitaxel

Particle Size and Morphology

Figure 17:
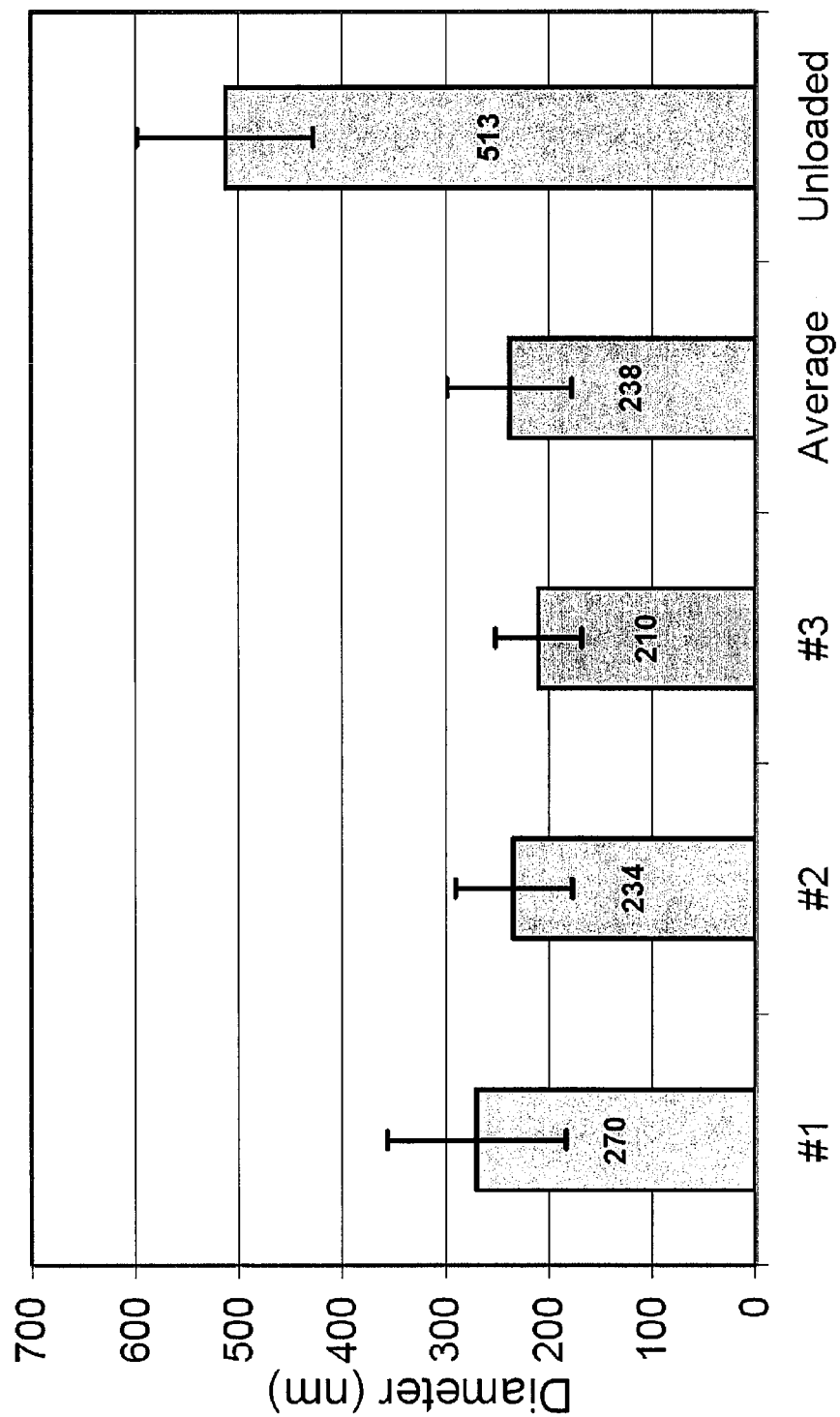
FIG. 17. The above bar chart shows the particle size of three different preparations of the SLN (#1, #2, #3), unloaded SLN, and the overall average of the loaded SLN. The error bars were calculated from the polydispersity result generated by the cubic data fit. The error bars for the "Average" sample was calculated from the standard deviation of samples 1 through 3. The numbers inside the bars are the value of the mean particle diameter. The unloaded sample was an average of three separate unloaded samples and its error bars were calculated from a standard deviation of all three samples.

The particle sizes of several SLN samples are presented in FIG. 17. As seen in the figure, the average diameter was 238 nm for particles loaded with PTX. Interestingly, the particle size for unloaded particles was significantly larger at 513 nm. This is most likely due to the stabilizing influence of PTX helping to form a denser hydrophobic core, increasing surfactant interactions and condensing the particle. All of the preparations appeared to have a low degree of polydispersity, as evidence by the standard error bars on the graph. This indicated that the there was a small size distribution present among the nanoparticles. Samples #1-#3 also demonstrated that the method of production for nanoparticles yielded reproducible results. The particle size was also analyzed using the CONTIN data fit and calculated similar results with approximately the same mean particle diameter and low polydispersity (data not shown). The mean particle size was deemed to be sufficient for chemotherapeutic drug delivery since particles were small enough to be internalized by cells (<1 μm) and also small enough to take advantage of the EPR effect (278).

After the particle size was established through dynamic light scattering, the particle size and morphology were analyzed using SEM. The shape of the nanoparticles appeared to be a mixture of spherical and elliptical particles. It was unknown if the elliptical particles were a function of the sample preparation technique or if the elliptical particles were formed through the SLN process. The particles were also present in an aggregated state which was attributed to adverse effects from sample preparation. Some of the particles displayed a dehydrated look, whereby the particles had many indentations present on the surface. Typically, this indicates that the particles are dehydrated and have begun to selfcollapse. This was an expected result from the preparation needed for SEM.

Particle Stability in Dilute Solution

Figure 18:
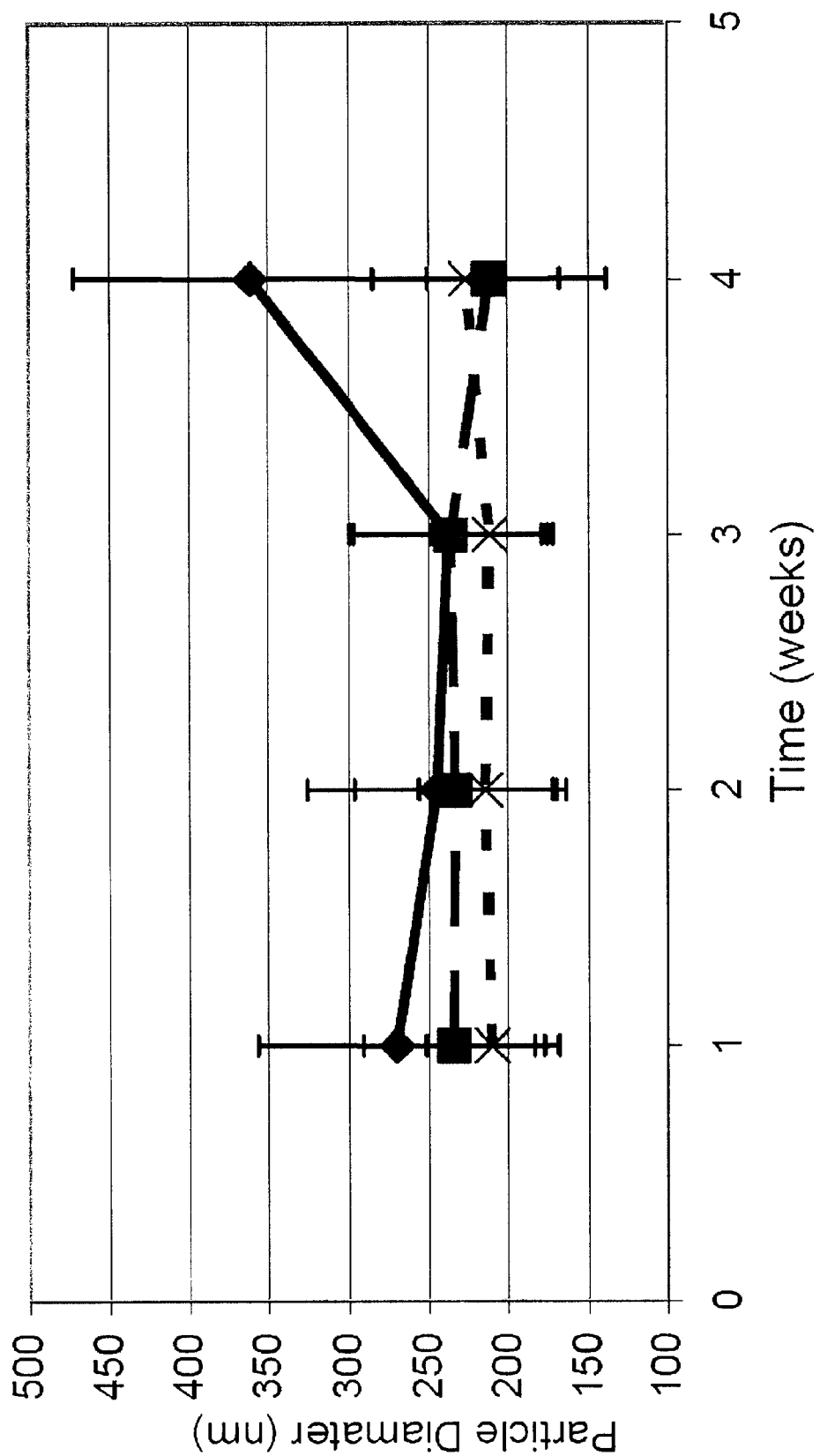
FIG. 18. The stability of the SLN was analyzed as a function of changes in particle diameter over time. An increase in particle diameter indicated a decrease in particle stability. Legend: ♦-Sample #1, ■-Sample #2, X-Sample #3

The stability of the SLN was analyzed by measuring the particle size over time in dilute solution. The advantage of analyzing the particles in dilute solution was that it provided an indication on how the particles will behave in vivo. FIG. 18 displays the results of this study. As seen in the figure, the particles remained stable over the course of 4 weeks. The one exception was sample #2 where the particle size increased from week 3 to week 4. The other two samples were stable throughout the course of the study. In all of the samples, the polydispersity of the particles slightly increased over time. This behavior was especially seen in sample #2. The study was not conducted for any further time course since it would be unrealistic that a nanoparticle would be present for greater than 4 weeks in vivo. Additionally, storage of the particles would most likely be performed in a lyophilized, frozen or more concentrated liquid state and not in a diluted solution.

Encapsulation Efficiency

The encapsulation of PTX in the SLN was analyzed through methanolic extraction followed by HPLC analysis. The samples were lyophilized before methanol extraction in order to avoid any potential adverse effects through the presence of water. Seven independent SLN preparations were formed and analyzed for paclitaxel encapsulation (Table 11). The overall encapsulation was observed to be approximately 34.5% by weight of the paclitaxel present in the solution. This translated into an aqueous solubility of paclitaxel of 238.8 μg/ml, which was a 723 fold increase in aqueous solubility as compared to free paclitaxel. The aqueous solubility of free paclitaxel has been reported to be 0.33 μg/ml, so the approximately 700 fold increase in solubility was determined to be significant.

TABLE 11

The table displays the aqueous concentration of paclitaxel present in the SLN, the percentage by weight of paclitaxel encapsulated in the SLN, and the fold increase in solubility of the encapsulated paclitaxel.

| Sample | Paclitaxel Concentration (μg/ml) | % Encapsulated (w/w %) | Fold Increase in Solubility |
|---|---|---|---|
| 1 | 241.0 | 38.6 | 730 |
| 2 | 225.2 | 36.0 | 682 |
| 3 | 271.7 | 43.5 | 823 |
| 4 | 198.4 | 31.7 | 601 |
| 5 | 273.5 | 35.0 | 848 |
| 6 | 204.4 | 25.2 | 611 |
| 7 | 257.2 | 31.6 | 766 |
| Average | 238.8 ± 30.6 | 34.5 ± 5.8 | 723 ± 97 |

The percentage of encapsulated paclitaxel was 34.5%, so more experimentation was undertaken to identify where the remaining 65.5% of paclitaxel went during the SLN formation process (Table 12). The process of forming one sample was selected to perform the analysis. The pre-emulsion was analyzed first. To characterize the pre-emulsion, the particles (SLN), the left over residue in the mixing tube (tube), and the residue left on the homogenizer tip were all methanol extracted and analyzed. The paclitaxel was found to be encapsulated at almost 90% by weight after the pre-emulsion step. This indicated that the paclitaxel was being lost somewhere in the subsequent high pressure homogenization (HPH) step.

TABLE 12

The amount of encapsulated and non-encapsulated paclitaxel was tracked throughout production of an SLN sample. The overall goal was to satisfy a mass balance where the encapsulated and non encapsulated paclitaxel would add up to the amount of paclitaxel added to the initial solution. The amount of encapsulated paclitaxel was expressed in terms of mass (μg) and aqueous concentration (μg/ml).

| Pre-Emulsion | |
|---|---|
| Sample | Paclitaxel (μg) |
| SLN | 5406.5 |
| Tube | 118.7 |
| Homogenizer Tip | 530.6 |
| % Encapsulated | 89.3 |
| Sum | 6055.7 |

| High Pressure Homogenization | |
|---|---|
| High Pressure Homogenizer Passes | Paclitaxel (μg/ml) |
| 1 | 395.2 |
| 2 | 372.7 |
| 3 | 278.3 |
| 4 | 284.0 |
| 5 | 215.3 |

| Sample | Paclitaxel (μg) |
|---|---|
| Pass 1 | 2568.9 |
| Pass 2 | 2422.7 |
| Pass 3 | 1809.2 |
| Pass 4 | 1845.7 |
| Pass 5 | 1399.6 |
| Waste 1 | 1062.7 |
| Waste 2 | 800.7 |
| SLN Pellet | 249.7 |
| Waste 1 Pellet | 290.6 |
| waste 2 Pellet | 250.6 |
| Sum PTX | 4053.8 |
| Missing PTX | 1352.6 |

In order to track the paclitaxel in the HPI-1 step, 100 μl samples were taken out of the SLN at the end of each pass. After all the passes were completed the cooled samples were centrifuged and the emulsion was transferred to another tube. The resulting pellet and tube residue (SLN Pellet) was analyzed as one sample. After SLN formation, the HPH was cleaned out with two passes of filtered deionized water (Waste 1 and Waste 2) and their resulting pellets after centrifugation were taken (Waste 1 Pellet and Waste 2 Pellet). As seen in the table, the more passes the SLN emulsion was subjected to the lower the amount of PTX was encapsulated. High amounts of PTX were also present in the two waste samples, indicating loss of the drug in homogenizer. The mass balance was not able to be fully satisfied for the HPH step, but it was hypothesized that some paclitaxel was being precipitated in the loading chamber and the flow path of the HPH which was not able to be recovered for analysis.

In Vitro Cytotoxicity

The in vitro efficacy of the system was assayed by subjecting MCF-7 cells to the loaded particles. The reduction of cell viability of the loaded SLN was also compared to unloaded SLN and PTX solublized in Cremophor EL. The amount of unloaded SLN administered to the particles was the same as the loaded SLN for accurate 168 comparison purposes. The concentration of Cremophor EL was at a maximum 0.1% (v/v %) in the cell media. It was found that any increased concentration caused extreme toxicity to the cells where all of the cells were killed during incubation (data not shown). In order to mitigate this potential confounding parameter, the highest concentration of the Cremophor EL used was 0.1% (v/v %).

Figure 19:
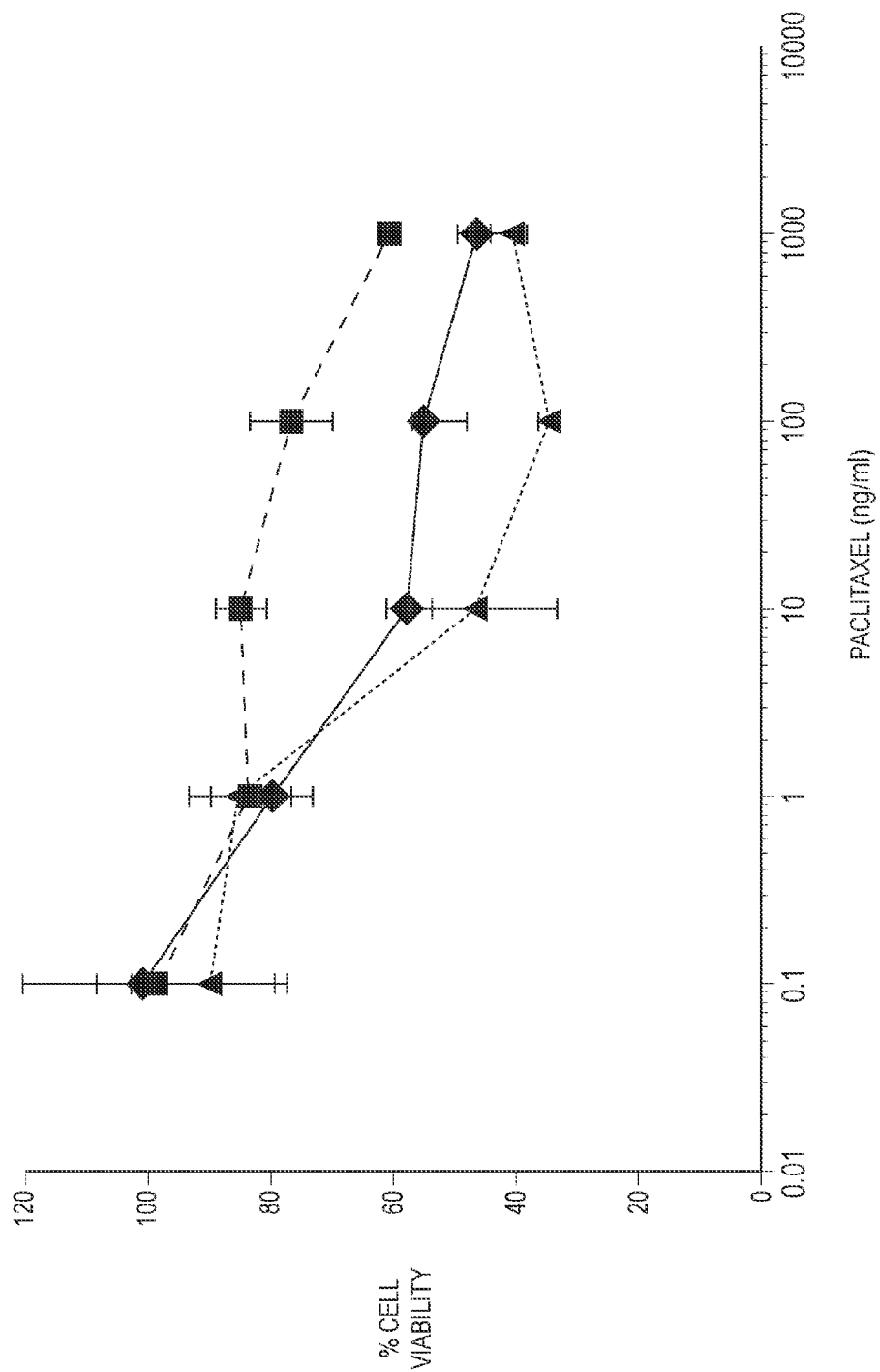
FIG. 19. The effect SLN had on MCF-7 human breast adenocarcinoma cells by plating the cells at 10,000 cells/well and incubating them for three days with PTX loaded SLN, unloaded SLN, and PTX solublized in Cremophor EL. Legend: ■-Unloaded SLN, ♦-PTX solublized in Cremophor EL, ▲-PTX Loaded SLN.

The loaded SLN were able to significantly reduce the viability of cells compared to Cremophor EL at concentrations of 100 ng/ml and 1000 ng/ml PTX. At concentrations less than 100 ng/ml, the two systems exerted the same effects on cell viability. The unloaded particles had a significantly lower effect on cell viability at all doses above 1 ng/ml, indicating a degree of safety of the SLN system (FIG. 19). However, the unloaded particles did demonstrate a slight effect on cell viability at a simulated concentration of 1000 ng/ml. This could be a function of the high concentration of SLN present in the cell media that could possibly exert some malignant effects on the cells. Regardless, it was shown that the developed SLN was safer and more effective than the traditionally used Cremophor EL delivery vehicle.

While the present invention has been described in terms of specific methods and compositions, it is understood that variations and modifications will occur to those skilled in the art upon consideration of the present invention. Those skilled in the art will appreciate, or be able to ascertain using no more than routine experimentation, further features and advantages of the invention based on the above-described embodiments. The practice of the present invention will employ and incorporate, unless otherwise indicated, conventional techniques of cell biology, cell culture, molecular biology, microbiology, genetic engineering, and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. Accordingly, the invention is not to be limited by what has been particularly shown and described. All publications and references are herein expressly incorporated by reference in their entirety.

What is claimed is:

1. A lipid nanoparticle comprising a therapeutic agent dispersed within a lipid core surrounded by an encapsulating high molecular weight polysaccharide, wherein the polysaccharide has trisaccharide repeating units, a molecular weight greater than 3MDa, and is a polyelectrolytic exopolysaccharide isolated from *Acinetobacter* bacteria.

2. The nanoparticle of claim 1, wherein the size of the particle is less than 1 micrometer.

3. The nanoparticle of claim 1, wherein the size of the particle ranges from about 500 nm to about 100 nm.

4. The nanoparticle of claim 1, wherein the lipid core comprises at least one lipid selected from the group of monoglycerides, diglycerides, triglycerides, waxes and fatty acids.

5. The nanoparticle of claim 1, wherein at least one of the trisaccharide repeating units is N-acetyl galactosamine, N-acetyl glucosamine or a derivative.

6. A method of encapsulating a hydrophobic therapeutic agent comprising dissolving the therapeutic agent in a lipid; mixing the lipid solution with an aqueous solution comprising a high molecular weight polysaccharide having trisaccharide repeating units and a molecular weight greater than 3MDa, wherein the trisaccharide repeating unit comprises formula:

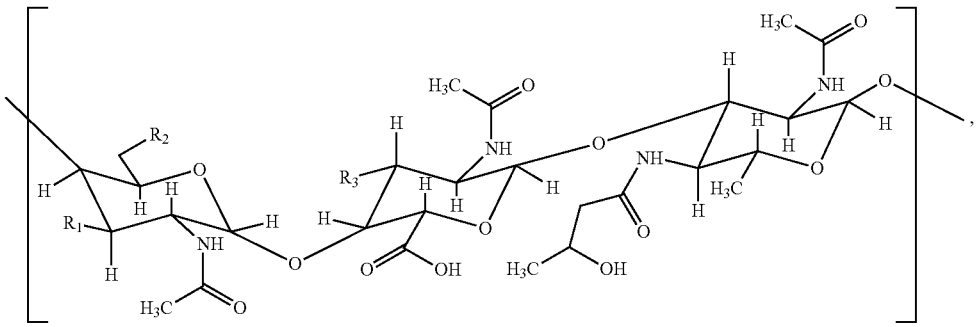

wherein $R_1$, $R_2$ and $R_3$ are selected from the group consisting of OH and OAc; homogenizing the resulting mixture at an elevated temperature to form an emulsion; and cooling the emulsion to form particles having a therapeutic agent dispersed within a lipid core surrounded by the high molecular weight polysaccharide.

7. The method of claim 6, wherein the method further comprises homogenizing the mixture at a temperature above 60 degrees C.

8. The method of claim 6, wherein the polysaccharide is a polyelectrolytic exopolysaccharide isolated from *Acinetobacter* bacteria.

9. The method of claim 6, wherein the lipid comprises at least one lipid selected from the group of monoglycerides, diglycerides, triglycerides, waxes and fatty acids.

10. The method of claim 6, wherein the step of cooling the emulsion further comprises solidifying the core lipid.

11. A therapeutic nanoparticle comprising a therapeutic agent bound together with a high molecular weight cationic polysaccharide cross-linked with a polyanion, wherein the polysaccharide comprises tri-saccharide repeating units and a molecular weight greater than 3MDa in an uncross-linked state, and wherein the trisaccharide repeating unit comprises formula:

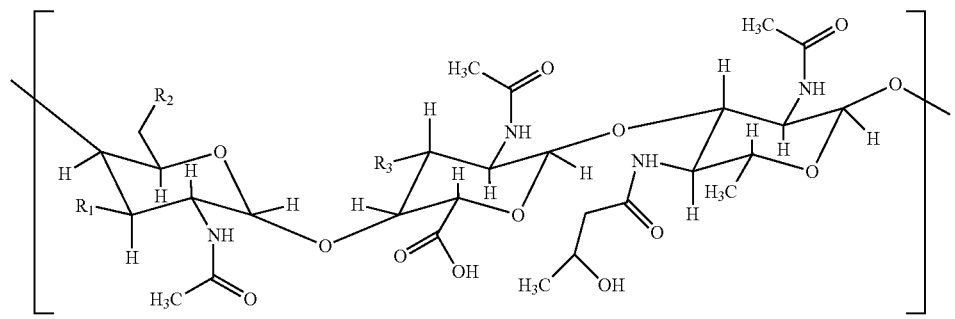

And wherein $R_1$, $R_2$ and $R_3$ are selected from the group consisting of OH and OAc.

12. The nanoparticle of claim 11, wherein the size of the particle is less than 1 micrometer.

13. The nanoparticle of claim 11, wherein the size of the particle ranges from about 300 nm to about 50 nm.

14. The nanoparticle of claim 11, wherein at least one of the trisaccharide repeating units is N-acetyl galactosamine, N-acetyl glucosamine or a derivative.

15. The nanoparticle of claim 11, wherein the polysaccharide is a polyelectrolytic exopolysaccharide isolated from *Acinetobacter* bacteria.

16. The nanoparticle of claim 11, wherein the polyanion is tripolyphosphate (TPP).

* * * * *